(12) United States Patent
Kachi et al.

(10) Patent No.: US 9,125,839 B2
(45) Date of Patent: Sep. 8, 2015

(54) COMPOSITION FOR EXTERNAL USE ON SKIN, COSMETIC, AND CLEANING AGENT

(75) Inventors: Hisanori Kachi, Yokohama (JP); Makoto Matsuzawa, Yokohama (JP); Minaho Ookubo, Yokohama (JP); Keiichi Oyama, Yokohama (JP); Aki Gotou, Yokohama (JP); Masaaki Kojima, Ina (JP); Takehiko Sakai, Ina (JP); Junichi Itou, Ina (JP)

(73) Assignee: The Nisshin Oillio Group, Ltd., Tokyo (JP)

( * ) Notice: Subject to any disclaimer, the term of this patent is extended or adjusted under 35 U.S.C. 154(b) by 0 days.

(21) Appl. No.: 13/583,853

(22) PCT Filed: Mar. 14, 2011

(86) PCT No.: PCT/JP2011/055901
§ 371 (c)(1),
(2), (4) Date: Sep. 10, 2012

(87) PCT Pub. No.: WO2011/111854
PCT Pub. Date: Sep. 15, 2011

(65) Prior Publication Data
US 2013/0029932 A1    Jan. 31, 2013

(30) Foreign Application Priority Data

Mar. 12, 2010  (JP) ................................ 2010056267
Jun. 25, 2010  (JP) ................................ 2010145351
Jul. 16, 2010  (JP) ................................ 2010161625
Nov. 17, 2010  (JP) ................................ 2010256951
Feb. 4, 2011  (JP) ................................ 2011022736

(51) Int. Cl.
*A61K 31/715* (2006.01)
*C08B 37/00* (2006.01)
*C08B 37/12* (2006.01)
*A61K 8/73* (2006.01)
*A61K 8/06* (2006.01)
*A61K 8/34* (2006.01)
*A61Q 19/00* (2006.01)
*A61Q 1/02* (2006.01)
*A61Q 17/04* (2006.01)
*A61Q 19/10* (2006.01)
*A61Q 5/02* (2006.01)

(52) U.S. Cl.
CPC ... *A61K 8/73* (2013.01); *A61K 8/06* (2013.01); *A61K 8/345* (2013.01); *A61Q 19/00* (2013.01); *A61K 2800/5922* (2013.01); *A61Q 1/02* (2013.01); *A61Q 5/02* (2013.01); *A61Q 17/04* (2013.01); *A61Q 19/10* (2013.01)

(58) Field of Classification Search
CPC ........... A61K 8/06; A61K 8/345; A61K 8/73; A61K 2800/5922; A61Q 19/00; A61Q 1/02; A61Q 19/10; A61Q 5/02; A61Q 17/04

USPC ........................ 514/54, 23; 536/123.1, 124
See application file for complete search history.

(56) References Cited

U.S. PATENT DOCUMENTS 4,826,700 A    5/1989   Bayerlein et al.

FOREIGN PATENT DOCUMENTS

| DE | 10033975 A1 | 1/2002 |
|---|---|---|
| EP | 2149631 A1 | 2/2010 |
| JP | 05178723 A | 7/1993 |
| JP | 05317008 A | 12/1993 |
| JP | 7-165559 A | 6/1995 |
| JP | 10146174 A | 6/1998 |
| JP | 10167948 A | 6/1998 |
| JP | 11-209262 A | 8/1999 |
| JP | 11292750 A | 10/1999 |
| JP | 2000119166 A | 4/2000 |
| JP | 2001213756 A | 8/2001 |
| JP | 2001261525 A | 9/2001 |
| JP | 2002000224 A | 1/2002 |
| JP | 2007-154117 A | 6/2007 |
| JP | 2008050298 A * | 3/2008 |
| JP | 2009-082103 A | 4/2009 |
| JP | 2010013428 A | 1/2010 |
| WO | 9523815 A1 | 9/1995 |
| WO | 9951716 A1 | 10/1999 |

OTHER PUBLICATIONS

Suzuki (JP 2010-013428; Jan. 21, 2010 (English Machine Translation).*
Fukuda et al.; JP 2008050298 A; Mar. 6, 2008 (English Machine Translation).*

(Continued)

*Primary Examiner* — Shaojia Anna Jiang
*Assistant Examiner* — Michael C Henry
(74) *Attorney, Agent, or Firm* — Wood, Herron & Evans, LLP

(57) ABSTRACT

A composition for external use on skin that can be spread evenly on the skin, does not produce a liquid residue as a result of temperature change, and can suppress a feeling of sliminess of xanthan gum is provided. There are provided a composition for external use on skin containing 0.1% by mass to 10% by mass of a component (A) (a water-soluble polymer obtained by mixing agar with xanthan gum) and 30% by mass or more of a component (D) (water); the composition for external use on skin containing 0.5% by mass to 40% by mass of a divalent polyol as a component (B); the composition for external use on skin according to any one of the above compositions, which contains moisturizers as a component (C); and the composition for external use on skin according to any one of the above compositions, which contains oil as a component (E).

21 Claims, 2 Drawing Sheets

(56) References Cited

OTHER PUBLICATIONS

Jun'ichi Ito, et al., "Shinki Kanten no Kaihatsu Oyobi sono Tenkai ni Tsuite", Food chemicals, May 1, 2006, vol. 22, No. 5, pp. 40-44, Okutsuke.

International Search Report issued in International Application No. PCT/JP2011/055901, dated Jun. 14, 2011, 3 pages.

Monthly Hood Chemicals, vol. 18, No. 8, pp. 45-48, and partial English translation (Aug. 1, 2002).

An Incoporated Company Health Industry Newspaper Publishing Company, "Food and Development," vol. 29, No. 2, pp. 8-10, and partial English translation (Feb. 1, 1994).

Kyoritsu Shuppan Co. Ltd., "Chemistry Great Dictionary 2," 1st Edition, pp. 662-663, and partial English translation (Jun. 30, 1960).

Kyoritsu Shuppan Co., Ltd., "Chemistry Great Dictionary 1," 1st Edition, p. 28 and partial English translation (Mar. 30, 1960).

Japanese Patent Office, Notice of Reasons for Rejection issued in corresponding Japanese Patent Application No. 2012-504553 and English-language translation Mar. 3, 2015.

European Search Report issued in European Patent Application No. 11753509.6, mailed Jul. 6, 2015, 11 pages.

\* cited by examiner

COMPOSITION FOR EXTERNAL USE ON SKIN, COSMETIC, AND CLEANING AGENT

TECHNICAL FIELD

The present invention relates to a composition for external use on skin that does not produce a liquid residue as a result of temperature change, can be evenly spread on the skin, does not generate a dirt-like scum when applied to the skin, reduces a feeling of sliminess of xanthan gum, and inhibits hands used for applying a cosmetic from becoming slippery even when hands come into contact with moisture after the application of the cosmetic. The present invention also relates to a cosmetic containing this composition for external use on skin.

Priority is claimed on Japanese Patent Application No. 2010-056267, filed Mar. 12, 2010, Japanese Patent Application No. 2010-145351, filed Jun. 25, 2010, Japanese Patent Application No. 2010-161625, filed Jul. 16, 2010, Japanese Patent Application No. 2010-256951, filed Nov. 17, 2010, and Japanese Patent Application No. 2011-022736, filed Feb. 4, 2011, the content of which is incorporated herein by reference.

BACKGROUND ART

Various moisturizers have been mixed with agents for external use on skin such as cosmetics in the related art. As typical moisturizers, hyaluronic acid, pyrrolidone carboxylate, glycerin, and the like are widely used. Although these have a high moisturizing effect, if a large amount of the moisturizer is mixed in to improve the effect, a feeling of stickiness to the skin becomes strong, which results in undesirable feeling during use in some cases. It is known that mixing oil together with a moisturizer is effective for suppressing the feeling of sliding and feeling of stickiness of the moisturizer. Moreover, an attempt at using a specific copolymer, a polyoxyethylene derivative, and a water-soluble polymer concurrently with a moisturizer is being made.

In order to relieve the feeling of stickiness of a moisturizer, a method of mixing in a polyoxyethylene polyoxypropylene copolymer and polyethylene glycol dialkyl ether has been reported (PTLS 1 and 2). However, with the components disclosed in these patent literature documents, an emulsion stabilizing effect for oil is not expected. Consequently, many restrictions are imposed on formulation, and the effect of suppressing stickiness is limited.

PTL 3 reports a method of reducing the feeling of stickiness of a moisturizer by mixing in native gellan gum. However, since the native gellan gum forms a hard and brittle gel, the moisturizer is not evenly spread when being applied to the skin, which leads to a defect that uniform coating is difficult.

Various types of water-soluble ionic substances are mixed into cosmetics in many cases. Examples of the water-soluble ionic substances include ascorbic acid derivatives as whitening components or as other active ingredients, pH adjustors and sequestering agents for preventing alteration of cosmetics or for maintaining usability of cosmetics, and the like.

However, since the gel strength of the native gellan gum changes in the presence of water-soluble ionic substances, mixing in of these components is restricted in terms of formulation.

When agents for external use on skin including cosmetics are applied, the agents are spread on the skin by using fingers. If the agent for external use on skin attached to the fingers used for the application absorbs moisture, the components mixed into the agent for external use on skin exhibit a lubricating property, even once the agent has dried. Accordingly, when delicate work such as gripping a pen, closing the cap of a container, and picking up small objects are carried out after the application of the agent for external use on skin, the lubricating property hinders this work in some cases. Therefore, it is desired to develop a composition for external use on skin that prevents fingers used for application from easily becoming slippery even when the fingers come into contact with moisture again.

In addition, an oil-in-water type emulsion composition such as an emulsion or a cream has been widely used as cosmetics in the related art. Particularly, for cosmetics, silicone oil or oil having a high polarity is widely used as an oil which is pleasing to the sense of touch. However, since these oils are not easily emulsified, it is difficult to realize stabilization of an emulsion dispersion.

In order to keep the emulsion dispersion of oil stable, it is indispensable to add a surfactant. However, in recent years, higher safety has been required for cosmetics, so mixing a surfactant has become a problem in some cases. Particularly, for agents for external use applied to the skin, the amount of the surfactant added is desired to be small in terms of safety. However, it is difficult to reduce the amount of the surfactant added while also stabilizing the emulsion dispersion.

Generally, for emulsifying and stabilizing oil, a thickener represented by a carboxyvinyl polymer or xanthan gum is effective. Accordingly, for example, PTL 4 discloses a method of using an alkyl-modified carboxyvinyl polymer as an emulsifier, as a method of preparing an oil-in-water type emulsion cosmetic excellent in long term stability without using a surfactant. However, these thickeners are not preferable since they produce the dirt-like scum during massage when applied to the skin.

In addition, the carboxyvinyl polymer has a problem in that the viscosity is dramatically reduced in the presence of a water-soluble ionic substance such as an ascorbic acid derivative, so the stability deteriorates in some cases. Particularly, the alkyl-modified carboxyvinyl polymer has low halotolerance, which leads to a problem that this polymer cannot be mixed with a vitamin C derivative or other salt. Furthermore, though the xanthan gum shows small change in physical properties with respect to water-soluble ionic substances, nevertheless the feeling of sliminess or stickiness unique to the xanthan gum is not preferred. In addition, the xanthan gum has a defect in that the sense of touch is greatly worsened when the xanthan gum is mixed in, in a sufficient amount for securing stability.

PTL 5 discloses, as an oil-in-water type cosmetic with improved stability and halotolerance, a fluid gel (gel having fluidity) cosmetic that contains one or two or more kinds among agar, carrageenan, gellan gum, and sodium alginate as a main fluid gel agent, and contains one or two or more kinds among native gellan gum, xanthan gum, guar gum, locust bean gum, a carboxyvinyl polymer, an acrylic acid-alkyl methacrylate copolymer, hydroxyethyl cellulose, and hydroxypropyl cellulose as an agent for improving usability and stability. This fluid gel cosmetic is characterized by having an even and smooth fine gel-dispersed structure. However, this cosmetic has a problem in that a water-soluble gelation agent having disintegrating properties, such as heated and dissolved gellan gum or agar cannot be produced by stirring and cooling used in the related art but has to be produced while breaking the formed gel by means of applying a high shearing force during cooling.

PTLS 6 and 7 report low-strength agar and how to use this agar. Though a property of producing a liquid residue, which is an original property of agar, is improved to some degree in the documents, the improvement does not satisfy stability required for agents for external use on skin such as cosmetics. Moreover, the agar has a problem of producing the dirt-like scum during massage and is ineffective for stabilizing an emulsion dispersion of silicone oil or high-polarity oil which is not easily emulsified. Therefore, it is desired to develop a composition for external use on skin that improves the property of producing a liquid residue, which is an original property of agar, and does not produce the dirt-like scum.

Oil-in-water type emulsion compositions containing pigments are being used as emulsion cosmetics such as sunscreen cosmetics and a liquid foundation. As a method of stably dispersing pigments in the oil-in-water type emulsion composition, a method of using various surfactants, a method of using water-soluble polymers, and the like are being examined. However, in the method of using various surfactants, deterioration of makeup sustainability and stickiness caused by the decrease in water resistance and oil resistance is an issue. In addition, in the method of using water-soluble polymers, depending on the type of water-soluble polymers, the polymers are aggregated when being concurrently used with pigments in some cases. Furthermore, if water-soluble polymers are mixed in until a desired viscosity is obtained, problems in sense of touch such as stickiness and feeling of a film arise, and change with temperature variation becomes large, which leads to a defect that the stabilized form of a product cannot be easily maintained.

Powders such as pigments used for cosmetics are divided into hydrophilic powder and hydrophobic powder. In order to impart water resistance and water repellency to cosmetics, powder having undergone hydrophobizing treatment is used. However, since hydrophobic powder has low affinity with water in general, it is very difficult to evenly disperse hydrophobic powder in the oil-in-water type emulsion composition. As a method of stably dispersing the hydrophobic powder in the oil-in-water type emulsion composition, a method using a water-soluble solidifying agent such as agar or gelatin and a water-soluble adhesive such as methyl cellulose or xanthan gum has been reported (for example, see PTL 8). However, since general agar has a high molecular weight and forms a very strong network, spreadability of the obtained oil-in-water type emulsion composition is poor at the time of application in some cases. Consequently, it is desired to develop a pigment dispersion composition that can be stably dispersed regardless of the type of pigment, spreads excellently on the skin, is excellently pleasing to the sense of touch, and is highly safe for the skin.

Meanwhile, cleaning agents containing a surfactant as a main agent need to be thickened to an appropriate degree in some cases, in consideration of usability for a user and dispersion stability of insoluble solids contained. Examples of thickening methods used in the related art include three methods such as a method of increasing viscosity by forming a complex by means of mixing in different types of surfactants (for example, amphoteric and anionic surfactants), a method of increasing viscosity by micelle aggregation by adding an inorganic salt, and a method of using a thickener.

In a case of the method of using a combination of different types of surfactants, the amount of the surfactants contained tends to be increased. Furthermore, depending on the type of the surfactant used as a main agent, it is very difficult to increase viscosity in some cases. Examples thereof include cleaning agent compositions containing disodium polyoxyethylene lauryl sulfosuccinate, cocoyl-L-glutamic acid monotriethanolamine, polyoxyethylene lauryl ether sodium acetate, cocamidopropyl betaine, and the like as main agents. Many of these surfactants having a poor thickening property and a mixture thereof are generally considered to be hypoallergenic, so these can be expected to be used for various uses. However, even if other surfactants are combined with these surfactants, a desired viscosity is not easily achieved in many cases.

In the method of increasing viscosity by mixing in an inorganic salt, sodium chloride, sodium sulfate, or the like is mainly used as the inorganic salt. However, the thickening effect of these inorganic salts is low for the amount of the salts added, and in order to adjust the viscosity to a desired degree, a large amount of the inorganic salts need to be added, which leads to a problem in safety such as cause a sensation of irritation.

In the method of increasing viscosity by using a thickener, nonionic surfactants or polymeric thickeners are widely used. As the nonionic surfactants, polyoxyethylene alkyl ether, coconut oil fatty acid diethanolamide, polyethylene glycol distearic acid ester, and the like are used. However, these nonionic surfactants have problems in that they need to be added in a large amount, are not pleasant to the sense of touch when used, have poor low-temperature stability and poor solubility, and the like.

On the other hand, as the polymeric thickeners, hydroxymethyl cellulose, hydroxyethyl cellulose, carboxymethyl cellulose, cationized cellulose, polyvinyl alcohol, sodium polyacrylate, starch, xanthan gum, and the like are used. In the method of using the polymeric thickeners, it is possible to obtain a viscous cleaning agent composition with a relatively low level of the thickeners, and the thickeners can be easily added to hypoallergenic cleaning agent compositions highly safe for the skin. However, in cleaning agents containing the polymeric thickener concurrently with a water-soluble ionic substance, the thickening effect is diminished in many cases. The xanthan gum has the thickening effect even in the presence of water-soluble ionic substances, and can thicken hypoallergenic cleaning agent compositions that are considered not to be easily thickened. However, the xanthan gum has defects in that its characteristic feeling of sliminess is not preferred and that its sense of touch greatly deteriorates when the xanthan gum is mixed in, in a sufficient amount to secure stability.

Cleaning agents used for cleaning skin, such as a shampoo and a cleansing agent, are required to be highly safe for the skin. Among these, cleaning agents for babies or pets are desired to be safe even being swallowed, since there is a possibility that babies or pets may accidently swallow the cleaning agents when the agents are used. Therefore, it is desired to develop a cleaning composition that is excellent in safety, is excellently pleasing to the sense of touch when used, is hypoallergenic, and has a necessary viscosity.

Against the above-described background, it is desired to develop a composition for external use on skin that can be evenly spread on the skin, does not produce a liquid residue as a result of temperature change, can reduce the feeling of sliminess of xanthan gum, and can stably contain various other components.

DOCUMENTS OF RELATED ART

Patent Literature

[PTL 1] Japanese Unexamined Patent Application Publication No. 2001-213756
[PTL 2] Japanese Unexamined Patent Application Publication No. Hei 10-167948
[PTL 3] Japanese Unexamined Patent Application Publication No. Hei 11-292750

[PTL 4] Japanese Unexamined Patent Application Publication No. 2001-261525
[PTL 5] Japanese Unexamined Patent Application Publication No. 2000-119166
[PTL 6] Japanese Unexamined Patent Application Publication No. Hei 5-317008
[PTL 7] Japanese Unexamined Patent Application Publication No. Hei 10-146174
[PTL 8] Japanese Unexamined Patent Application Publication No. Hei 5-178723

DISCLOSURE OF INVENTION

Problems to be Solved by the Invention

An object of the present invention is to provide a composition for external use on skin that spreads excellently on the skin, excellently penetrate the skin, does not produce a liquid residue even with temperature change, can reduce the feeling of sliminess of xanthan gum, and can stably contain various other components.

Means to Solve the Problems

The present inventors repeated thorough research to solve the above problems. As a result, they found that by mixing in a water-soluble polymer that is obtained by mixing agar having a smaller weight average molecular weight than that of general agar, specifically, agar having a weight average molecular weight of 10000 to 60000 with xanthan gum at a specific ratio, a composition that does not produce a liquid residue even with temperature change and spreads excellently on the skin is obtained. They also found that this composition exhibits excellent stability even being mixed with oil, a water-soluble ionic substance, or a moisturizer, can reduce the feeling of sliminess caused by xanthan gum, does not generate dirt-like scum during massage, and suppresses a lubricating property when fingers used for application come into contact with moisture again, whereby the present inventors completed the present invention.

That is, a first aspect of the present invention is a composition for external use on skin that contains 0.1% by mass to 10% by mass of the following component (A) and 30% by mass or more of the following component (D).

Component (A): A water-soluble polymer obtained by mixing agar having a weight average molecular weight of 10000 to 60000 with xanthan gum at a ratio of 4:6 to 8:2 in terms of a mass ratio.

Component (D): Water

A second aspect of the present invention is the composition for external use on skin according to the first aspect, further containing 0.5% by mass to 40% by mass of a divalent polyol as a component (B).

A third aspect of the present invention is the composition for external use on skin according to the second aspect, further containing 0.001% by mass to 20% by mass of one or more kinds of moisturizers selected from hyaluronic acid or salts thereof, pyrrolidone carboxylate or salts thereof, glycerin, diglycerin, and polyglycerin, as a component (C).

A fourth aspect of the present invention is the composition for external use on skin according to any one of the first to third aspects, further containing 5% by mass to 60% by mass of powder as a component (H).

A fifth aspect of the present invention is the composition for external use on skin according to the fourth aspect, wherein the component (H) is hydrophobic powder.

A sixth aspect of the present invention is the composition for external use on skin according to any one of the first to fifth aspects, further containing 0.01% by mass to 64% by mass of oil as a component (E).

A seventh aspect of the present invention is the composition for external use on skin according to the sixth aspect, wherein the oil as the component (E) contains one or more kinds of silicone oils selected from chain-like polysiloxane and cyclic polysiloxane.

An eighth aspect of the present invention is the composition for external use on skin according to the sixth aspect, wherein the component (E) contains oil having a relative permittivity at 20° C. of 3.0 or more.

A ninth aspect of the present invention is the composition for external use on skin according to any one of the sixth to eighth aspects, wherein the component (E) contains two or three or more kinds of oils incompatible with each other, and the oils are held in the composition while being incompatible with each other.

A tenth aspect of the present invention is the composition for external use on skin according to any one of the first to ninth aspects, in which practically no surfactant is mixed in.

An eleventh aspect of the present invention is the composition for external use on skin according to any one of the first to sixth aspects, further containing 0.001% by mass to 60% by mass of a surfactant as a component (F).

A twelfth aspect of the present invention is the composition for external use on skin according to the eleventh aspect, wherein the component (F) is an ionic surfactant.

A thirteenth aspect of the present invention is the composition for external use on skin according to the eleventh aspect, wherein the component (F) is an amphoteric surfactant.

A fourteenth aspect of the present invention is the composition for external use on skin according to any one of the first to thirteenth aspects, wherein a value of Mw/Mn of a weight average molecular weight (Mw) and a number average molecular weight (Mn) of the agar in the component (A) is 1.1 to 8.0.

A fifteenth aspect of the present invention is the composition for external use on skin according to any one of the second to fourteenth aspects, wherein the divalent polyol as the component (B) has 3 to 6 carbon atoms.

A sixteenth aspect of the present invention is the composition for external use on skin according to any one of the second to fourteenth aspects, wherein the divalent polyol as the component (B) is one or more kinds selected from propylene glycol, 1,3-propanediol, 1,3-butylene glycol, 3-methyl-1,3-butanediol, 1,2-pentanediol, dipropylene glycol, 1,2-hexanediol, and hexylene glycol.

A seventeenth aspect of the present invention is the composition for external use on skin according to any one of the second to sixteenth aspects, wherein the divalent polyol as the component (B) is contained 0.5% by mass to 30% by mass.

An eighteenth aspect of the present invention is the composition for external use on skin according to any one of the first to seventeenth aspects, containing 0.01% by mass to 10% by mass of one or more kinds selected from water-soluble ionic substances.

A nineteenth aspect of the present invention is the composition for external use on skin according to the eighteenth aspect, wherein the water-soluble ionic substance is one or more kinds selected from a group consisting of ascorbic acid, an ascorbic acid derivative, and salts thereof.

A twentieth aspect of the present invention is the composition for external use on skin according to any one of the first to nineteenth aspects, which is produced by a step of holding a water-soluble polymer solution, which contains the water-soluble polymer as the component (A) and at least all or a portion of water as the component (D) and in which the water-soluble polymer as the component (A) exists in a dissolved state, at 85° C. to 95° C. for 50 minutes or longer.

A twenty-first aspect of the present invention is a cosmetic containing the composition for external use on skin according to any one of the first to twentieth aspects.

A twenty-second aspect of the present invention is a cleaning agent containing the composition for external use on skin according to any one of the eleventh to twentieth aspects.

A twenty-third aspect of the present invention is a method of producing a cosmetic, wherein a powder dispersion composition that contains 0.1% by mass to 10% by mass of the following component (A), 30% by mass or more of the following component (D), and 5% by mass to 60% by mass of the following component (H) is used as a cosmetic raw material.

Component (A): A water-soluble polymer obtained by mixing agar having a weight average molecular weight of 10000 to 60000 with xanthan gum at a ratio of 4:6 to 8:2 in terms of a mass ratio.

Component (D): Water

Component (H): Powder

A twenty-fourth aspect of the present invention is a method of producing a composition for external use on skin, the method including a step of holding a water-soluble polymer solution, which contains the water-soluble polymer as the component (A) and at least all or a portion of water as the component (D) and in which the water-soluble polymer as the component (A) exists in a dissolved state, at 85° C. to 95° C. for 50 minutes or longer.

Effects of the Invention

According to the present invention, it is possible to provide a composition for external use on skin and a cosmetic that is spread excellently on the skin, excellently penetrate the skin, do not easily produce a liquid residue as a result of temperature change, do not impart a feeling of sliminess, and can stably contain various other components.

DESCRIPTION OF EMBODIMENTS

Figure 1:
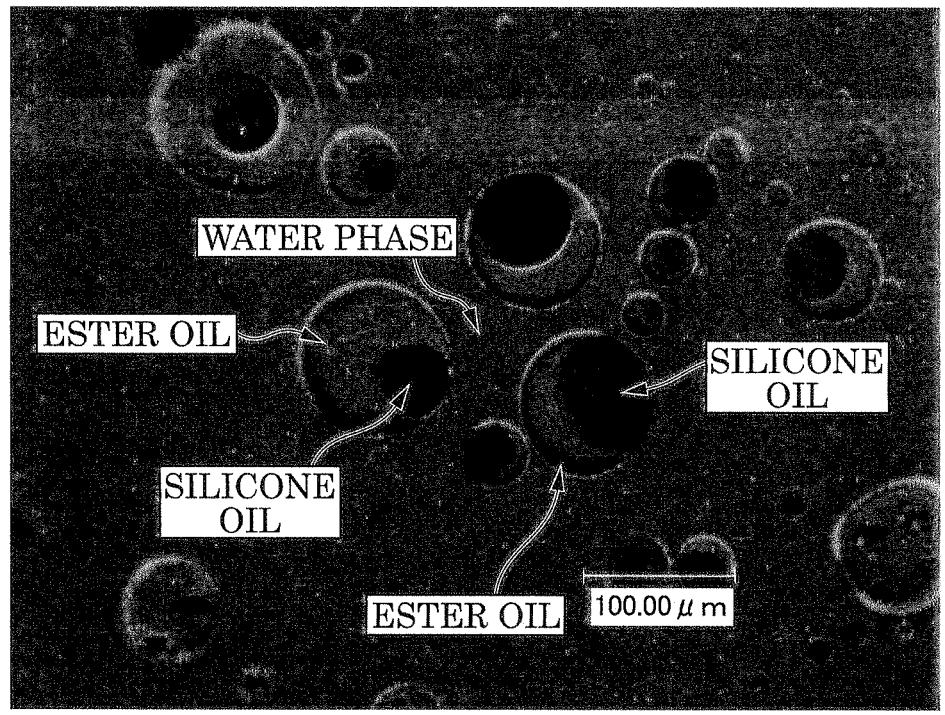
FIG. 1 is a microscopic image of the oil-in-water type emulsion composition of Example 53.

In the present invention and the present specification, the "composition for external use on skin" refers to a composition that is used by being brought into direct contact with skin (including scalp). Accordingly, the "composition for external use on skin" includes a cosmetic composition, a pharmaceutical composition, a cleaning composition, and the like.

Hereinbelow, the present invention will be described in detail.

The composition for external use on skin of the present invention contains 0.1% by mass to 10% by mass of the following component (A) and 30% by mass or more of the following component (D).

Component (A): A water-soluble polymer obtained by mixing agar having a weight average molecular weight of 10000 to 60000 with xanthan gum at a ratio of 4:6 to 8:2 in terms of a mass ratio.

Component (D): Water

The weight average molecular weight of the agar (hereinbelow, referred to as "low-molecular weight agar" in some cases) that constitutes the water-soluble polymer as the component (A) and has a weight average molecular weight of 10000 to 60000 is preferably 10000 to 60000, more preferably 20000 to 60000, even more preferably 30000 to 60000, still more preferably from 40000 to 60000, and most preferably 43000 to 60000. When the agar having a weight average molecular weight exceeding 60000 is used, penetration to skin becomes poor, the composition for external use on skin cannot be evenly spread on skin, and the feeling during use worsens due to dirt-like scum generated. Moreover, a liquid residue is produced, so stability becomes problematic. In addition, if the fingers used for application come into contact with moisture after being dried, the fingers obtain a lubricating property, which leads to a concern that delicate work may be hindered. Particularly, when the composition for external use on skin of the present invention further contains the moisturizer as the component (C) described later, if agar having a weight average molecular weight of exceeding 60000 is used, the effect of suppressing stickiness of the moisturizer is lost.

The low-molecular weight agar used in the present invention preferably has a narrow molecular weight distribution. The molecular weight distribution is indicated by a value (Mw/Mn) obtained by means of dividing a weight average molecular weight (Mw) by a number average molecular weight (Mn).

The number average molecular weight (Mn) is an average of molecular weights of single molecules. Consequently, if the molecular weight distribution is wide, and the number of molecules having a low molecular weight is large, the number average molecular weight (Mn) becomes small by being influenced by this state. On the other hand, the weight average molecular weight (Mw) is an average based on the weight fraction of molecules. Accordingly, even if the molecular weight distribution is wide, and the number of molecules having a low molecular weight is large, these low-molecular weight components influence the total weight insignificantly, so the change in the weight average molecular weight (Mw) is small. That is, the smaller the value (Mw/Mn) obtained by dividing the weight average molecular weight (Mw) by the number average molecular weight (Mn), the narrower the molecular weight distribution, and the greater the value, the wider the molecular weight distribution.

The low-molecular weight agar used in the present invention preferably has a low molecular weight, and the value of Mw/Mn showing the molecular weight distribution of the agar is preferably 1.1 to 8.0, more preferably 1.5 to 7.0, even more preferably 2.0 to 6.0, and most preferably 2.5 to 5.5. If the molecular weight distribution is within this range, it is possible to obtain effects in which the composition for external use on skin of the present invention spreads excellently on skin, excellently penetrate skin, does not generate dirt-like scum, is excellent in stability even being mixed with oil, a moisturizer, and an ionic substance, does not impart a feeling of sliminess, and suppresses a lubricating property caused by water contact. Among these, when the composition for external use on skin of the present invention further contains the moisturizer as the component (C) described later, if the low-molecular weight agar having a molecular weight distribution within this range is used, the feeling of stickiness of the moisturizer is particularly suppressed.

The weight average molecular weight and number average molecular weight of the agar can be measured according to gel permeation chromatography based on HPLC. Specifically, agar is dissolved in distilled water at 95° C. to 97° C., followed by cooling to 50° C., thereby obtaining a sample for measurement. As a liquid chromatography instrument, for example, LC-10AT VP or RID-10A manufactured by Shimadzu Corporation is used. In addition, a differential refractometer is used as a detector, TOSOH TSK-GEL for HPLC, TSK-GEL GMPWXL, or the like manufactured by TOSOH CORPORATION is used as a column, and 0.1 M sodium nitrate or the like is used as a developing solvent. The measurement is performed at a constant temperature. In order to determine the weight average molecular weight and number average molecular weight of agar, pullulan (for example, Shodex STANDARD P-82) of which the molecular weight is already known is used as a standard sample. The standard sample is dissolved in distilled water, and the measurement is carried out under the same conditions by gel permeation chromatography based on HPLC.

As an index showing characteristics of agar, there is gel strength in a 1.5% concentration aqueous solution. The gel strength indicates a force that is applied to a unit area of a plunger at the moment when jelly breaks. A gel strength of the low-molecular weight agar that is usable in the present invention and constitutes the water-soluble polymer as the component (A) is preferably 25 g/cm$^2$ or less, more preferably 15 g/cm$^2$ or less, and most preferably 12 g/cm$^2$ or less. If the gel strength is within this range, it is possible to obtain effects in which the composition for external use on skin of the present invention spreads excellently on skin, excellently penetrate skin, does not generate dirt-like scum, is excellent in stability even being mixed with oil, a moisturizer, and an ionic substance, does not impart a feeling of sliminess, and suppresses a lubricating property caused by water contact. Among these, when the composition for external use on skin of the present invention contains the moisturizer as the component (C) described later, if the low-molecular weight agar having a gel strength within this range is used, the feeling of stickiness of the moisturizer is particularly suppressed.

As disclosed in the above PTL 5, the gel strength is measured in a Nikkansui method at an agar concentration of 1.5%. Specifically, the gel strength of agar is measured in the following manner.

First, an agar sample is weighed and put in a tared container, and deionized water is added thereto, thereby causing the sample to sufficiently absorb water. Subsequently, warm deionized water is added thereto to adjust the content, and the container is heated in a hot water bath to dissolve the sample. In order to make up water evaporating by heating, deionized water is used as a supplement to adjust the content, and the solution is caused to flow into a glass container (for example, a container having an inner diameter of 49 mm and a depth of 57 mm) in which a tape is wound around the upper portion thereof. The container is left to cool at room temperature, and then capped and left in a constant temperature chamber at 20° C. overnight. The tape is peeled off from the glass container, and then jelly around the periphery of the container that sticks out of the container is cut with a cutter and discarded. The strength of the cut surface of the obtained jelly is measured using a texture analyzer or the like. Specifically, a texture analyzer (manufactured by EKO INSTRUMENTS Co., Ltd.) or a rheometer (manufactured by FUDO Kougyou, Inc.) is used as a measurement instrument, a cylindrical plunger having an area of 1 cm$^2$ is mounted thereon, and the sample stage is moved at an appropriate lifting rate. In this manner, a force applied until the jelly breaks can be measured.

The low-molecular weight agar used in the present invention breaks with a very weak force compared to agar used in the related art. As the low-molecular weight agar used in the present invention, agar that is obtained by filling a specific container with a agar solution and gelating this solution and that is pushed out of a hole having a specific size with a small force (a push-out load) is preferable.

The push-out load can be measured by, for example, the following method. First, a cylindrical container (manufactured by EKO INSTRUMENTS Co., Ltd., including a hole having a diameter of 3 mm that is formed in the central portion of the bottom of the container and blocked with a tape) made of acryl that has an inner diameter of 50 mm and a height of 110 mm and is attached to the texture analyzer (manufactured by EKO INSTRUMENTS Co., Ltd.) is filled with 100 g of the same 1.5% by weight hot agar solution as the agar solution prepared for the gel strength measurement, followed by gelation at 20° C. for 18 hours. The tape is removed from the hole, and pressure is applied from the top of the gel by using a plunger having a diameter of 49 mm (advancing rate of 20 mm/min, measurement temperature of 20° C.), whereby the load at the time when the gel breaks and flows out of the hole is measured using the texture analyzer. The load measured in this manner is taken as a push-out load of 1.5% gel. The push-out load of 1.5% gel of the low-molecular weight agar of the present invention is preferably 10 g to 1400 g, more preferably 10 g to 1000 g, even more preferably 10 g to 500 g, and still more preferably 100 g to 300 g.

Examples of the method of obtaining the low-molecular weight agar include a method of cleaving molecules of agar by acid treatment and then removing the effect of the acid used for the acid treatment by neutralization treatment. The agar used in the acid treatment may be either agar that is obtained by redissolving agar having undergone a dehydration step or a freezing and melting step in an extraction step or pulverized and dried agar.

It is also possible to produce the low-molecular weight agar in the first stage of the production. The acid treatment can also be performed in the production process of the agar, for example, in the extraction step, or performed on the agar having undergone any one of the extraction step and a filtering step. Adjusting acid strength and treatment time makes it possible to obtain the low-molecular weight agar of which the molecular weight has been reduced to a desired degree. As a commercially available low-molecular weight agar, "Ena" manufactured by Ina Food Industry Co., Ltd. and the like are usable.

Xanthan gum is a polysaccharide produced by *Xanthomonas campestris* and widely used as a thickener for cosmetics and foods and in other field.

As the xanthan gum constituting water-soluble polymer as the component (A), a commercially available product may be used as is. For example, "NOMCORT Z" and "NOMCORT ZZ" manufactured by The Nisshin OilliO Group, Ltd., "Keltrol" manufactured by CPKelco, and the like are suitably used.

The mixing ratio between the low-molecular weight agar and the xanthan gum constituting the water-soluble polymer as the component (A) is 4:6 to 8:2 in terms of a mass ratio. The mass ratio is preferably 5:5 to 7:3 and more preferably 6:4 to 7:3. The effects of the present invention are obtained when the mass ratio is in this range. When the proportion of the xanthan gum mixed in is large enough to be outside this range, stickiness and sliminess are caused. In addition, when the proportion of the low-molecular weight agar mixed in is large enough to be outside this range, a liquid residue is produced, and the stability deteriorates.

The amount of water-soluble polymer as the component (A) mixed in is 0.1% by mass to 10% by mass, preferably 0.2% by mass to 5% by mass, and even more preferably 0.5% by mass to 3% by mass, based on the composition for external use on skin. If the amount is smaller than 0.1% by mass, the effects of the present invention are diminished. The amount of water-soluble polymer compounded may exceed 10% by mass, but the effects of the present invention are not markedly enhanced in this amount. For example, when the composition for external use on skin of the present invention further contains the moisturizer as the component (C) described later, if the amount of water-soluble polymer as the component (A) mixed in is smaller than 0.1% by mass, the effect of suppressing sliminess of the moisturizer is diminished. Similarly, when the composition for external use on skin of the present invention further contains the oil as the component (E) described later, the effect of improving emulsion stability is diminished. In addition, when the composition for external use on skin of the present invention is a cleaning composition that contains a large amount of the surfactant as the component (F) described later, if the amount of water-soluble polymer as the component (A) mixed in is larger than 10% by mass, the viscosity is increased too much, which leads to a concern of gelation or deterioration of low temperature stability.

The composition for external use on skin of the present invention contains 30% by mass or more, preferably 30% by mass to 95% by mass of water as the component (D). Water is not particularly limited as long as it is generally used as a raw material of an agent for external use on skin, and it is possible to use deionized water, distilled water, water derived from fruits or vegetables, desalted sea water, and the like.

Water derived from fruits and vegetables refers to water removed by distillation in preparing a concentrate of vegetable juice or fruit juice, and contains a minute amount of fragrance components and saccharides in addition to water. The desalted sea water refers to water that is obtained by removing salts from sea water or deep ocean water and is rich in minerals.

The composition for external use on skin of the present invention preferably further contains a divalent polyol as a component (B), in addition to the components (A) and (D). If the composition for external use on skin of the present invention contains the component (B), the amount of the contained divalent polyol as the component (B) is preferably 0.5% by mass to 40% by mass, more preferably 0.5% by mass to 30% by mass, even more preferably 1.0% by mass to 25% by mass, still more preferably 2% by mass to 25% by mass, and particularly preferably 4% by mass to 20% by mass. If the divalent polyol is mixed in in this range, the effect of suppressing the production of a liquid residue is particularly enhanced, and a composition for external use on skin that is excellent in storage stability can be prepared. Particularly, when the composition for external use on skin of the present invention further contains the moisturizer as the component (C) described later, if the divalent polyol is mixed in within this range, sliminess of the moisturizer can be reduced. Moreover, when a monol or a polyol having a valency of three or higher is used instead of the divalent polyol, the above effect becomes insufficient.

The divalent polyol used as the component (B) is preferably a divalent polyol having 3 to 6 carbon atoms. If the divalent polyol has 7 or more carbon atoms, solubility of the component (D) in water deteriorates, so it is difficult to mix in the component (B) in an amount of 0.5% by mass at which the effect of the component (B) is exerted. Furthermore, when the divalent polyol has 2 or less carbon atoms, the effect of reducing sliminess of the moisturizer is diminished. The divalent polyol having 3 to 6 carbon atoms is preferably one or more kinds selected from propylene glycol, 1,3-propanediol, 1,3-butylene glycol, 3-methyl-1,3-butanediol, 1,2-pentanediol, dipropylene glycol, 1,2-hexanediol, and hexylene glycol, and more preferably one or more kinds selected from propylene glycol, 1,3-propanediol, 3-methyl-1,3-butanediol, 1,2-pentanediol, dipropylene glycol, and 1,2-hexanediol.

The composition for external use on skin of the present invention preferably further contains one or more kinds of moisturizers selected from hyaluronic acid or salts thereof, pyrrolidone carboxylate or salts thereof, glycerin, diglycerin, and polyglycerin, as the component (C). If the water-soluble polymer as the component (A), the divalent polyol as the component (B), and water as the component (D) are added to the moisturizer, the feeling of stickiness of the moisturizer is sufficiently suppressed, and the lubricating property caused when fingers used for application come into contact with moisture again is suppressed. That is, if the moisturizer as the component (C) is further contained, it is possible to obtain a composition for external use on skin that suppresses a feeling of stickiness of the moisturizer, spreads excellently on skin, excellently penetrate skin, does not easily produce dirt-like scum and a liquid residue as a result of temperature change, does not impart a feeling of sliminess, and suppresses the lubricating property caused by water contact.

The hyaluronic acid or salts thereof, pyrrolidone carboxylate or salts thereof, glycerin, diglycerin, and polyglycerin impart moisturizing properties to skin and enhance a water-retaining ability of skin, thereby causing a long-lasting moisturizing sensation. Commercially available products can be used as these components without particular limitation. These moisturizers include water-containing moisturizers, moisturizers in a state of an aqueous solution, dried moisturizers, and the like. However, in the composition for external use on skin of the present invention, the moisturizer is contained as a component excluding moisture, in an amount of 0.001% by mass to 20% by mass, preferably 0.005% by mass to 20% by mass, and more preferably 0.01% by mass to 15% by mass.

Specific examples of the salt of hyaluronic acid and the salt of pyrrolidone carboxylate include a sodium salt, a potassium salt, a magnesium salt, a calcium salt, a barium salt, an ammonium salt, a monoethanolamine salt, a diethanolamine salt, a triethanolamine salt, a monoisopropanolamine salt, a triisopropanolamine salt, and the like.

An average polymerization degree of the polyglycerin is preferably 3 to 20 and more preferably 3 to 10. Specific examples of the polyglycerin having an average polymerization degree of 3 to 20 include triglycerin, tetraglycerin, pentaglycerin, hexaglycerin, and decaglycerin.

The composition for external use on skin of the present invention preferably further contains oil as a component (E). Even if the composition for external use on skin of the present invention is mixed with oil, the emulsion stabilizing effect is high, and the oil can be stably mixed with the composition while suppressing creaming without it being indispensable to use a surfactant. That is, if oil as the component (E) is further contained, it is possible to obtain a composition for external use on skin that is an oil-in-water type emulsion composition which is excellent in storage stability and halotolerance, excellently penetrate skin, spreads excellently on skin, and in which the amount of a surfactant mixed in is reduced or in which practically no surfactant is mixed in. In the present invention and the present specification, the words "practically no surfactant is mixed in" mean that the amount of a surfactant mixed in is 0% by mass to 0.0001% by mass. In addition, in the present invention and the present specification, a property in which viscosity change is small even if a water-soluble ionic substance is mixed in is called halotolerance.

Particularly, in many cases, cosmetics are mixed with oils that exhibit poor compatibility with other components, such as an ultraviolet absorber, silicone oil, and fluorine-based oil. However, when oils mixed in are incompatible with each other, it is very difficult to secure emulsion stability. On the other hand, in the composition for external use on skin of the present invention, for example, even if oils incompatible with each other such as a combination of dipentaerythrityl tripolyhydroxystearate and silicone oil (dimethyl polysiloxane) or a combination of ethylhexyl methoxycinnamate and silicone oil (diemethyl polysiloxane) are mixed, it is possible to stably maintain the emulsified state.

More specifically, when the composition for external use on skin of the present invention is an oil-in-water type emulsion composition containing two kinds of oils incompatible with each other as the component (E), the oils are held in oil beads constituting the emulsion while being incompatible with each other, whereby the emulsified state can be stably maintained. This structure is established in the same manner even when the composition for external use on skin contains three or more types of oils incompatible with each other as the component (E). Needless to say, the composition may contain, as the component (E), oil compatible with at least one kind of oil among these oils, other than the two or more kinds of oils incompatible with each other.

For example, by using the composition for external use on skin of the present invention that is obtained by, as the component (E), a combination of hydrogenated polyisobutene having a high polymerization degree and silicone oil or a combination of hydrogenated polyisobutene having a high polymerization degree and high-polarity oil having low viscosity such as octyldodecyl lactate or erythrityl triethyl hexanoate being contained, it is possible to produce products such as an emulsion foundation and sunscreen that do not easily run down even if they are oil-in-water (O/W) type products. In addition, by using the composition for external use on skin of the present invention that is obtained by combining, as the component (E), silicone having a high polymerization degree or an amino-modified silicone with a high-polarity oil having low viscosity, it is possible to prepare a hair treatment that excellently arranges hair, is not sticky but silky, and feels natural to the touch.

In a case of the oil-in-water type emulsion composition obtained by causing the composition for external use on skin of the present invention to contain oil as the component (E), the amount of the oil as the component (E) contained is preferably 0.01% by mass to 64% by mass, more preferably 0.01% by mass to 40% by mass, even more preferably 0.1% by mass to 30% by mass, and still more preferably 0.5% by mass to 25% by mass.

For example, if the composition for external use on skin of the present invention that contains 0.1% by mass to 10% by mass of the water-soluble polymer as the component (A), 0.5% by mass to 40% by mass of the divalent polyol as the component (B), 0.001% by mass to 20% by mass of the moisturizer as the component (C), 30% by mass or more of water as the component (D), and 0.01% by mass to 40% by mass of the oil as the component (E) is used as an active ingredient, it is possible to produce an oil-in-water type emulsion cosmetic that suppresses the feeling of stickiness of the moisturizer, can be evenly spread on the skin, does not generate a dirt-like scum and a liquid residue even with temperature change, can reduce the feeling of sliminess of xanthan gum, and prevents fingers used for application from becoming slippery even if fingers come into contact with moisture again.

Examples of oil usable as the component (E) include hydrocarbon oils, synthetic ester oils, silicone oil, animal and plant oils, phospholipids, higher fatty acids, higher alcohols, fluorine-based oils, and the like, and one or more kinds of these can be used. It is possible to use any one of these oils whether remaining in a liquid state, a semi-solid state, or a solid state at room temperature, and there is no particular limitation.

Examples of the hydrocarbon oils as the oil of the component (E) include liquid paraffin, isoparaffin, paraffin, an α-olefin oligomer, ozokerite, squalane, pristane, ceresine, squalene, vaseline, microcrystalline wax, paraffin wax, polyethylene wax, and the like.

Examples of the synthetic ester oils include isononyl isononanoate, isodecyl isononanoate, isotridecyl isononanoate, isostearyl myristate, isopropyl myristate, cetyl 2-ethylhexanoate, octyldodecyl myristate, isopropyl palmitate, 2-ethylhexyl palmitate, butyl stearate, hexyl laurate, myristyl myristate, decyl oleate, hexyldecyl dimethyloctanoate, cetyl lactate, myristyl lactate, octyldodecyl lactate, lanolin acetate, isocetyl stearate, isocetyl isostearate, cholesteryl 12-hydroxystearate, phytosteryl 12-hydroxystearate, phytosteryl oleate, ethylene glycol di-2-ethylhexanoate, dipentaerythritol fatty acid ester, alkyl glycol monoisostearate, neopentyl glycol diethylhexanoate, neopentyl glycol dicaprate, glyceryl di-2-heptylundecanoate, pentaerythritol tetra-2-ethylhexanoate, pentaerythritol tetraisostearate, glyceryl tri-2-ethylhexanoate, glyceryl tri(caprylate/caprate), glyceryl triisostearate, glyceryl tri(caprylate/caprate/myristate/stearate), glyceryl trimyristate, glyceryl tricaprylate, glyceryl tricaprate, glyceryl tri-2-heptylundecanoate, trimethylolpropane triisostearate, trimethylolpropane tri-2-ethylhexanoate, di-trimethylolpropane (isostearate/sebacate) oligoester, erythrityl triethylhexanoate, dipentaerythrityl tripolyhydroxystearate, isostearic acid trehalose esters, dipentaerythrityl pentaisostearate, diglyceryl triisostearate, diglyceryl tetraisostearate, diisostearyl malate, castor oil methyl fatty acid ester, isopropyl lanolin fatty acid, oleyl oleate, acetoglyceride, 2-heptylundecyl palmitate, diisobutyl adipate, glyceryl (adipate/2-ethylhexanoate/stearate) oligoester, diglyceryl (2-ethylhexanoate/sebacate) oligoesters, N-lauroyl-L-glutamate-2-octyldodecyl ester, di-2-heptylundecyl adipate, hexyl laurate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, glycerin triisopalmitate, ethyl acetate, butyl acetate, triethyl citrate, glyceryl tri(behenate/isostearate/eicosandioate), glyceryl (behenate/eiosandioate), polyglyceryl (behenate/eiosandioate), bis-ethoxydiglycol succinate, neopentyl glycol diisononanoate, a (polyglyceryl isostearate-2/dimer dilinoleic acid) copolymer, dimer dilinoleic acid hydrogenated castor oil, propanediol di(caprylate/caprate), propanediol diisostearate, polyglyceryl-6 octacaprylate, bis-ethoxy diglycol cyclohexane-1,4-dicarboxylate, and the like.

Examples of the silicone oil include chain-like polysiloxanes such as dimethyl polysiloxane, methyl phenyl polysiloxane, and methyl hydrogen polysiloxane; cyclic polysiloxanes such as octamethyl cyclotetrasiloxane, decamethyl cyclopentasiloxane, dodecamethyl cyclohexasiloxane, and tetrahydrotetramethyl cyclotetrasiloxane; polyoxyethylene polyalkylsiloxane, and the like.

Examples of the animal and plant oils include avocado oil, camellia oil, turtle oil, macadamia nut oil, corn oil, sunflower oil, mink oil, olive oil, rapeseed oil, egg-yolk oil, sesame oil, Prunus persica kernel oil, wheat germ oil, sasanqua oil, castor oil, linseed oil, safflower oil, grape seed oil, cottonseed oil, perilla oil, soybean oil, peanut oil, tea seed oil, kaya oil, rice bran oil, *Aleurities fordi* oil, Japan tung oil, jojoba oil, germ oil, evening primrose oil, cacao butter, coconut oil, beef tallow, mutton tallow, horse tallow, palm seed oil, lard, beef bone fat, tree wax kernel oil, hoof oil, Japan wax, hardened coconut oil, hardened palm oil, hardened beef tallow, hardened castor oil, beeswax, candelilla wax, cotton wax, carnauba wax, bayberry wax, Chinese insect wax, whale wax, montan wax, bran wax, kapok wax, sugarcane wax, lanolin, liquid lanolin, reduced lanolin, hard lanolin, jojoba wax, shellac wax, and the like.

Examples of the phospholipids include lecithins such as soybean phospholipid, hydrogenated soybean phospholipid, rapeseed phospholipid, hydrogenated rapeseed phospholipid, egg-yolk phospholipid, and hydrogenated egg-yolk phopholipid.

Examples of the higher fatty acids include lauric acid, myristic acid, palmitic acid, stearic acid, behenic acid, oleic acid, undecylenic acid, tall oil acid, isostearic acid, linolic acid, linoleic acid, eicosapentaenoic acid (EPA), docosahexaenoic acid (DHA), and the like.

Examples of the higher alcohols include linear alcohols such as lauryl alcohol, cetyl alcohol, stearyl alcohol, behenyl alcohol, myristyl alcohol, oleyl alcohol, and cetostearyl alcohol, branched alcohols such as monostearyl glycerin ether (batyl alcohol), 2-decyltetradecynol, lanolin alcohol, cholesterol, phytosterol, hexyl dodecanol, isostearyl alcohol, and octyl dodecanol, and the like.

Examples of the fluorine-based oil include perfluorodecalin, perfluoroadamantane, perfluorobutyl tetrahydrofuran, perfluorooctane, perfluorononane, perfluoropentane, perfluorodecane, perfluorododecane, and the like.

Among oils usable as the component (E), the composition for external use on skin particularly preferably contains silicone oil or high-polarity oil since these oils are pleasing to the sense of touch. Among these, if the composition contains the high-polarity oil as the component (E), water retentivity of the composition for external use on skin of the present invention can be improved since the high-polarity oil has an excellent water-holding property.

Examples of the high-polarity oil include oil having a relative permittivity at 20° C. of 3.0 or more.

The oil having a relative permittivity at 20° C. of 3.0 or more is used for cosmetics in many cases since this oil shows excellent affinity with skin and is pleasing to the sense of touch. The relative permittivity ($\epsilon_r$) is a value without units that is indicated as a value obtained by dividing permittivity ($\epsilon$) of a sample by vacuum permittivity ($\epsilon_0$). The vacuum permittivity is almost equivalent to air permittivity, so when being actually measured, the relative permittivity is indicated as a value obtained by dividing permittivity ($\epsilon$) of a sample by permittivity of an empty container, that is, by air permittivity ($\epsilon_{air}$). As a method of measuring relative permittivity of the oil, for example, a permittivity measuring instrument LCR meter "AG-4304" manufactured by Ando Electric Co., Ltd. can be used.

$$\text{Relative permittivity } \epsilon_r = \epsilon/\epsilon_{air}$$

Examples of the oil having a relative permittivity at 20° C. of 3.0 or more include isononyl isononanoate, isodecyl isononanoate, isotridecyl isononanoate, isostearyl myristate, isopropyl myristate, cetyl 2-ethylhexanoate, octyldodecyl myristate, isopropyl palmitate, 2-ethylhexyl palmitate, butyl stearate, hexyl laurate, myristyl myristate, decyl oleate, hexyldecyl dimethyloctanoate, cetyl lactate, myristyl lactate, octyldodecyl lactate, cholesteryl 12-hydroxystearate, phytosteryl 12-hydroxystearate, ethylene glycol di-2-ethylhexanoate, dipentaerythritol fatty acid ester, neopentyl glycol diethylhexanoate, neopentyl glycol dicaprate, pentaerythrityl tetra-2-ethylhexanoate, glyceryl tri-2-ethylhexanoate, glyceryl tri(caprylate/caprate), glyceryl triisostearate, glyceryl tri(caprylate/caprate/myristate/stearate), glyceryl trimyristate, glyceryl tricaprylate, glyceryl tricaprate, trimethylolpropane tri-2-ethylhexanoate, erythrityl triethylhexanoate, dipentaerythrityl tri-polyhydroxystearate, isostearic acid trehalose esters, diglyceryl triisostearate, diglyceryl tetraisostearate, diisostearyl malate, diisobutyl adipate, glycerin adipate/2-ethylhexanoate/stearate) oligoester, hexyl laurate, ethyl laurate, di-2-ethylhexyl sebacate, 2-hexyldecyl myristate, 2-hexyldecyl palmitate, 2-hexyldecyl adipate, diisopropyl sebacate, glycerin triisopalmitate, bis-ethoxydiglycol succinate, neopentyl glycol diisononanoate, (polyglyceryl isostearate-2/dimer dilinoleic acid) copolymer, dimer dilinoleic acid hydrogenated castor oil, propanediol di(caprylate/caprate), propanediol diisostearate, polyglyceryl-6 octacaprylate, bis-ethoxy diglycol cyclohexane-1,4-dicarboxylate, avocado oil, camellia oil, macadamia nut oil, corn oil, sunflower oil, mink oil, olive oil, rapeseed oil, sesame oil, Prunus persica kernel oil, wheat germ oil, sasanqua oil, castor oil, safflower oil, grape seed oil, soybean oil, peanut oil, tea seed oil, rice bran oil, rice germ oil, evening primrose oil, and the like. It is preferable to use one or more kinds selected from these.

Among these, in view of excellent oxidation stability, it is more preferable to use one or more kinds selected from isononyl isononanoate, isodecyl isononanoate, isotridecyl isononanoate, isostearyl myristate, isopropyl myristate, cetyl 2-ethylhexanoate, octyldodecyl myristate, isopropyl palmitate, 2-ethylhexyl palmitate, butyl stearate, hexyl laurate, myristyl myristate, decyl oleate, hexyldecyl dimethyloctanoate, cetyl lactate, myristyl lactate, octyldodecyl lactate, cholesteryl 12-hydroxystearate, phytosteryl 12-hydroxystearate, ethylene glycol di-2-ethylhexanoate, dipentaerythritol fatty acid ester, neopentyl glycol diethylhexanoate, neopentyl glycol dicaprate, pentaerythrityl tetra-2-ethylhexanoate, glyceryl tri-2-ethylhexanoate, glyceryl tri(caprylate/caprate), glyceryl triisostearate, glyceryl tri(caprylate/caprate/myristate/stearate), glyceryl trimyristate, glyceryl tricaprylate, glyceryl tricaprate, trimethylolpropane tri-2-ethylhexanoate, erythrityl triethylhexanoate, dipentaerythrityl tri-polyhydroxystearate, isostearic acid trehalose esters, diglyceryl triisostearate, diglyceryl tetraisostearate, diisostearyl malate, diisobutyl adipate, glycerin (adipate/2-ethylhexanoate/stearate) oligoester, hexyl laurate, ethyl laurate, di-2-ethylhexyl sebacate, 2-hexyldecyl myristate, 2-hexyldecyl palmitate, 2-hexyldecyl adipate, diisopropyl sebacate, glycerin triisopalmitate, bis-ethoxydiglycol succinate, neopentyl glycol diisononanoate, (polyglyceryl isostearate-2/dimer dilinoleic acid) copolymer, dimer dilinoleic acid hydrogenated castor oil, propanediol di(caprylate/caprate), propanediol diisostearate, polyglyceryl-6 octacaprylate, and bis-ethoxy diglycol cyclohexane-1,4-dicarboxylate, and it is even more preferable to use one or more kinds selected from dipentaerythrityl tri-polyhydroxystearate, isostearic acid trehalose esters, diglyceryl triisostearate, diisostearyl maleate, bis-ethoxydiglycol succinate, neopentyl glycol diisononanoate, (polyglyceryl isostearate-2/dimer dilinoleic acid) copolymer, dimer dilinoleic acid hydrogenated castor oil, propanediol di(caprylate/caprate), propanediol diisostearate, polyglyceryl-6 octacaprylate, and bis-ethoxy diglycol cyclohexane-1,4-dicarboxylate.

As the silicone oil, it is preferable to use one or more kinds selected from chain-like polysiloxanes such as dimethyl polysiloxane and methylphenyl polysiloxane, and cyclic polysiloxane such as octamethyl cyclotetrasiloxane, decamethyl cyclopentasiloxane, and dodecamethyl cyclohexasiloxane.

As the component (E), it is also preferable to use hydrogenated lecithin such as hydrogenated soybean phospholipid, hydrogenated rapeseed phospholipid, and hydrogenated egg-yolk phopholipid. If the composition for external use on skin of the present invention contains the hydrogenated lecithin, generation of dirt-like scum caused when the composition is applied to the skin is more markedly suppressed, compared to the case where the composition contains other oils.

Generally, a composition for external use on skin that contains an excessively large amount of the divalent polyol as the component (B), or a composition for external use on skin that contains an excessively large amount of the moisturizer as the component (C) tends to easily generate the dirt-like scum when being applied to the skin. If such a composition for external use on skin further contains hydrogenated lecithin or a surfactant, generation of the scum can be further reduced. For example, when the composition for external use on skin of the present invention further contains a large amount (for example, 50% by mass or more) of the divalent polyol as the component (B) in addition to the water-soluble polymer as the component (A) and water as the component (D), if the hydrogenated lecithin as the component (E) or the surfactant as a component (F) is further added thereto, generation of the dirt-like scum caused when the composition is applied can be more markedly suppressed. In addition, when the composition for external use on skin of the present invention further contains a large amount (for example, 30% by mass or more) of the moisturizer as the component (C) in addition to the water-soluble polymer as the component (A) and water as the component (D), if the hydrogenated lecithin as the component (E) or the surfactant as the component (F) is further added thereto, generation of the dirt-like scum caused when the composition is applied can be more markedly suppressed.

In the related art, it is known that mixing in oil can reduce stickiness of a moisturizer. However, when oil is mixed in, it is very difficult to stably maintain the emulsified state. Contrary to this, if the composition for external use on skin further contains the moisturizer as the component (C) and the oil as component (E) in addition to the water-soluble polymer as the component (A), the divalent polyol as the component (B), and water as the component (D), even when practically no surfactant is mixed in, it is possible to stably maintain the emulsified state without diminishing the effect of suppressing stickiness of the moisturizer. That is, the composition for external use on skin of the present invention containing the water-soluble polymer as the component (A), the divalent polyol as the component (B), the moisturizer as the component (C), water as the component (D), and the oil as the component (E) is an oil-in-water type emulsion composition that further suppresses the stickiness of the moisturizer and is markedly excellent in emulsion stability.

Even when not having a surfactant mixed in, the composition for external use on skin of the present invention is markedly excellent in emulsion stability when the oil as the component (E) is mixed in. Furthermore, as described above, it is preferable that compositions for external use on skin such as cosmetics have as small an amount of a surfactant mixed in as possible in terms of safety. Accordingly, when the composition for external use on skin of the present invention is used for cosmetics, preferably practically no surfactant is mixed in, and when the surfactant is mixed in, the smaller the amount mixed in, the more preferable.

The composition for external use on skin of the present invention can further contain a surfactant as the component (F). For example, the composition for external use on skin of the present invention can contain 0.0001% by mass to 60% by mass of the surfactant as the component (F).

In the present invention, as the surfactant as the component (F), an anionic surfactant, a cationic surfactant, an amphoteric surfactant, and a nonionic surfactant can be used alone or used in combination of two or more kinds thereof. In the present invention, emulsion stability is improved by agar having a weight average molecular weight of 10000 to 60000 and xanthan gum, and the type of the surfactant used as an emulsifier is not limited. However, examples of the surfactant particularly include the following.

Examples of the anionic surfactant include fatty acid soaps such as basis materials for soaps, sodium laurate, potassium laurate, sodium palmitate, potassium palmitate, and potassium myristate, higher alkyl sulfuric acid ester salts such as sodium lauryl sulfate, potassium lauryl sulfate, and sodium laureth sulfate, alkyl ether sulfuric acid ester salts such as POE-lauryl sulfate triethanolamine (TEA laureth sulfate) and sodium POE-lauryl sulfate, N-acylsarcosinate such as sodium lauroyl sarcosine, higher fatty acid amide sulfonic acid salts such as sodium N-myristoyl-N-methyltaurine, sodium coconut oil fatty acid methyl taurate, and sodium lauryl methyl taurate, phosphoric acid ester salts such as POE-oleyl ether sodium phosphate and POE-stearyl ether phosphoric acid, sulfosuccinic acid salts such as sodium di-2-ethylhexyl sulfosuccinate, sodium monolauroyl monoethanolamide polyoxyethylene sulfosuccinate, and sodium lauroyl polypropylene glycol sulfosuccinate, alkylbenzene sulfonic acid salts such as sodium linear dodecyl benzenesulfonate, linear dodecyl benzenesulfonate triethanolamine and linear dodecyl benzenesulfonate, N-acyl glutamic acid salts such as monosodium N-lauroyl glutamate, disodium N-stearoyl glutamate, and monosodium N-myristoyl-L-glutamate, higher fatty acid ester sulfuric acid ester salts such as hardened coconut oil fatty acid sodium glycerin sulfate, sulfated oil such as Turkey-red oil, POE-alkyl ether carboxylic acid, POE-alkyl allyl ether carboxylic acid salt, α-olefin sulfonic acid salt, higher fatty acid ester sulfonic acid salt, secondary alcohol sulfuric acid ester salt, higher fatty acid alkylolamide sulfuric acid ester salt, sodium lauroyl monoethanolamide succinate, di-triethanolamine N-palmitoyl aspartate, sodium casein, potassium cocoyl glycine, sodium lauroyl glutamate, and the like.

Examples of the cationic surfactant include alkyl trimethyl ammonium salts such as stearyl trimethyl ammonium chloride and lauryl trimethyl ammonium chloride, dialkyl dimethyl ammonium salts such as distearyl dimethyl ammonium chloride, alkyl pyridinium salts such as poly(N,N-dimethyl-3,5-methylenepiperidinium) chloride and cetyl pyridinium chloride, alkyl quaternary ammonium salts, alkyl dimethyl benzyl ammonium salts, alkyl isoquinolinium salts, dialkyl morphonium salts, POE-alkylamine, alkylamine salts, polyamine fatty acid derivatives, amylalcohol fatty acid derivatives, benzalkonium chloride, benzethonium chloride, organic modified clay minerals such as organic modified montmorillonite, and the like.

Examples of the amphoteric surfactant include imidazoline-based amphoteric surfactants such as sodium 2-undecyl-N,N,N-(hydroxyethylcarboxymethyl)-2-imidazoline and a disodium 2-cocoyl-2-imidazoliniumhydroxide-1-carboxyethyloxy salt, alkyl betaines such as 2-heptadecyl-N-carboxymethyl-N-hydroxyethylimidazolinium betaine, lauryl dimethylamino acetate betaine, cocamidopropyl betaine, and lauryl betaine, betaine-based surfactants such as amidobetaine, sulfobetaine, and cocobetaine.

Examples of the nonionic surfactant include POE-sorbitan fatty acid esters such as POE-sorbitan monooleate, POE-sorbitan monostearate and POE-sorbitan tetraoleate, POE-sorbitol fatty acid esters such as POE-sorbitol monolaurate, POE-sorbitol monooleate, POE-sorbitol pentaoleate, and POE-sorbitol monostearate, POE-glycerin fatty acid esters such as POE-glycerin monostearate, POE-glycerin monoisostearate, and POE-glycerin triisostearate, POE-fatty acid esters such as POE-monooleate, POE-distearate, POE-monodioleate, and ethylene glycol distearate, POE-alkyl ethers such as POE-lauryl ether, POE-oleyl ether, POE-stearyl ether, POE-behenyl ether, POE-2-octyl dodecyl ether, and POE-cholestanol ether, Pluronic type surfactants such as Pluronic, POE/POP alkyl ethers such as POE/POP-cetyl ether, POE/POP-2-decyl tetradecyl ether, POE/POP-monobutyl ether, POE/POP-hydrogenated lanolin, and POE/POP-glycerin ether, tetra-POE/tetra-POP-ethylenediamine condensates such as Tetronic, POE-castor oil derivatives or POE-hardened castor oil derivatives such as POE-castor oil, POE-hardened castor oil, POE-hardened castor oil monoisostearate, POE-hardened castor oil triisostearate, POE-hardened castor oil monopyroglutamic acid monoisostearic acid diester, and POE-hardened castor oil maleic acid, POE-beeswax/lanolin derivatives such as POE-sorbitol beeswax, alkanolamides such as coconut oil fatty acid diethanolamide (cocamide DEA), lauric acid monoethanolamide, and fatty acid isopropanolamide, polyglycerin fatty acid esters such as POE-propylene glycol fatty acid ester, POE-alkylamine, POE-fatty acid amide, sucrose fatty acid ester, POE-nonylphenyl formaldehyde condensate, alkyl ethoxy dimethylamine oxide, trioleyl phosphate, polyglyceryl sesquicaprylate, polyglyceryl dicaprylate, polyglyceryl monolaurate, polyglyceryl monostearate, polygyceryl monooleate, polyglyceryl distearate, and polyglyceryl dioleate, modified silicones such as a methyl polysiloxane/cetyl methyl polysiloxane/poly(oxyethylene/oxypropylene)methyl polysiloxane copolymer, sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, penia-2-ethylhexyl acid diglycerol sorbitan, and tetra-2-ethylhexyl acid diglycerol sorbitan, glycerin fatty acid esters such as cotton seed oil glycerin mono fatty acid, glycerin monoerucate, glycerin sesquioleate, glycerin monostearate, acid glycerin pyroglutamate, and glycerin monooleate, polyglycerin fatty acid esters such as diglyceryl monoisostearate, diglyceryl diisostearate, diglyceryl condensed ricinoleate, and tetraglyceryl condensed ricinoleate, propylene glycol fatty acid esters such as propylene glycol monostearate, hardened castor oil derivatives, glycerin alkyl ether, decyl glucoside, and the like.

If the composition for external use on skin of the present invention further contains the surfactant as the component (F) in addition to the water-soluble polymer as the component (A) and water as the component (D), generation of the dirt-like scum caused when the composition is applied to the skin can be more markedly suppressed. In view of the effect of suppressing scum generation, it is more preferable that the composition contain a surfactant that exhibits low solubility in a polyalcohol and stays in a solid state at room temperature, as the component (F). Examples of such a surfactant include surfactants having HLB of 6 to 16. Preferable examples of the surfactant that has HLB of 6 to 16 and stays in a solid state at room temperature include sucrose fatty acid ester, polyglyceryl monostearate, polyglyceryl distearate, sorbitan monopalmitate, glycerin monostearate, POE-glycerin monostearate, POE-distearate, POE-oleyl ether, and the like, and among these, sucrose fatty acid ester is particularly preferable.

When the composition for external use on skin of the present invention contains oil as the component (E), if the surfactant as the component (F) is mixed in, particles of the emulsion becomes finer, whereby emulsion stability is more improved than before the surfactant is mixed in. Accordingly, when the composition for external use on skin of the present invention is used for a cosmetic, an emulsion stabilizing effect is sufficiently obtained by mixing in 5% by mass or less of the surfactant as the component (F) based on the component (E). The emulsion stabilizing effect is obtained even when a higher amount of the surfactant is mixed in, but this is undesirable since a concern over safety is caused when the composition is applied to the skin.

Specifically, when the composition for external use on skin of the present invention is used for a cosmetic, if the composition for external use on skin of the present invention further contains the surfactant as the component (F), the composition can contain 0.0001% by mass to 2% by mass, preferably 0.0005% by mass to 2% by mass, and more preferably 0.0005% by mass to 1% by mass of the surfactant.

The composition for external use on skin of the present invention can contain powder as a component (H). For example, the composition for external use on skin of the present invention can contain 5% by mass to 60% by mass, preferably 5% by mass to 50% by mass, more preferably 5% by mass to 40% by mass, and most preferably 5% by mass to 30% by mass of the powder as the component (H).

The composition for external use on skin of the present invention that contains the water-soluble polymer as the component (A) as an essential component is also excellent in storage stability of the powder. Moreover, the storage stability of the powder that the composition for external use on skin of the present invention has almost does not depend on the type of the powder and the type of other components mixed in. Consequently, the composition for external use on skin of the present invention that contains the water-soluble polymer as the component (A), water as the component (D), and the powder as the component (H) is excellent in dispersion stability and storage stability of powder.

Examples of the powder usable as the component (H) include pigments such as inorganic and organic pigments, powder components such as talc, and the like. In the present invention and the present specification, the "powder component" refers to powder other than pigments. The powder that is contained as the component (H) in the composition for external use on skin of the present invention may include only a pigment or a powder component or may include both of them. When the powder as the component (H) is contained, the composition for external use on skin of the present invention is preferably a pigment composition containing pigments.

Examples of the pigment include inorganic white pigments such as titanium dioxide and zinc oxide (also including fine particle type titanium dioxide and zinc oxide used as an ultraviolet scattering agent, or surface-coated inorganic white pigments that are obtained by coating the surface of the above with fatty acid soaps such as aluminum stearate and zinc palmitate, fatty acids such as stearic acid, myristic acid, and palmitic acid, or fatty acid esters such as dextrin palmitate); inorganic red pigments such as iron oxide (colcothar) and iron titanate; inorganic brown pigment such as γ-iron oxide; inorganic yellow pigments such as yellow iron oxide and yellow ocher; inorganic black pigments such as black iron oxide, carbon black, and low grade titanium dioxide; inorganic purple pigments such as mango violet and cobalt violet; inorganic green pigments such as chromium oxide, chromium hydroxide, and cobalt titanate; inorganic blue pigments such as navy blue and dark blue; pearl pigments such as titanium dioxide-coated mica, titanium dioxide-coated bismuth oxychloride, titanium dioxide-coated talc, colored titanium dioxide-coated mica, bismuth oxychloride, and fish scales; metallic powder pigments such as aluminum powder and copper powder; organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404; organic pigments of zirconium and barium or aluminum lake, such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1, and the like. These pigments may be used alone, or two or more kinds thereof may be used in combination.

Examples of the powder component include inorganic powder such as talc, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, tungstic acid metal salts, magnesium, silica, zeolite, barium sulfate, baked barium sulfate, (calcined gypsum), calcium phosphate, fluoroapatite, hydroxy apatite, ceramic powder, metal soaps (zinc myristate, calcium palmitate, and aluminum stearate), and boron nitride; organic powder such as polyamide resin powder (nylon powder), polyethylene powder, polymethylmethacrylate powder, polystyrene powder, styrene-acrylic acid copolymer resin powder, benzoguanamine resin powder, polytetrafluoroethylene powder, and cellulose powder, and the like. These powder components may be used alone, or two or more kinds thereof may be used in combination.

These powders may be used after undergoing surface treatment. The surface treatment includes hydrophobic treatment and hydrophilic treatment. Examples of the hydrophobic treatment include treatment performed using silicone compounds such as dimethyl polysiloxane, methyl hydrogen polysiloxane, trimethylsiloxysilicate, (alkyl acrylate/dimethicone) copolymer, and (dimethicone/methicone) copolymer, treatment performed using fluorine compounds such as fluorine-modified silicone, perfluoroalkyl phosphate DEA, and perfluorooctyl triethoxysilane, treatment performed using metal soaps such as zinc laurate, aluminum stearate, and aluminum isostearate, treatment performed using amino acids such as sodium lysine dilauroyl glutamate, lauroyl lysine, sodium lauroyl aspartate, oil treatment using higher fatty acids, higher alcohols, esters, and wax, treatment performed using polymers such as an acrylate copolymer, and treatment performed using silanes such as triethoxycaprylylsilane, and the like. Examples of the hydrophilic treatment include treatment performed using metal oxides such as silica and alumina, treatment performed using polysaccharides such as crystalline cellulose, cellulose, chitosan, and sodium alginate, treatment performed using sodium metaphosphate, treatment performed using methoxy PEG-10 propyl trimethoxysilane, and the like. In the present invention, the pigment to be added as the powder as the component (H) preferably has undergone the surface treatment, more preferably has undergone the hydrophobic treatment, and most preferably has undergone treatment performed using silicone.

For example, if the composition for external use on skin of the present invention that contains 0.1% by mass to 10% by mass of the water-soluble polymer as the component (A), 30% by mass or more of water as the component (D), 0.01% by mass to 64% by mass of the oil as the component (E), and 5% by mass to 60% by mass of the pigment as the component (H) is used as an active ingredient, it is possible to produce an oil-in-water type emulsion cosmetic that exhibits high dispersibility in a pigment, spreads excellently on the skin, is excellently pleasing to the sense of touch, and has excellent safety for the skin. Moreover, for example, if the composition for external use on skin of the present invention that contains 0.1% by mass to 10% by mass of the water-soluble polymer as the component (A), 0.5% by mass to 40% by mass of the divalent polyol as the component (B), 0.001% by mass to 20% by mass of the moisturizer as the component (C), 30% by mass or more of water as the component (D), 0.01% by mass to 40% by mass of the oil as the component (E), and 5% by mass to 60% by mass of the pigment as the component (H) is used as an active ingredient, it is possible to produce a cosmetic such as a foundation that is excellent in both the moisturizing properties and storage stability of the pigment.

A composition that contains the water-soluble polymer as the component (A), water as the component (D), and the powder as the component (H) can be used for various uses other than the external use on skin. For example, a pigment composition that contains the water-soluble polymer as the component (A), water as the component (D), and the pigment as the component (H) can also be used as an active ingredient of ink and coating materials other than the composition for external use on skin such as a cosmetic.

The water-soluble polymer as the component (A) has a high thickening effect on an aqueous surfactant solution. Accordingly, if the water-soluble polymer as the component (A) is mixed in, even when a surfactant having a sufficient concentration is incorporated to produce a cleaning effect, it is possible to realize appropriate viscosity required for a cleaning agent, without using a highly irritating thickener such as an inorganic salt. That is, if a sufficient amount of the surfactant as the component (F) is mixed with the water-soluble polymer as the component (A) and water as the component (D), it is possible to produce a composition for external use on skin that has necessary viscosity, is excellently pleasing to the sense of touch when used, and is excellent as an active ingredient of a cleaning agent.

When the composition for external use on skin of the present invention is used for a cleaning agent, the composition for external use on skin of the present invention can contain 5% by mass to 60% by mass, preferably 5% by mass to 50% by mass, more preferably 5% by mass to 40% by mass, and even more preferably 5% by mass to 35% by mass of the surfactant as the component (F). When the amount of the surfactant mixed is smaller than 5% by mass, functions such as cleaning properties and foaming properties are not easily obtained. When the amount of the surfactant mixed exceeds 60% by mass, there is a concern that the obtained composition may be gelated, which makes it difficult to obtain a stable formulation.

When the composition for external use on skin is used as a cleaning agent composition, as the surfactant usable as the component (F), ionic and nonionic surfactants can be used alone or used in combination of two or more kinds thereof. Among these, by using amphoteric, anionic, and nonionic surfactants, it is possible to obtain a composition for external use on skin that is excellent in safety and is suitable as an active ingredient of a cleaning agent. In the present invention, as the component (F), an ionic surfactant is preferably mixed in, an amphoteric or anionic surfactant is more preferably mixed in, and an amphoteric surfactant is particularly preferably mixed in. If an ionic surfactant is used, it is possible to obtain a cleaning agent composition that more excellently retains foam. Moreover, if an amphoteric surfactant is used, it is possible to further reduce irritating properties of the cleaning agent composition. Examples of both the ionic surfactants (cationic, anionic, and amphoteric surfactants) and the nonionic surfactants include the same surfactants as the compounds exemplified as usable active ingredients of cosmetics, and these components may be used alone or used in combination of two or more kinds thereof.

The composition for external use on skin of the present invention in which a sufficient amount of the surfactant as the component (F) is mixed in can be used for a hypoallergenic shampoo (baby shampoo), a hypoallergenic body shampoo, a cleaning agent for pets, a shampoo, a body shampoo, a facial cleanser, and the like. Among these, the composition can be suitably used for cleaning agents that require hypoallergenicity and high safety, such as a hypoallergenic shampoo (baby shampoo), a hypoallergenic body shampoo, and a cleaning agent for pets.

The composition containing the water-soluble polymer as the component (A), water as the component (D), and a sufficient amount of the surfactant as the component (F) can also be suitably used for various cleaning agents such as a liquid detergent for clothes, a detergent for dishes, and a liquid detergent for washing walls, in addition to the external use on skin.

The composition for external use on skin of the present invention does not exhibit change in viscosity and change in the obtained effect even if a water-soluble ionic substance is mixed in. Accordingly, this composition can contain an active ingredient that dissolves in water and dissociates into ions. Such a water-soluble ionic substance is mixed in an amount of 0.01% by mass to 10% by mass, preferably 0.1% by mass to 8% by mass, and more preferably 0.5% by mass to 5% by mass, as a component (G).

When the water-soluble ionic substance dissolves in water, all or a portion of this substance dissociates into ions. Therefore, these substances are classified into inorganic salts, organic salts, and the like. Examples of the inorganic salts include sodium chloride, potassium chloride, magnesium chloride, sodium sulfate, potassium sulfate, magnesium sulfate, and the like. Examples of the organic salts include citric acid, maleic acid, tartaric acid, salts of these, ascorbic acid and salts thereof, ascorbic acid derivatives and salts thereof, and the like.

Among these, ascorbic acid and salts thereof, and ascorbic acid derivatives and salts thereof are widely known for their antioxidative action and whitening action, so these are very useful for being mixed with an agent for external use on skin. Specific examples of the water-soluble ascorbic acids include ascorbic acid such as L-ascorbic acid and salts of ascorbic acid such as a sodium salt, a potassium salt, a magnesium salt, a calcium salt, a barium salt, an ammonium salt, a monoethanolamine salt, a diethanolamine salt, a triethanolamine salt, a monoisopropanolamine salt, a triisopropanolamine salt, and the like. Examples of the ascorbic acid derivatives include L-ascorbic acid monoesters such as L-ascorbic acid glucoside, L-ascorbic acid-2-phosphoric acid ester, L-ascorbic acid-3-phosphoric acid ester, L-ascorbic acid-6-phosphoric acid ester, L-ascorbic acid-2-polyphosphoric acid ester, and L-ascorbic acid-2-sulfuric acid ester. Examples of the salt of ascorbic acid derivatives include a sodium salt, a potassium salt, a magnesium salt, a calcium salt, a barium salt, an ammonium salt, a monoethanolamine salt, a diethanolamine salt, a triethanolamine salt, a monoisopropanolamine salt, a triisopropanolamine salt, and the like. Among these, it is particularly preferable to use magnesium L-ascorbic acid-2-phosphoric acid ester, sodium L-ascorbic acid-2-phosphoric acid ester, and L-ascorbic acid glucoside.

For the purpose of functional improvement, skin nourishment, preventing quality deterioration, and the like, the composition for external use on skin of the present invention can be optionally mixed appropriately with various components that do not correspond to the above components (A) to (H) and are generally used for a composition for external use on skin, within a range that does not impair the effects of the present invention. Specific examples of such components include naturally occurring water-soluble polymers, semisynthetic water-soluble polymers, synthetic water-soluble polymers, inorganic water-soluble polymers, an ultraviolet absorber, a sequestering agent, lower alcohols, polyalcohols, monosaccharides, oligosaccharides, polysaccharides, amino acids, organic amines, a synthetic resin emulsion, a preservative, a pH adjustor, vitamins, plant extract, an antioxidant, an antioxidation aid, fragrances, and the like. These components may be used alone or used in combination of two or more kinds thereof.

Examples of the naturally occurring water-soluble polymers include plant-based polymers such as gum arabic, tragacanth gum, galactan, guar gum, carob gum, karaya gum, carrageenan, pectin, quince seeds (marmelo), algae colloid (brown algae extract), and starch (rice, corn, potato, and wheat), microorganism-based polymers such as dextran, succinoglucan, and pullulan, and animal-based polymers such as collagen, casein, albumin, and gelatin.

Examples of the semisynthetic water-soluble polymers include starch-based polymers such as carboxymethyl starch and methyl hydroxypropyl starch, cellulose-based polymers such as methyl cellulose, nitrocellulose, methyl hydroxypropyl cellulose, sodium cellulose sulfate, hydroxypropyl cellulose, carboxymethyl cellulose, sodium carboxymethyl cellulose, crystalline cellulose, and cellulose powder, alginic acid-based polymers such as sodium alginate and propylene glycol alginate ester, and the like.

Examples of the synthetic water-soluble polymers include vinyl-based polymers such as polyvinyl alcohol, polyvinyl methyl ether, polyvinyl pyrrolidone, a carboxy vinyl polymer (Carbopol), polyoxyethylene-based polymers such as polyethylene glycol 20,000, 40,000, and 60,000, copolymerized polymers such as polyoxyethylene-polyoxypropylene copolymer, acryl-based polymers such as sodium polyacrylate, polyethyl acrylate, and polyacrylamide, polyethyleneimine, a cation polymer, and the like.

Examples of the inorganic water-soluble polymers include bentonite, magnesium aluminum silicate (Veegum), laponite, hectorite, silicic anhydride, and the like.

Examples of the ultraviolet absorber include benzoic acid-based ultraviolet absorbers such as para-aminobenzoic acid (hereinbelow, abbreviated to PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester; anthranilic acid-based ultraviolet absorbers such as homomenthyl-N-acetyl anthranilate; salicylic acid-based ultraviolet absorbers such as amyl salicylate, menthyl salicylate, homomenthyl salicylate, octyl salicylate, phenyl salicylate, benzyl salicylate, and p-isopropanol phenyl salicylate; cinnamic acid-based ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenyl cinnamate, 2-ethylhexyl-α-cyano-β-phenyl cinnamate, and glyceryl mono-2-ethylhexanoyl-diparamethoxycinnamate; benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methyl benzophenone, 2-hydroxy-4-methoxybenzophenone-5-sulfonic acid salt, 4-phenyl benzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methyl benzoxazole, 2,2'-hydroxy-5-methylphenyl benzotriazole, 2-(2'-hydroxy-5'-t-octylphenyl)benzotriazole, 2-(2'-hydroxy-5'-methylphenyl)benzotriazole, dibenzalazine, dianisoyl methane, 4-methoxy-4'-t-butyl dibenzoyl methane, 5-(3,3-dimethyl-2-norbonylidene)-3-pentan-2-one, and 2,4,6-trianilino-p-(carbo-2'-ethylhexyl-1'-oxy)1,3,5-triazine, 4-tert-butyl-4'-methoxybenzoyl methane, and the like. These ultraviolet absorbers may be used alone or used in combination of two or more kinds thereof.

Among the ultraviolet absorbers, diethylaminohydroxybenzoyl hexyl benzoate (for example, a product named "Uvinul A+" manufactured by BASF), ethylhexyl triazine (for example, a product named "Uvinul T-150, manufactured by BASF), t-butyl methoxybenzoyl methane (for example, a product named "Parsol 1789" manufactured by DSM), bis-ethylhexyloxyphenol methoxyphenyl triazine (for example, a product named "Tinosorb S" manufactured by Ciba), diethylhexyl butamidotriazone (for example, a product named "Uvasorb HEB 3V" manufactured by Sigma-Aldrich Co., LLC), oxybenzone-3 (for example, a product named "Uvinul M-40" manufactured by BASF), and the like are known as ultraviolet absorbers that do not easily dissolve in silicone oil. If oil in which these ultraviolet absorbers are dissolved is compatible with silicone oil, solubility of the ultraviolet absorber is lowered, whereby precipitation or the like is caused in some cases. On the other hand, the composition for external use on skin of the present invention stably maintains the emulsified state even in a state where the oil in which the ultraviolet absorber is dissolve is incompatible with silicone oil, so precipitation of the ultraviolet absorber can be inhibited.

Examples of the sequestering agent include disodium edetate, an edetic acid salt, hydroxyethane diphosphonate, and the like. The sequestering agent may be used alone or used in combination of two or more kinds thereof.

Examples of the lower alcohols include methanol, ethanol, propanol, isopropanol, isobutyl alcohol, t-butyl alcohol, and the like.

Examples of the monosaccharide include triose such as D-glyceraldehyde and dihydroxyacetone, tetrose such as D-erythrose, D-erythrulose, and D-threose, pentose such as L-arabinose, D-xylose, L-lyxose, D-arabinose, D-ribose, D-ribulose, D-xylulose, and L-xylulose, hexose such as D-glucose, D-talose, D-psicose, D-galactose, D-fructose, L-galactose, L-mannose, and D-tagatose, heptose such as aldoheptose and heptulose, octose such as octulose, deoxy sugars such as 2-deoxy-D-ribose, 6-deoxy-L-galactose, and 6-deoxy-L-mannose, amino sugars such as D-glucosamine, D-galactosamine, sialic acid, aminouronic acid, and muramic acid, uronic acid such as D-glucuronic acid, D-mannuronic acid, L-guluronic acid, D-galacturonic acid, and L-iduronic acid, and the like.

Examples of the oligosaccharide include sucrose, gentianose, umbelliferose, lactose, planteose, isolignoses, α,α-trehalose, raffinose, lignoses, umbilicine, stachyose verbascoses, and the like.

Examples of the polysaccharide include cellulose, chondroitin sulfate, dextrin, glucomannan, chitin, galactan, dermatan sulfate, glycogen, gum arabic, heparan sulfate, tragacanth gum, keratan sulfate, chondroitin, mucoitin sulfate, guar gum, dextran, kerato sulfate, locust bean gum, succinoglucan, charonic acid, and the like.

Examples of the amino acid include neutral amino acids such as threonine and cysteine and basic amino acids such as hydroxylysine. Examples of the amino acid derivatives include sodium acyl sarcosine, (sodium lauroyl sarcosine), an acyl glutamic acid salt, sodium acyl β-alanine, glutathione, and the like.

Examples of the organic amines include monoethanolamine, diethanolamine, triethanolamine, morpholine, triisopropanolamine, 2-amino-2-methyl-1,3-propanediol, 2-amino-2-methyl-1-propanol, and the like.

Examples of the synthetic resin emulsion include alkyl acrylate copolymer emulsion, alkyl methacrylate polymer emulsion, alkyl acrylate copolymer emulsion, alkyl methacrylate copolymer emulsion, acrylic acid-alkyl acrylate copolymer emulsion, methacrylic acid-alkyl methacrylate copolymer emulsion, alkyl acrylate-styrene copolymer emulsion, alkyl methacrylate-styrene copolymer emulsion, vinyl acetate polymer emulsion, polyvinyl acetate emulsion, vinyl acetate-containing copolymer emulsion, vinyl pyrrolidone-styrene copolymer emulsion, silicone-containing copolymer emulsion, and the like. These synthetic resin emulsions may be used alone or used in combination of two or more kinds thereof.

Examples of the preservative include methylparaben, ethylparaben, butylparaben, phenoxyethanol, and the like. These preservatives may be used alone or used in combination of two or more kinds thereof.

Examples of the pH adjustor include edetic acid, disodium edetate, citric acid, sodium citrate, sodium hydroxide, potassium hydroxide, triethanolamine, and the like. These pH adjustors may be used alone or used in combination of two or more kinds thereof.

Examples of the vitamins include vitamin A, vitamin B1, vitamin B2, vitamin B6, vitamin E, vitamin K, and derivatives of these, pantothenic acid and derivatives thereof, biotin, and the like.

Examples of the plant extract include aloe vera, witch hazel, hamamelis, cucumber, lemon, lavender, rose, and the like.

Examples of the antioxidant include oil-soluble vitamin C derivatives, tocopherols and derivatives thereof, and salts thereof, dibutylhydroxy toluene, butylhydroxy anisole, gallic acid esters, and the like. These antioxidants may be used alone or used in combination of two or more kinds thereof.

Examples of the antioxidation aid include phosphoric acid, citric acid, maleic acid, malonic acid, succinic acid, fumaric acid, cephalin, hexametaphosphate, phytic acid, ethylenediaminetetra acetic acid, and the like.

As a method of obtaining the composition for external use on skin of the present invention, the water-soluble polymer as the component (A) is dissolved in all or a portion of water as the component (D) by heating, and other arbitrary components to be mixed, such as components (B), (C), (E), (F), (G), and (H), are added thereto and homogenized under stirring with a disper, a homomixer, a propeller, or the like. Thereafter, the mixture is cooled to room temperature while being stirred continuously, whereby the composition for external use on skin can be obtained. The above components may be added in any order. Moreover, the components (A), (B), (C), (E), (F), (G), and (H) and other arbitrary components may be mixed all together and dissolved by heating, and the mixture is cooled to room temperature while being stirred continuously, whereby the composition for external use on skin can be obtained. The heating temperature is preferably 80° C. or higher, more preferably 80° C. to 95° C., and even more preferably 85° C. to 95° C.

Unstable components and the like which may be altered at a high temperature are added after the solution of the component (A) is cooled, whereby the composition for external use on skin can be obtained. In addition, when an emulsion is prepared by adding the oil as the component (E), techniques such as dispersion emulsification, phase-inversion emulsification, and D-phase emulsification may be used. At this time, the component (A) may be added in advance to a water phase during emulsification, or preliminary dissolution can be performed in advance on an aqueous solution of the component (A) having a high concentration, and this solution can be emulsified and then appropriately added.

For example, the water-soluble polymer as the component (A) is dissolved in whole or a portion of water as the component (D) by heating, and the powder as the component (H), preferably a pigment (and optionally other components) is added thereto and homogenized under stirring by using a disper, a homomixer, a propeller, or the like. Subsequently, the mixture is cooled to room temperature while being stirred continuously, whereby a powder dispersion composition that is excellent in dispersion stability of the powder can be obtained. If the powder dispersion composition that is obtained by dispersing in advance a pigment in the water-soluble polymer as the component (A) is used as a raw material of a cosmetic and the like, it is possible to more stably disperse the powder in the cosmetic and the like, compared to a case where only powder such as a pigment is independently used as a raw material of a cosmetic and the like. For example, if a powder dispersion composition containing 0.1% by mass to 10% by mass of the water-soluble polymer as the component (A), 30% by mass or more of water as the component (D), and 5% by mass to 60% by mass of the powder as the component (H) is produced and then mixed with other cosmetic raw materials, it is possible to produce a cosmetic that is excellent in powder dispersion stability.

When the composition for external use on skin of the present invention is produced, if the water-soluble polymer as the component (A) is dissolved in all or a portion of water as the component (D) by heating, and then the obtained water-soluble polymer solution is held at 85° C. to 95° C. for 50 minutes or longer, it is possible to further enhance the effect of ameliorating the sliminess that is caused by the water-soluble polymer as the component (A) when the composition is applied to the skin. The water-soluble polymer solution held at 85° C. to 95° C. for 50 minutes or longer may be a solution including only the water-soluble polymer as the component (A) and water as the component (D), or may be a solution further containing other arbitrary components having high thermal resistance (that is, components less likely to deteriorate by heating). However, the solution is preferably a solution including only the water-soluble polymer as the component (A) and water as the component (D). In addition, during the heat retaining treatment in which the water-soluble polymer solution is kept at 85° C. to 95° C., the water-soluble polymer solution may be stirred or left to stand. Moreover, during the heat retaining treatment, other arbitrary components to be mixed may be added appropriately.

According to the composition for external use on skin of the present invention that contains the water-soluble polymer as the component (A) and water as the component (D), by performing the heat retaining treatment, it is possible to obtain a composition for external use on skin that further suppresses sliminess caused when the composition is applied to the skin, compared to a case where the heat retaining treatment is not performed. Here, when the composition for external use on skin of the present invention contains the moisturizer as the component (C), in order to obtain a sufficient sliminess ameliorating effect, the composition preferably contains the divalent polyol as the component (B) in addition to the components (A), (C), and (D).

The composition for external use on skin of the present invention is used as a raw material of cosmetics, quasi-drugs, drugs, cleaning agents, and the like. Particularly, the composition for external use on skin of the present invention can be suitably used for cosmetics or cleaning agents. When the composition for external use on skin of the present invention is used as a raw material of cosmetics or cleaning agents, the proportion of the composition for external use on skin of the present invention contained in the cosmetics or cleaning agents is preferably 10% by mass to 90% by mass.

The composition for external use on skin of the present invention can be used as a premixed composite raw material, or can be contained in cosmetics, quasi-drugs, drugs, cleaning agents, and the like as one of composite raw materials. Particularly, the composite raw material including the composition for external use on skin of the present invention can be suitably mixed with cosmetics or cleaning agents such as a hypoallergenic shampoo (baby shampoo), a hypoallergenic body shampoo, and a cleaning agent for pets.

The form of the cosmetic containing the composition for external use on skin of the present invention is not particularly limited. However, the composition can be suitably used particularly for an emulsion, a cream, an essence, a toner, an ointment, a pack, and the like. In addition, the form of the cleaning agent containing the composition for external use on skin of the present invention is not particularly limited. However, the composition can be suitably used particularly for a liquid cleaning agent, a cream-type cleaning agent, a gel-type cleaning agent, a solid cleaning agent, and the like.

For the purposes of functional improvement, skin nourishment, preventing quality deterioration, and the like, the cosmetics or cleaning agents containing the composition for external use on skin of the present invention can be optionally mixed appropriately with various components that are generally used for cosmetics or cleaning agents, within a range that does not impair the effects of the present invention. Specific examples of the components include surfactants such as nonionic, anionic, cationic, and amphoteric surfactants, powder components such as inorganic and organic pigments, iron oxide, and talc, naturally occurring water-soluble polymers, semisynthetic water-soluble polymers, synthetic water-soluble polymers, inorganic water-soluble polymers, ultraviolet absorber, sequestering agent, lower alcohol, monosaccharides, oligosaccharides, polysaccharides, amino acid, organic amines, synthetic resin emulsion, salts, preservative, pH adjustor, vitamins, plant extract, antioxidant, antioxidation aid, fragrances, and the like. Examples of these components include the same ones as described above, and these components may be used alone or used in combination of two or more kinds thereof.

The cosmetics or cleaning agents containing the composition for external use on skin of the present invention can be produced by methods of producing cosmetics or cleaning agents known in the related art. In addition, a cosmetic or a cleaning agent containing any one or several kinds of the components (A) and (D) (optionally, the components (B), (C), and (E) to (H) as well) exemplified for the composition for external use on skin of the present invention may be produced, and then other components or a cosmetic raw material or a cleaning agent raw material containing those other components may be added to the cosmetic or the cleaning agent to complete the cosmetic or the cleaning agent.

The component (A) in the present invention can be used independently as an emulsifier. That is, an emulsifier including the component (A) can be added to various products in addition to an agent for external use on skin. For example, the emulsifier including the component (A) can be suitably used as an industrial emulsifier used for ink, coating materials, automobile polishing agents, agrochemical emulsions, emulsion fuels, emulsification polymerization reaction, and the like.

For example, though widely used for the automobile polishing agent, the fluorine-based oil has a problem of having poor compatibility with other oils. In addition, though a surfactant is used for stabilizing the emulsified state, it is difficult to emulsify the fluorine-based oil by using a surfactant used generally, so a fluorosurfactant has to be used. If the automobile polishing agent is mixed with a fluorine-based oil and the emulsifier including the component (A), it is possible to produce an automobile polishing agent excellent in emulsion stability without using a surfactant. Furthermore, since a coating film, which is formed by coating the automobile polishing agent obtained by mixing the emulsifier including the component (A) instead of a surfactant, is not mixed with a surfactant, affinity of the coating film with water is lowered, so durability of the coating film is improved.

EXAMPLES

Hereinbelow, examples and comparative examples of the present invention will be described to explain the present invention in more detail, but the present invention is not limited thereto.

Production Example 1

Measuring Weight Average Molecular Weight and Number Average Molecular Weight of Agar The weight average molecular weight and number average molecular weight of agar was measured according to gel permeation chromatography based on HPLC. 0.3 g of agar was dissolved in 200 mL of distilled water at 95° C. to 97° C., followed by cooling to 50° C., thereby obtaining a sample for measurement. By using LC-10AT VP and RID-10A manufactured by Shimadzu Corporation, a differential refractometer as a detector, TOSOH TSK-GEL for HPLC and TSK-GEL GMPWXL manufactured by TOSOH CORPORATION as columns, and using 0.1 M sodium nitrate as a developing solvent, the measurement was performed at a constant temperature and at a flow rate of 1.0 ml/min. In order to determine the weight average molecular weight of agar, pullulan (for example, Shodex STANDARD P-82) of which the weight average molecular weight was known was used as a standard sample. Shodex STANDARD P-82 (0.015 g) was dissolved in 10 ml of distilled water, and the measurement was performed by gel permeation chromatography based on HPLC under the same conditions.

(Measuring 1.5% Gel Strength of Agar)

(1) Measurement instrument texture analyzer (manufactured by EKO INSTRUMENTS Co., Ltd.) plunger: cylindrical plunger, area=1 cm$^2$, sample stage lifting rate: 20 mm/min (2) Preparing Sample 1) 3.0 g of an agar sample was weighed and put into a tared container (a capacity of 0.5 L), and 50 mL of deionized water was added thereto, thereby causing the sample to sufficiently absorb water.

2) Warm deionized water was added thereto to adjust the amount of the content to be about 210 g, and the mixture was dissolved by being heated for 15 minutes in a hot water bath.

3) The content was adjusted to be 200.0 g, and the mixture was caused to flow into glass container having an inner diameter of 49 mm and a depth of 57 mm where a tape was wound around the upper portion thereof.

4) The resultant was left to cool at room temperature for an hour, and the container was capped and left to stand overnight in a constant temperature chamber at 20° C.

(3) The tape was removed from the glass container, and then jelly around the periphery of the container that stuck out of the container was cut with a cutter and discarded. In order to measure the strength of the cut surface of the obtained jelly, the texture analyzer was used, and a force applied per unit area of the plunger at the moment when the jelly broke was measured and taken as 1.5% gel strength.

(Measuring 1.5% Gel Push-Out Load of Agar)

A cylindrical container (including a hole having a diameter of 3 mm that was formed in the central portion of the bottom of the container and blocked with a tape) made of acryl that had an inner diameter of 50 mm and a height of 110 mm and was attached to a texture analyzer (manufactured by EKO INSTRUMENTS Co., Ltd.) was filled with 100 g of a 1.5% by weight agar solution, followed by gelation at 20° C. for 18 hours. The tape was removed from the hole, and pressure was applied from the top of the gel by using a plunger having a diameter of 49 mm (advancing rate of 20 mm/min, measurement temperature of 20° C.), whereby the load at the time when the gel broke and flowed out of the hole was measured using the texture analyzer.

TABLE 1

| List of Physical Properties of Agar | | | | | | |
|---|---|---|---|---|---|---|
| | | Weight average molecular weight (Mw) | Number average molecular weight (Mn) | Mw/Mn | 1.5% gel strength | 1.5% gel push-out load |
| Agar 1 | Ena (low-molecular weight agar) (manufactured by Ina Food Industry Co., Ltd.) | 43000 | 8800 | 4.9 | 10 g/cm$^2$ | 170 g |

TABLE 1-continued

List of Physical Properties of Agar

|  |  | Weight average molecular weight (Mw) | Number average molecular weight (Mn) | Mw/Mn | 1.5% gel strength | 1.5% gel push-out load |
|---|---|---|---|---|---|---|
| Agar 2 | Ultra agar AX-30 (manufactured by Ina Food Industry Co., Ltd.) | 68000 | 7900 | 8.6 | 30 g/cm$^2$ | 1520 g |
| Agar 3 | Ultra agar AX-100 (manufactured by Ina Food Industry Co., Ltd.) | 79000 | 9000 | 8.8 | 100 g/cm$^2$ | 2000 g or more |
| Agar 4 | Agar S-7 (manufactured by Ina Food Industry Co., Ltd.) | 290000 | 48000 | 6.0 | 730 g/cm$^2$ | 2000 g or more |

Examples 1 to 18 and Comparative Examples 1 to 8

Production Method

According to the compounding shown in Tables 2 to 4, all components were weighed and put in a beaker, mixed and dissolved by being heated at 80° C. to 95° C., and then the resultant was cooled slowly while being stirred with a table disper mixer at 2000 rpm. The resultant was deaerated under reduced pressure, and the thus obtained composition for external use on skin was taken as a sample.

(Feeling During Use)

The respective compositions for external use on skin were applied to the whole face of a panel consisting of 15 members after the face was washed, and the feeling during use was surveyed by answers to a questionnaire and evaluated according to the following criteria. The "feeling of stickiness", "spreadability on skin", "dirt generation", and "feeling of sliminess" were used to evaluate the feeling during use in application. The "re-lubricating property of fingers" was used to evaluate feeling of slipperiness that was caused when fingers used for the application of the composition for external use on skin were wet with several drops of water after the fingers were dried. The evaluation criteria of the respective items are shown below.

[Feeling of Stickiness]

A: 12 or more people answered that the composition was not sticky.

B: 8 to 11 people answered that the composition was not sticky.

C: 4 to 7 people answered that the composition was not sticky.

D: 3 or less people answered that the composition was not sticky.

[Spreadability on Skin]

A: 12 or more people answered that the composition could be easily spread on skin and feeling during use was excellent.

B: 8 to 11 people answered that the composition could easily be spread on skin and feeling during use was excellent.

C: 4 to 7 peoples answered that the composition could be easily spread on skin and feeling during use was excellent.

D: 3 or less people answered that answered the composition could be easily spread on skin and feeling during use was excellent.

[Dirt Generation]

A: 12 or more people answered that dirt-like scum was not generated and feeling during use was excellent.

B: 8 to 11 people answered that dirt-like scum was not generated and feeling during use was excellent.

C: 4 to 7 people answered that dirt-like scum was not generated and feeling during use was excellent.

D: 3 or less people answered that dirt-like scum was not generated and feeling during use was excellent.

[Feeling of Sliminess]

A: 12 or more people answered that the composition was not slimy.

B: 8 to 11 people answered that the composition was not slimy.

C: 4 to 7 people answered that the composition was not slimy.

D: 3 or less people answered that the composition was not slimy.

[Re-Lubricating Property of Fingers]

A: 12 or more people answered that were not bothered with slipperiness.

B: 8 to 11 people answered that that were not bothered with slipperiness.

C: 4 to 7 people answered that that were not bothered with slipperiness.

D: 3 or less people answered that that were not bothered with slipperiness.

(Storage Stability)

After the composition was stored at 50° C. for a month, a degree of water separation, oil separation, and creaming was visually observed and evaluated according to the following criteria.

A: Water separation, oil separation, and creaming were not observed.

B: Any of water separation, oil separation, and creaming was observed slightly.

C: Any of water separation, oil separation, and creaming was observed clearly.

D: Any of water separation, oil separation, and creaming was observed markedly.

TABLE 2

Examples 1 to 11

(% by mass)

| | Example | | | | | | | | | | |
|---|---|---|---|---|---|---|---|---|---|---|---|
| | 1 | 2 | 3 | 4 | 5 | 6 | 7 | 8 | 9 | 10 | 11 |
| Agar 1 | 0.9 | 0.9 | 0.9 | 0.9 | 0.9 | 0.9 | 0.9 | 0.6 | 1.2 | 0.2 | 3.0 |
| Xanthan gum*[1] | 0.6 | 0.6 | 0.6 | 0.6 | 0.6 | 0.6 | 0.6 | 0.9 | 0.3 | 0.1 | 2.0 |
| Propylene glycol | 10 | 10 | 10 | 10 | 10 | 10 | 10 | 10 | 10 | 10 | 10 |
| Sodium hyaluronate | 0.1 | — | — | — | — | — | 0.1 | 0.1 | 0.1 | 0.1 | 0.1 |
| Sodium pyrrolidone carboxylate | — | 4 | — | — | — | — | 2 | 2 | 2 | 2 | 2 |
| Glycerin | — | — | 10 | — | — | 10 | 4 | 4 | 4 | 4 | 4 |
| Diglycerin | — | — | — | 10 | — | — | 4 | 4 | 4 | 4 | 4 |
| Decaglycerin | — | — | — | — | 10 | — | 2 | 2 | 2 | 2 | 2 |
| Methylparaben | 0.2 | 0.2 | 0.2 | 0.2 | 0.2 | 0.2 | 0.2 | 0.2 | 0.2 | 0.2 | 0.2 |
| Neopentyl glycol dicaprate*[2] | — | — | — | — | — | 10 | 10 | 10 | 10 | 10 | 10 |
| Purified water | 88.2 | 84.3 | 78.3 | 78.3 | 78.3 | 68.3 | 66.2 | 66.2 | 66.2 | 67.4 | 62.7 |
| Total | 100 | 100 | 100 | 100 | 100 | 100 | 100 | 100 | 100 | 100 | 100 |
| Feeling of stickiness | A | A | A | A | A | A | A | A | A | A | A |
| Spreadability on skin | A | A | A | A | A | A | A | A | A | A | A |
| Dirt generation | A | A | A | A | A | A | A | A | A | A | B |
| Feeling of sliminess | A | A | A | A | A | A | A | B | A | A | A |
| Re-lubricating property of fingers | A | A | A | A | A | A | A | A | A | A | A |
| Storage stability | A | A | A | A | A | A | A | A | B | B | A |

*[1]"NOMCORT ZZ" (manufactured by The Nisshin OilliO Group, Ltd.)
*[2]"ESTEMOL N-01" (manufactured by The Nisshin OilliO Group, Ltd.) (relative permittivity 3.4)

TABLE 3

Comparative Examples 1 to 8

(% by mass)

| | Comparative Example | | | | | | | |
|---|---|---|---|---|---|---|---|---|
| | 1 | 2 | 3 | 4 | 5 | 6 | 7 | 8 |
| Agar 1 | 1.5 | — | 0.9 | — | — | — | 0.45 | 1.35 |
| Agar 2 | — | — | — | 0.9 | — | — | — | — |
| Agar 3 | — | — | — | — | 0.9 | — | — | — |
| Agar 4 | — | — | — | — | — | 0.9 | — | — |
| Xanthan gum*[1] | — | 1.5 | 0.6 | 0.6 | 0.6 | 0.6 | 1.05 | 0.15 |
| Propylene glycol | 10 | 10 | — | 10 | 10 | 10 | 10 | 10 |
| Sodium hyaluronate | 0.1 | 0.1 | 0.1 | 0.1 | 0.1 | 0.1 | 0.1 | 0.1 |
| Sodium pyrrolidone carboxylate | 2 | 2 | 2 | 2 | 2 | 2 | 2 | 2 |
| Glycerin | 4 | 4 | 4 | 4 | 4 | 4 | 4 | 4 |
| Diglycerin | 4 | 4 | 4 | 4 | 4 | 4 | 4 | 4 |
| Decaglycerin | 2 | 2 | 2 | 2 | 2 | 2 | 2 | 2 |
| Methylparaben | 0.2 | 0.2 | 0.2 | 0.2 | 0.2 | 0.2 | 0.2 | 0.2 |
| Neopentyl glycol dicaprate*[2] | 10 | 10 | 10 | 10 | 10 | 10 | 10 | 10 |
| Purified water | 66.2 | 66.2 | 76.2 | 66.2 | 66.2 | 66.2 | 66.2 | 66.2 |
| Total | 100 | 100 | 100 | 100 | 100 | 100 | 100 | 100 |
| Feeling of stickiness | D | D | D | D | D | D | D | D |
| Spreadability on skin | C | B | A | D | D | D | C | C |
| Dirt generation | B | C | C | D | D | D | C | B |

TABLE 3-continued

Comparative Examples 1 to 8

| | Comparative Example | | | | | | | | (% by mass) |
|---|---|---|---|---|---|---|---|---|---|
| | 1 | 2 | 3 | 4 | 5 | 6 | 7 | 8 | |
| Feeling of sliminess | A | D | C | B | C | C | D | A | |
| Re-lubricating property of fingers | B | D | B | D | D | D | C | B | |
| Storage stability | D | C | C | D | D | D | B | D | |

*[1]"NOMCORT ZZ" (manufactured by The Nisshin OilliO Group, Ltd.)
*[2]"ESTEMOL N-01" (manufactured by The Nisshin OilliO Group, Ltd.) (relative permittivity 3.4)

TABLE 4

Examples 12 to 18

| | Example | | | | | | | (% by mass) |
|---|---|---|---|---|---|---|---|---|
| | 12 | 13 | 14 | 15 | 16 | 17 | 18 | |
| Agar 1 | 0.9 | 0.9 | 0.9 | 0.9 | 0.9 | 0.9 | 0.6 | |
| Xanthan gum*[1] | 0.6 | 0.6 | 0.6 | 0.6 | 0.6 | 0.6 | 0.9 | |
| 1,3-Propanediol | 10 | — | — | — | — | — | — | |
| 1,3-Butylene glycol | — | 10 | — | — | — | — | — | |
| 3-Methyl-1,3-butanediol | — | — | 10 | — | — | — | — | |
| 1,2-Pentanediol | — | — | — | 4 | — | — | — | |
| Dipropylene glycol | — | — | — | — | 10 | — | — | |
| 1,2-Hexanediol | — | — | — | — | — | 2 | — | |
| Hexylene glycol | — | — | — | — | — | — | 2 | |
| Glycerin | 10 | 10 | 10 | 10 | 10 | 10 | 10 | |
| Methylparaben | 0.2 | 0.2 | 0.2 | 0.2 | 0.2 | 0.2 | 0.2 | |
| Neopentyl glycol dicaprate*[2] | 10 | 10 | 10 | 10 | 10 | 10 | 10 | |
| Water | 68.3 | 68.3 | 68.3 | 74.3 | 68.3 | 76.3 | 76.3 | |
| Total | 100 | 100 | 100 | 100 | 100 | 100 | 100 | |
| Feeling of stickiness | A | B | A | A | A | A | B | |
| Spreadability on skin | A | A | A | A | A | A | A | |
| Dirt generation | A | A | A | A | A | A | A | |
| Feeling of sliminess | A | A | A | A | A | A | A | |
| Re-lubricating property of fingers | A | A | A | A | A | A | A | |
| Storage stability | A | A | A | A | A | A | A | |

*[1]"NOMCORT ZZ" (manufactured by The Nisshin OilliO Group, Ltd.)
*[2]"ESTEMOL N-01" (manufactured by The Nisshin OilliO Group, Ltd.) (relative permittivity 3.4)

As result, all of the compositions for external use on skin of Examples 1 to 18 according to the present invention were excellent since they did not impart a feeling of stickiness and sliminess, were spread excellently on the skin, did not generate the dirt-like scum, and did not make fingers slippery even when fingers came into contact with moisture again. Furthermore, even being stored at 50° C. for a month, these compositions for external use on skin did not produce a liquid residue and showed excellent emulsion stability of oil, that is, showed excellent storage stability.

On the other hand, all of the composition for external use on skin (Comparative Example 1) not mixed with xanthan gum and the composition for external use on skin (Comparative Example 8) in which the proportion of xanthan gum mixed was lower than the range of the present invention imparted a feeling of stickiness, were not sufficiently spread on the skin, and showed poor storage stability.

The composition for external use on skin (Comparative Example 2) not mixed with the low-molecular weight agar imparted a feeling of stickiness and sliminess, generated the dirt-like scum, made fingers slippery when the fingers came into contact with moisture again, and showed insufficient storage stability. In addition, all of the compositions for external use on skin (Comparative Example 4 to 6) using agar having a molecular weight exceeding the range of the present invention imparted a feeling of stickiness, were not excellently spread on the skin, generated scum, made fingers slippery when the fingers came into contact with moisture, and showed poor storage stability. Moreover, the composition for external use on skin (Comparative Example 7) in which the proportion of agar mixed was lower than the range of the present invention imparted a feeling of stickiness and sliminess and was insufficiently spread on the skin, and dirt generation and slipperiness at the time when fingers came into contact with moisture were partially confirmed.

The composition for external use on skin (Comparative Example 3) not mixed with the divalent polyol as the component (B) imparted a feeling of stickiness. Moreover, dirt generation and feeling of sliminess were partially confirmed, and storage stability was insufficient.

These results clearly showed that the composition for external use on skin according to the present invention produced the effects described above.

Example 19 and Comparative Examples 9 and 10

Production Method

According to the compounding shown in Table 5, a component a was weighed and put in a beaker, mixed and dissolved by being heated at 80° C. to 95° C., and then the resultant was cooled slowly while being stirred with a table disper mixer at 2000 rpm. After the mixture was cooled to 40° C., a component b that had been dissolved in a different container was added thereto, and the mixture was stirred evenly. After being cooled to room temperature, the mixture was deaerated under reduced pressure, thereby obtaining a sample.

TABLE 5

Example 19 and Comparative Examples 9 and 10 (% by mass)

| | Component | Example 19 | Comparative Example 9 | Comparative Example 10 |
|---|---|---|---|---|
| a | Agar 1 | 0.9 | — | — |
| | Xanthan gum *[1] | 0.6 | — | — |
| | Native gellan gum *[2] | — | 1.0 | — |
| | Carboxyvinyl polymer *[3] | — | — | 0.4 |
| | Sodium hydroxide | — | — | 0.1 |
| | 1,3-propanediol | 10 | 10 | 10 |
| | Glycerin | 10 | 10 | 10 |
| | Methylparaben | 0.2 | 0.2 | 0.2 |

TABLE 5-continued

Example 19 and Comparative Examples 9 and 10 (% by mass)

|   | Component | Example 19 | Comparative Example 9 | Comparative Example 10 |
|---|---|---|---|---|
|   | Dimethyl polysiloxane (100cs) *4 | 5 | 5 | 5 |
|   | Squalane | 5 | 5 | 5 |
|   | water | 44.3 | 44.8 | 45.3 |
| b | L-ascorbic acid-2-phosphate magnesium ester | 3 | 3 | 3 |
|   | Sodium citrate | 1 | 1 | 1 |
|   | Water | 20 | 20 | 20 |
|   | Total | 100 | 100 | 100 |
|   | Feeling of stickiness | A | C | C |
|   | Spreadability on skin | A | D | B |
|   | Dirt generation | A | C | D |
|   | Feeling of sliminess | A | C | C |
|   | Re-lubricating property of fingers | A | D | C |
|   | Storage stability | A | D | D |

*1 "NOMCORT ZZ" (manufactured by The Nisshin OilliO Group, Ltd.)
*2 "Kelcogel LT-100" (manufactured by San-Ei Gen F.F.I., Inc.)
*3 "Carbopol 940" (manufactured by Lubrizol Advanced Materials)
*4 "KF-96 100cs" (manufactured by Shin-Etsu Chemical Co., Ltd.)

The above compositions were evaluated in terms of the feeling during use and storage stability in the same manner as in Examples 1 to 18 and Comparative Examples 1 to 8. As a result, Example 19 was markedly excellent in all evaluation items as shown in Table 5.

On the other hand, in the composition for external use on skin (Comparative Example 9) mixed with native gellan gum instead of the component (A) of the present invention and the composition for external use on skin (Comparative Example 10) mixed with a carboxyvinyl polymer and sodium hydroxide, the feeling during use and storage stability were greatly impaired. Presumably, this is because due to the influence of sodium citrate or magnesium L-ascorbic acid-2-phosphate magnesium ester, which is a water-soluble ion component, the gel strength of the native gellan gum and viscosity of the carboxyvinyl polymer changed.

Example 20

Essence

The essence shown in Table 6 was prepared by the following production method.
(Production Method)
A component a was dispersed by being stirred with a table disper mixer at 2000 rpm at 90° C. for 20 minutes. After the resultant was cooled to 50° C., a component b was added thereto, and cooled to room temperature while being stirred.

The obtained essence imparted a slight feeling of stickiness, was spread excellently on the skin, did not generate scum, imparted a slight feeling of sliminess, suppressed the re-lubricating property of fingers, and showed excellent storage stability.

TABLE 6

Example 20 (Essence)

|   | Component | Compounding (% by mass) |
|---|---|---|
| a | Agar 1 | 0.60 |
|   | Xanthan gum *1 | 0.40 |
|   | Propylene glycol | 5.00 |

TABLE 6-continued

Example 20 (Essence)

|   | Component | Compounding (% by mass) |
|---|---|---|
|   | 1,2-pentanediol | 2.00 |
|   | Glycerin | 5.00 |
|   | Methylparaben | 0.10 |
|   | Ethylparaben | 0.05 |
|   | Deionized water | 86.74 |
| b | Sodium hyaluronate | 0.01 |
|   | Citric acid | 0.02 |
|   | Sodium citrate | 0.08 |
|   | Total | 100.00 |

*1 "NOMCORT ZZ" (manufactured by The Nisshin OilliO Group, Ltd.)

Example 21

Emulsion Type Essence

The emulsion type essence shown in Table 7 was prepared according to the following production method.
(Production Method)
A component a was dissolved at 90° C., and a component b was evenly dispersed by stirring at 90° C. Thereafter, the component a was added to the component b, and the mixture was dispersed by being stirred with a table disper mixer at 2000 rpm for 10 minutes, followed by cooling to room temperature under stirring.

The obtained emulsion type essence imparted a slight feeling of stickiness, was spread excellently on the skin, did not generate dirt, imparted a slight feeling of sliminess, suppressed the re-lubricating property of fingers, and showed excellent storage stability.

TABLE 7

Example 21 (emulsion type essence)

|   | Component | Compounding (% by mass) |
|---|---|---|
| a | Macadamia nut oil *1 | 0.50 |
|   | Cetyl 2-ethylhexanoate *2 | 0.50 |
|   | Glyceryl tri-2-ethylhexanoate *3 | 0.20 |
|   | Squalane | 0.20 |
|   | Dipentaerythrityl hexa(hydroxystearate/stearate/rosinate) *4 | 0.10 |
|   | Dimethylpolysiloxane (10cs) *5 | 0.10 |
|   | POE (60) hydrogenated castor oil | 0.02 |
| b | Agar 1 | 1.40 |
|   | Xanthan gum *6 | 0.60 |
|   | Dipropylene glycol | 3.00 |
|   | 1,3-Butylene glycol | 2.00 |
|   | Glycerin | 3.00 |
|   | Sodium pyrrolidone carboxylate | 0.40 |
|   | Sodium citrate | 0.50 |
|   | Ascorbic acid glucoside | 2.00 |
|   | Potassium hydroxide | 0.40 |
|   | Methylparaben | 0.10 |
|   | Phenoxyethanol | 0.50 |
|   | Deionized water | 83.88 |
|   | Total | 100.00 |

*1 "Refined macadamia oil" (manufactured by Yokozeki Oil & Fat Industries Co., Ltd.) (relative permittivity 3.1)
*2 "SALACOS 816T" (manufactured by The Nisshin OilliO Group, Ltd.) (relative permittivity 3.1)
*3 "T.I.O" (manufactured by The Nisshin OilliO Group, Ltd.) (relative permittivity 4.2)
*4 "COSMOL 168AR" (manufactured by The Nisshin OilliO Group, Ltd.) (relative permittivity 4.8)
*5 "KF-96 10cs" (manufactured by Shin-Etsu Chemical Co., Ltd.)
*6 "NOMCORT Z" (manufactured by The Nisshin OilliO Group, Ltd.)

Example 22

Emulsion

The emulsion shown in Table 8 was prepared according to the following production method.

(Production Method)

A component a was dissolved at 90° C., and a component b was evenly dispersed by being stirred at 90° C. The component b was added to the component a, and the mixture was dispersed by being stirred with a table disper mixer at 2000 rpm for 10 minutes, followed by cooling to room temperature under stirring.

The obtained emulsion imparted a slight feeling of stickiness, was spread excellently on the skin, did not generate dirt, imparted a slight feeling of sliminess, suppressed the re-lubricating property of fingers, and showed excellent storage stability.

TABLE 8

Example 22 (Emulsion)

| | Component | Compounding (% by mass) |
|---|---|---|
| a | Squalane | 5.00 |
| | Neopentyl glycol dicaprate *1 | 5.00 |
| | Glyceryl tri-2-ethylhexanoate *2 | 5.00 |
| | Dipentaerythrityl hexa(hydroxystearate/stearate/rosinate) *3 | 0.50 |
| | Dimethylpolysiloxane (100cs) | 0.50 |
| | POE (60) hydrogenated castor oil | 0.10 |
| b | Agar 1 | 1.40 |
| | Xanthan gum *4 | 0.60 |
| | Dipropylene glycol | 3.00 |
| | 1,3-butylene glycol | 2.00 |
| | Glycerin | 3.00 |
| | Sodium pyrrolidone carboxylate | 0.40 |
| | Sodium citrate | 0.50 |
| | Disodium L-ascorbate-2-sulfate | 2.00 |
| | Methylparaben | 0.10 |
| | Phenoxyethanol | 0.50 |
| | Deionized water | 69.4 |
| Total | | 100.00 |

*1 "ESTEMOL N-01" (manufactured by The Nisshin OilliO Group, Ltd.) (relative permittivity 3.4)
*2 "T.I.O" (manufactured by The Nisshin OilliO Group, Ltd.) (relative permittivity 4.2)
*3 "COSMOL 168AR" (manufactured by The Nisshin OilliO Group, Ltd.) (relative permittivity 4.8)
*4 "NOMCORT Z" (manufactured by The Nisshin OilliO Group, Ltd.)

Example 23

Cream

The cream shown in Table 9 was prepared according to the following production method.

(Production Method)

A component a was dissolved at 90° C., and a component b was evenly dispersed by being stirred at 90° C. Thereafter, the component b was added to the component a, and the mixture was dispersed by being stirred with a table disper mixer at 2000 rpm for 10 minutes, followed by cooling to room temperature under stirring.

The obtained cream imparted a slight feeling of stickiness, was spread excellently on the skin, did not generate scum, imparted a slight feeling of sliminess, suppressed the re-lubricating property of fingers, and showed excellent storage stability.

TABLE 9

Example 23 (Cream)

| | Component | Compounding (% by mass) |
|---|---|---|
| a | α-olefin oligomer*1 | 5.00 |
| | Neopentyl glycol dicaprate*2 | 10.00 |
| | Pentaerythrityl tetra-2-ethylhexanoate*3 | 5.00 |
| | Phytosteryl oleate*4 | 4.00 |
| | Microcrystalline wax | 2.00 |
| | Cetanol | 4.00 |
| | Dimethylpolysiloxane (100cs) | 0.50 |
| | Polyglyceryl-10 oleate*5 | 0.08 |
| | Polyglyceryl-2 oleate*6 | 0.02 |
| | Hydrogenated lecithin*7 | 0.05 |
| b | Agar 1 | 1.40 |
| | Xanthan gum*8 | 0.60 |
| | Dipropylene glycol | 5.00 |
| | Glycerin | 5.00 |
| | Diglycerin | 0.50 |
| | L-ascorbic acid-2-phosphate magnesium ester | 3.00 |
| | Methylparaben | 0.10 |
| | Phenoxyethanol | 0.50 |
| | Deionized water | 51.25 |
| Total | | 100.00 |

*1 "NOMCORT HP-30" (manufactured by The Nisshin OilliO Group, Ltd.)
*2 "ESTEMOL N-01" (manufactured by The Nisshin OilliO Group, Ltd.) (relative permittivity 3.4)
*3 "SALACOS 5408" (manufactured by The Nisshin OilliO Group, Ltd.) (relative permittivity 3.0)
*4 "SALACOS PO(T)" (manufactured by The Nisshin OilliO Group, Ltd.)
*5 "SALACOS PG-180" (manufactured by The Nisshin OilliO Group, Ltd.)
*6 "SALACOS DG-180" (manufactured by The Nisshin OilliO Group, Ltd.)
*7 "Basis LS-60HR" (manufactured by The Nisshin OilliO Group, Ltd.)
*8 "NOMCORT Z" (manufactured by The Nisshin OilliO Group, Ltd.)

Examples 24 to 49 and Comparative Examples 11 to 22

Production Method

According to the compounding shown in Tables 10 to 14, all components were weighted and put in a beaker, and mixed and dissolved by being heated at 80° C. to 95° C., and then the resultant was cooled slowly while being stirred with a table disper mixer at 1000 rpm. The resultant was deaerated under reduced pressure, and the thus obtained oil-in-water type emulsion composition was taken as a sample.

(Feeling During Use)

The respective compositions for external use on skin were applied to the whole face of a panel consisting of 15 members after the face was washed, and the feeling during use and the storage stability were evaluated in the same manner as in Examples 1 to 18. The evaluation results are shown in Tables 10 to 14.

TABLE 10

Examples 24 to 34

(% by mass)

| | Example | | | | | | | | | | |
|---|---|---|---|---|---|---|---|---|---|---|---|
| | 24 | 25 | 26 | 27 | 28 | 29 | 30 | 31 | 32 | 33 | 34 |
| Agar 1 | 0.9 | 0.9 | 0.9 | 0.9 | 0.9 | 0.9 | 0.9 | 0.9 | 0.9 | 0.9 | 0.9 |
| Xanthan gum | 0.6 | 0.6 | 0.6 | 0.6 | 0.6 | 0.6 | 0.6 | 0.6 | 0.6 | 0.6 | 0.6 |
| Hydrogenated polydecene*2 | 10 | 20 | 30 | — | — | — | — | — | — | — | — |
| Cetyl 2-ethylhexanoate*3 | — | — | — | 10 | 20 | — | — | — | — | — | — |
| Propanediol di(caprylate/caprate)*4 | — | — | — | — | — | 10 | 20 | — | — | — | — |
| Triethylhexanoin*5 | — | — | — | — | — | — | — | 10 | 20 | — | — |
| Polyglyceryl-2 triisostearate*6 | — | — | — | — | — | — | — | — | — | 10 | 20 |
| Methylparaben | 0.1 | 0.1 | 0.1 | 0.1 | 0.1 | 0.1 | 0.1 | 0.1 | 0.1 | 0.1 | 0.1 |
| 1,3-Butylene glycol | 5 | 5 | 5 | 5 | 5 | 5 | 5 | 5 | 5 | 5 | 5 |
| Purified water | 83.4 | 73.4 | 63.4 | 83.4 | 73.4 | 83.4 | 73.4 | 83.4 | 73.4 | 83.4 | 73.4 |
| Total | 100 | 100 | 100 | 100 | 100 | 100 | 100 | 100 | 100 | 100 | 100 |
| Feeling of stickiness | A | A | A | A | A | A | A | A | A | A | B |
| Spreadability on skin | A | A | A | A | A | A | A | A | A | A | A |
| Dirt generation | A | A | A | A | A | A | A | A | A | A | A |
| Feeling of sliminess | A | A | A | A | A | A | A | A | A | A | A |
| Re-lubricating property of fingers | A | A | A | A | A | A | A | A | A | A | A |
| Storage stability | A | A | A | A | A | A | A | A | A | A | A |

*1"NOMCORT ZZ" (manufactured by The Nisshin OilliO Group, Ltd.)
*2"NOMCORT HP-30" (manufactured by The Nisshin OilliO Group, Ltd.)
*3"SALACOS 816T" (manufactured by The Nisshin OilliO Group, Ltd.) (relative permittivity 3.1)
*4"SALACOS PR-85" (manufactured by The Nisshin OilliO Group, Ltd.) (relative permittivity 4.0)
*5"T.I.O" (manufactured by The Nisshin OilliO Group, Ltd.) (relative permittivity 4.2)
*6"COSMOL 43V" (manufactured by The Nisshin OilliO Group, Ltd.) (relative permittivity 3.7)

TABLE 11

Examples 35 to 44

(% by mass)

| | Example | | | | | | | | | |
|---|---|---|---|---|---|---|---|---|---|---|
| | 35 | 36 | 37 | 38 | 39 | 40 | 41 | 42 | 43 | 44 |
| Agar 1 | 0.9 | 0.9 | 0.9 | 0.9 | 0.9 | 0.9 | 0.9 | 0.9 | 0.9 | 0.9 |
| Xanthan gum*1 | 0.6 | 0.6 | 0.6 | 0.6 | 0.6 | 0.6 | 0.6 | 0.6 | 0.6 | 0.6 |
| Diisostearyl maleate*2 | 10 | 20 | 30 | 40 | — | — | — | — | — | — |
| Dipentaerythrityl tri-polyhydroxystearate*3 | — | — | — | — | 10 | 20 | 30 | — | — | — |
| Trehalose isostearate esters*4 | — | — | — | — | — | — | — | 10 | 20 | 30 |
| Methylparaben | 0.1 | 0.1 | 0.1 | 0.1 | 0.1 | 0.1 | 0.1 | 0.1 | 0.1 | 0.1 |
| 1,3-butylene glycol | 5 | 5 | 5 | 5 | 5 | 5 | 5 | 5 | 5 | 5 |
| Purified water | 83.4 | 73.4 | 63.4 | 53.4 | 83.4 | 73.4 | 63.4 | 73.4 | 73.4 | 63.4 |
| Total | 100 | 100 | 100 | 100 | 100 | 100 | 100 | 100 | 100 | 100 |
| Feeling of stickiness | A | A | B | B | A | A | B | A | A | A |
| Spreadability on skin | A | A | A | A | A | A | A | A | A | A |
| Dirt generation | A | A | A | A | A | A | A | A | A | A |
| Feeling of sliminess | A | A | A | A | A | A | A | A | A | A |
| Re-lubricating property of fingers | A | A | A | A | A | A | A | A | A | A |
| Storage stability | A | A | A | A | A | A | A | A | A | A |

*1"NOMCORT ZZ" (manufactured by The Nisshin OilliO Group, Ltd.)
*2"COSMOL 222" (manufactured by The Nisshin OilliO Group, Ltd.) (relative permittivity 3.7)
*3"SALACOS WO-6" (manufactured by The Nisshin OilliO Group, Ltd.) (relative permittivity 4.1)
*4"NOMCORT TQ-5" (manufactured by The Nisshin OilliO Group, Ltd.) (relative permittivity 3.6)

TABLE 12

Examples 45 to 49

(% by mass)

| | Example 45 | Example 46 | Example 47 | Example 48 | Example 49 |
|---|---|---|---|---|---|
| Agar 1 | 0.9 | 0.9 | 0.9 | 1.2 | 0.2 |
| Xanthan gum*1 | 0.6 | 0.6 | 0.6 | 0.3 | 0.1 |
| Ethylhexyl methoxycinnamate*2 | 10 | — | — | — | — |
| Dimethylpolysiloxane (6cs)*3 | — | 10 | 20 | — | — |
| Decamethyl cyclopentasiloxane*4 | — | — | — | 10 | 20 |
| Methylparaben | 0.1 | 0.1 | 0.1 | 0.1 | 0.1 |
| 1,3-Butylene glycol*2 | 5 | 5 | 5 | 5 | 5 |
| Purified water | 83.4 | 83.4 | 73.4 | 83.4 | 73.4 |
| Total | 100 | 100 | 100 | 100 | 100 |
| Feeling of stickiness | A | A | A | A | A |
| Spreadability on skin | A | A | A | A | A |
| Dirt generation | A | A | A | A | A |
| Feeling of sliminess | A | A | A | A | A |
| Re-lubricating property of fingers | A | A | A | A | A |
| Storage stability | A | A | A | A | B |

*1"NOMCORT ZZ" (manufactured by The Nisshin OilliO Group, Ltd.)
*2"NOMCORT TAB" (manufactured by The Nisshin OilliO Group, Ltd.)
*3"KF96-6cs" (manufactured by Shin-Etsu Chemical Co., Ltd.)
*4"SH245" (manufactured by Dow Corning Toray Co., Ltd.)

TABLE 13

Comparative Examples 11 to 18

(% by mass)

| | 11 | 12 | 13 | 14 | 15 | 16 | 17 | 18 |
|---|---|---|---|---|---|---|---|---|
| Agar 1 | 0.9 | 0.9 | 0.9 | 0.9 | 0.9 | 0.9 | 0.9 | 0.9 |
| Locust bean gum*1 | 0.6 | 0.6 | — | — | — | — | — | — |
| Carrageenan*2 | — | — | 0.6 | 0.6 | — | — | — | — |
| Gum arabic*3 | — | — | — | — | 0.6 | 0.6 | — | — |
| Gellan gum*4 | — | — | — | — | — | — | 0.6 | 0.6 |
| Hydrogenated polydecene*5 | 10 | — | 10 | — | 10 | — | 10 | — |
| Dipentaerythrityl tri-polyhydroxystearate*6 | — | 10 | — | 10 | — | 10 | — | 10 |
| Methylparaben | 0.1 | 0.1 | 0.1 | 0.1 | 0.1 | 0.1 | 0.1 | 0.1 |
| 1,3-Butylene glycol | 5 | 5 | 5 | 5 | 5 | 5 | 5 | 5 |
| Purified water | 83.4 | 83.4 | 83.4 | 83.4 | 83.4 | 83.4 | 83.4 | 83.4 |
| Total | 100 | 100 | 100 | 100 | 100 | 100 | 100 | 100 |
| Feeling of stickiness | C | D | D | D | D | D | D | D |
| Spreadability on skin | B | C | C | C | C | C | B | C |
| Dirt generation | D | D | C | D | D | D | D | D |
| Feeling of sliminess | D | D | D | D | C | C | D | D |
| Re-lubricating property of fingers | C | D | D | D | C | C | D | D |
| Storage stability | D | D | D | D | D | D | C | C |

*1"Locust bean gum F" (manufactured by San-Ei Gen F.F.I., Inc)
*2"Inagel XH-61" (manufactured by Ina Food Industry Co., Ltd.)
*3"Gum arabic A" (manufactured by Ina Food Industry Co., Ltd.)
*4"Kelcogel" (manufactured by San-Ei Gen F.F.I., Inc.)
*5"NOMCORT HP-30" (manufactured by The Nisshin OilliO Group, Ltd.)
*6"SALACOS WO-6" (manufactured by The Nisshin OilliO Group, Ltd.) (relative permittivity 4.1)

TABLE 14

Comparative Examples 19 to 22

(% by mass)

| | 19 | 20 | 21 | 22 |
|---|---|---|---|---|
| Agar 1 | 0.9 | 0.9 | 0.9 | 0.9 |
| Locust bean gum*1 | 0.6 | — | — | — |
| Carrageenan*2 | — | 0.6 | — | — |
| Gum arabic*3 | — | — | 0.6 | — |
| Gellan gum*4 | — | — | — | 0.6 |
| 1,3-propanediol | 10 | 10 | 10 | 10 |
| Glycerin | 10 | 10 | 10 | 10 |
| Methylparaben | 0.2 | 0.2 | 0.2 | 0.2 |
| Neopentyl glycol dicaprate*5 | 10 | 10 | 10 | 10 |
| Water | 68.3 | 68.3 | 68.3 | 68.3 |
| Total | 100 | 100 | 100 | 100 |
| Feeling of stickiness | D | D | D | D |
| Spreadability on skin | C | C | C | C |
| Dirt generation | D | D | D | D |
| Feeling of sliminess | D | D | D | D |
| Re-lubricating property of fingers | D | D | D | D |
| Storage stability | D | D | D | D |

*1"Locust bean gum F" (manufactured by San-Ei Gen F.F.I., Inc)
*2"Inagel XH-61" (manufactured by Ina Food Industry Co., Ltd.)
*3"Gum arabic A" (manufactured by Ina Food Industry Co., Ltd.)
*4"Kelcogel" (manufactured by San-Ei Gen F.F.I., Inc.)
*5"ESTEMOL N-01" (manufactured by The Nisshin OilliO Group, Ltd.) (relative permittivity 3.4)

As a result, all of the compositions for external use on skin of Examples 24 to 49 according to the present invention were excellent since they did not impart a feeling of stickiness or sliminess, were spread excellently on the skin, did not generate the dirt-like scum, and did not make fingers slippery even when the fingers came into contact with moisture again. In addition, even being stored at 50° C. for a month, these oil-in-water type emulsion compositions did not produce a liquid residue and showed excellent emulsion stability of oil, that is, showed excellent storage stability.

On the other hand, all of the compositions for external use on skin (Comparative Examples 11 to 22) not mixed with xanthan gum imparted a feeling of stickiness, were spread insufficiently on the skin, and showed poor storage stability.

These results clearly show that the composition for external use on skin according to the present invention produces the effects described above.

Example 50

Cleansing Gel

The cleansing gel shown in Table 15 was prepared according to the following production method.

(Production Method)

A component a was dissolved at 90° C., and a component b was evenly dispersed by being stirred at 90° C. The component b was added to the component a, and the mixture was dispersed by being stirred with a table disper mixer at 1000 rpm for 10 minutes, followed by cooling to room temperature under stirring.

The obtained cleansing gel had an excellent cleansing ability, was not irritating to the skin or the eyes, imparted slight feeling of stickiness, did not generate dirt, imparted slight feeling of sliminess, suppressed the re-lubricating property of fingers, and showed excellent storage stability. Furthermore, even if prepared by being stirred with a disper mixer at a low shear rate such as 1000 rpm in the stirring at the time of cooling, this gel was spread excellently on the skin.

TABLE 15

Example 50 (Cleansing Gel)

| | Component | Compounding (% by mass) |
|---|---|---|
| a | Propanediol di(caprylate/caprate)[*1] | 15.0 |
| | Isononyl isononanoate[*2] | 5.0 |
| b | Agar 1 | 0.9 |
| | Xanthan gum[*3] | 0.6 |
| | 1,3-propanediol | 7.0 |
| | Methylparaben | 0.1 |
| | Deionized water | 71.4 |
| | Total | 100.0 |

[*1]"SALACOS PR-85" (manufactured by The Nisshin OilliO Group, Ltd.) (relative permittivity 4.0)
[*2]"SALACOS 99" (manufactured by The Nisshin OilliO Group, Ltd.) (relative permittivity 3.3)
[*3]"NOMCORT Z" (manufactured by The Nisshin OilliO Group, Ltd.)

Example 51

Vitamin C Derivative-Mixed Essence

The emulsion shown in Table 16 was prepared according to the following production method.

(Production Method)

A component a was dissolved at 90° C., and a component b was evenly dispersed by being stirred at 90° C. The component b was added to the component a, and the mixture was dispersed by being stirred with a table disper mixer at 1000 rpm for 10 minutes, followed by cooling to room temperature under stirring.

Although dipentaerythrityl tri-polyhydroxystearate and dimethylpolysiloxane used were a combination of oils incompatible with each other, the obtained vitamin C derivative-mixed essence showed improvement of spreadability on the skin, did not impart a feeling of stickiness, did not generate dirt, did not impart a feeling of sliminess, suppressed the re-lubricating property of fingers, and showed excellent storage stability. Moreover, even if prepared by being stirred with a disper mixer at a low shear rate such as 1000 rpm in the stirring at the time of cooling, this essence was spread excellently on the skin.

TABLE 16

Example 51 (Vitamin C Derivative-Mixed Essence)

| | Component | Compounding (% by mass) |
|---|---|---|
| a | Dipentaerythrityl tri-polyhydroxystearate[*1] | 5.0 |
| | Ascorbyl tetrahexyldecanoate[*2] | 2.0 |
| | Dimethylpolysiloxane (6cs)[*3] | 10.0 |
| b | Agar 1 | 0.9 |
| | Xanthan gum[*4] | 0.6 |
| | 1,3-propanediol | 5.0 |
| | L-ascorbic acid-2-phosphate magnesium ester | 3.0 |
| | Deionized water | 73.5 |
| | Total | 100.0 |

[*1]"SALACOS WO-6" (manufactured by The Nisshin OilliO Group, Ltd.) (relative permittivity 4.1)
[*2]"NIKKOL VC-IP" (manufactured by Nikko Chemicals Co., Ltd.)
[*3]"KF 96-6cs" (manufactured by Shin-Etsu Chemical Co., Ltd.)
[*4]"NOMCORT ZZ" (manufactured by The Nisshin OilliO Group, Ltd.)

Example 52

Sunscreen

The sunscreen shown in Table 17 was prepared according to the following production method.

(Production Method)

A component a was dissolved at 90° C., and a component b was evenly dispersed by being stirred at 90° C. The component b was added to the component a, and the mixture was dispersed by being stirred with a table disper mixer at 1000 rpm for 10 minutes, followed by cooling to room temperature under stirring.

Although ethylhexyl methoxycinnamate and dimethylpolysiloxane used were a combination of oils incompatible with each other, the obtained sunscreen imparted slight feeling of stickiness, did not generate dirt, imparted slight feeling of sliminess, suppressed the re-lubricating property of fingers, and showed excellent storage stability. Moreover, even if prepared by being stirred with a disper mixer at a low shear rate such as 1000 rpm in the stirring at the time of cooling, this sunscreen was spread excellently on the skin.

TABLE 17

Example 52 (Sunscreen)

| | Component | Compounding (% by mass) |
|---|---|---|
| a | Ethylhexyl methoxycinnamate[*1] | 10.00 |
| | Trimethyl siloxysilicate (70%)[*2] | 3.00 |
| | Dimethylpolysiloxane (6cs)[*3] | 5.00 |
| b | Agar 1 | 0.90 |
| | Xanthan gum[*4] | 0.60 |
| | 1,3-propanediol | 5.00 |
| | Methylparaben | 0.10 |
| | Deionized water | 75.4 |
| | Total | 100.0 |

[*1]"NOMCORT TAB" (manufactured by The Nisshin OilliO Group, Ltd.)
[*2]"KF-7312K" (manufactured by Shin-Etsu Chemical Co., Ltd.)
[*3]"KF 96-6cs" (manufactured by Shin-Etsu Chemical Co., Ltd.)
[*4]"NOMCORT ZZ" (manufactured by The Nisshin OilliO Group, Ltd.)

Example 53

The oil-in-water type emulsion composition shown in Table 18 was prepared according to the following production method, so as to investigate the emulsified state of a composition obtained when a combination of oils incompatible with each other is mixed similarly to Examples 51 and 52.

(Production Method)

A component a was dissolved at 90° C., and a component b was evenly dispersed by being stirred at 90° C. The component b was added to the component a, and the mixture was dispersed by being stirred with a table disper mixer at 1000 rpm for 10 minutes, and their cooled to room temperature while being stirred.

TABLE 18

Example 53 (Oil-In-Water Type Emulsion Composition)

| | Component | Compounding (% by mass) |
|---|---|---|
| a | Dipentaerythrityl tri-polyhydroxystearate*[1] | 10.0 |
| | Dimethylpolysiloxane (6cs)*[2] | 5.0 |
| b | Agar 1 | 0.9 |
| | Xanthan gum*[3] | 0.6 |
| | 1,3-butylene glycol | 5.0 |
| | Deionized water | 78.5 |
| | Total | 100.0 |

*[1]"SALACOS WO-6" (manufactured by The Nisshin OilliO Group, Ltd.) (relative permittivity 4.1)
*[2]"KF 96-6cs" (manufactured by Shin-Etsu Chemical Co., Ltd.)
*[3]"NOMCORT ZZ" (manufactured by The Nisshin OilliO Group, Ltd.)

Violet No. 201 and Red No. 227 (dyeing agents) were added to the obtained oil-in-water type emulsion composition. Dipentaerythrityl tri-polyhydroxystearate as ester oil was stained blue, a water layer was stained red, and then a microscopic image under transmitted light was captured using Microscope VHX-500 (manufactured by Keyence Corporation). The captured image is shown in FIG. 1. By FIG. 1, it was confirmed that an oil drop of dimethylpolysiloxane was contained in an oil drop of dipentaerythrityl tri-polyhydroxystearate, and these drops were held in a state of being incompatible with each other in an oil bead.

Likewise, in the vitamin C derivative-mixed essence prepared in Example 51 and the sunscreen prepared in Example 52, an oil drop of dimethylpolysiloxane was contained in an oil drop of dipentaerythrityl tri-polyhydroxystearate or ethylhexyl methoxycinnamate, and these oil drops were held in a state of being incompatible with each other in an oil bead. Presumably, for this reason, the composition can be stably emulsified, shows improvement in spreadability on skin, and impart further lessened feeling of stickiness.

That is, the above results clearly show that the composition for external use on skin of the present invention can be stably emulsified even being mixed with a combination of oils incompatible with each other.

Examples 54 to 60

In order to investigate halotolerance, the vitamin C derivative-mixed aqueous solution shown in Table 19 was prepared according to the following production method, and the viscosity thereof was measured.

(Production Method)

According to the compounding shown in Table 19, all components were weighed and put in a beaker, and mixed and dissolved by being heated at 80° C. to 95° C., and then the mixture was slowly cooled while being stirred with a table disper mixer at 2000 rpm.

TABLE 19

Examples 54 to 60

(% by mass)

| | Example | | | | | | |
|---|---|---|---|---|---|---|---|
| | 54 | 55 | 56 | 57 | 58 | 59 | 60 |
| Agar 1 | 0.9 | 0.9 | 0.9 | 0.9 | 0.9 | 0.9 | 0.9 |
| Xanthan gum*[1] | 0.6 | 0.6 | 0.6 | 0.6 | 0.6 | 0.6 | 0.6 |
| L-ascorbic acid-2-glucoside | — | 0.5 | 1.0 | 2.0 | — | — | — |
| Magnesium L-ascorbyl phosphate | — | — | — | — | 1.0 | 2.0 | 3.0 |
| Deionized water | 98.5 | 98.0 | 97.5 | 96.5 | 97.5 | 96.5 | 95.5 |
| total | 100 | 100 | 100 | 100 | 100 | 100 | 100 |

*[1]"Momucoat ZZ" (manufactured by The Nisshin OilliO Group, Ltd.)

Figure 2:
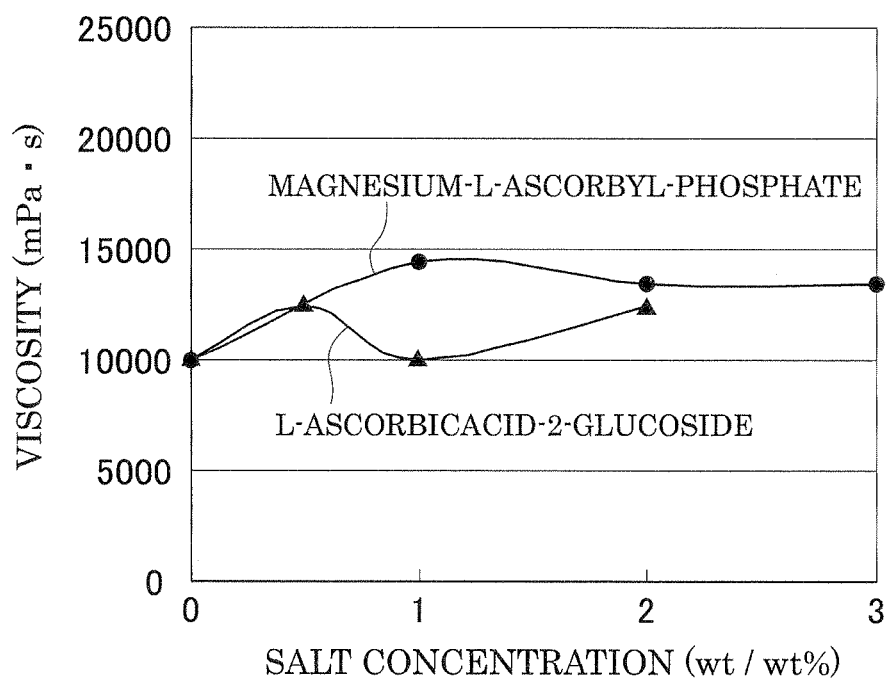
FIG. 2 is a view showing results of viscosity measurement performed on the aqueous vitamin C derivative-mixed solutions of Examples 54 to 60.

Viscosity of the obtained vitamin C derivative-mixed aqueous solution was measured 1 minute after the production of the solution by using a BL type viscometer and under conditions a No. 4 rotor, 6 rpm, and 25° C. The measurement results are shown in FIG. 2. In the drawing, "▲" indicates results of Examples 55 to 57 mixed with L-ascorbic acid-2-glucoside, "●" indicates results of Examples 58 to 60 mixed with magnesium L-ascorbyl phosphate, and a dot where salt concentration is 0% by mass indicates the result of Example 54 not mixed with any of the above components. As shown in FIG. 2, even when the aqueous solution of the water-soluble polymer as the component (A) was mixed with a salt, viscosity did almost not change. The result clearly shows that the composition for external use on skin of the present invention that also contains the component (A) shows excellent tolerance to a salt.

Example 61

Sunscreen

The sunscreen shown in Table 20 was prepared according to the following production method.

(Production Method)

A component a was dissolved at 90° C., and a component b was evenly dispersed by being stirred at 90° C. The component b was added to the component a, and the mixture was dispersed by being stirred with a table disper mixer at 1000 rpm for 10 minutes, followed by cooling to room temperature under stirring.

The obtained sunscreen imparted a slight feeling of stickiness, did not generate dirt, imparted a slight feeling of sliminess, suppressed the re-lubricating property of fingers, and showed excellent storage stability.

TABLE 20

Example 61 (Sunscreen)

| | Component | Compounding (% by mass) |
|---|---|---|
| a | Ethylhexyl methoxycinnamate*[1] | 10.00 |
| | t-Butyl methoxybenzoyl methane*[2] | 10.00 |
| | Trimethyl siloxysilicate (70%)*[3] | 3.00 |
| | Dimethylpolysiloxane (6cs)*[4] | 5.00 |
| b | Agar 1 | 0.90 |
| | Xanthan gum*[5] | 0.60 |

TABLE 20-continued

Example 61 (Sunscreen)

| Component | Compounding (% by mass) |
|---|---|
| 1,3-propanediol | 5.00 |
| Methylparaben | 0.10 |
| Deionized water | 65.4 |
| Total | 100.0 |

*[1]"NOMCORT TAB" (manufactured by The Nisshin OilliO Group, Ltd.)
*[2]"Parsol 1789" (DSM Nutrition Japan K.K.)
*[3]"KF-7312K" (manufactured by Shin-Etsu Chemical Co., Ltd.)
*[4]"KF 96-6cs" (manufactured by Shin-Etsu Chemical Co., Ltd.)
*[5]"NOMCORT ZZ" (manufactured by The Nisshin OilliO Group, Ltd.)

In the related art, in order to maintain a stabilized emulsion state by using ethylhexyl methoxycinnamate and dimethylpolysiloxane which are incompatible with each other, it is necessary to mix oil or the like (for example, hydrogenated polydecene, isononyl isononanoate, or the like) dissolving in both the ethylhexyl methoxycinnamate and the dimethylpolysiloxane so as to make the ethylhexyl methoxycinnamate and the dimethylpolysiloxane compatible with each other. However, since solubility of t-butyl methoxydibenzoyl methane is low in dimethylpolysiloxane, if ethylhexyl methoxycinnamate and dimethylpolysiloxane become compatible with each other, solubility of t-butyl methoxydibenzoyl methane is lowered, which leads to a problem of precipitation at a low temperature. On the other hand, in the sunscreen shown in Example 61, ethylhexyl methoxycinnamate and dimethylpolysiloxane are held in a state of being incompatible with each other. Accordingly, t-butyl methoxydibenzoyl methane is not precipitated at a low temperature, so stability at a low temperature is excellent.

Example 62

Oil-in-Water Type Emulsion Foundation

The oil-in-water type emulsion foundation shown in Table 21 was prepared according to the following production method.

(Production Method)

A component a was dissolved at 90° C., and a component b was evenly dispersed by being stirred at 90° C. The component b was added to the component a, and the mixture was dispersed by being stirred with a table disper mixer at 1000 rpm for 10 minutes, followed by cooling to room temperature under stirring.

Although hydrogenated polyisobutene and dimethylpolysiloxane used were a combination of oils incompatible with each other, the obtained oil-in-water type emulsion foundation imparted a slight feeling of stickiness, did not generate dirt, imparted a slight feeling of sliminess, suppressed the re-lubricating property of fingers, and showed excellent storage stability. Furthermore, even if prepared by being stirred with a disper mixer at a low shear rate such as 1000 rpm in the stirring at the time of cooling, this foundation was spread excellently on the skin. In addition, this foundation showed excellent makeup sustainability and water resistance.

TABLE 21

Example 62 (Oil-In-Water Type Emulsion Foundation)

| | Component | Compounding (% by mass) |
|---|---|---|
| a | Hydrogenated polyisobutene*[1] | 2.00 |
| | Trimethyl siloxysilicate (70%)*[2] | 3.00 |
| | Dimethylpolysiloxane (6cs)*[3] | 15.00 |
| | Talc | 2.70 |
| | Titanium dioxide | 8.40 |
| | Iron oxide (yellow) | 0.60 |
| | Iron oxide (red) | 0.18 |
| | Iron oxide (black) | 0.12 |
| b | Agar 1 | 0.90 |
| | Xanthan gum*[4] | 0.60 |
| | 1,3-propanediol | 5.00 |
| | Methylparaben | 0.10 |
| | Deionized water | 61.4 |
| | Total | 100.0 |

*[1]"Parleam 18" (manufactured by NOF CORPORATION)
*[2]"KF-7312K" (manufactured by Shin-Etsu Chemical Co., Ltd.)
*[3]"KF 96-6cs" (manufactured by Shin-Etsu Chemical Co., Ltd.)
*[4]"NOMCORT ZZ" (manufactured by The Nisshin OilliO Group, Ltd.)

Reference Example 1

Automobile Polishing Agent

The automobile polishing agent shown in Table 22 was prepared according to the following production method.

(Production Method)

According to the compounding shown in Table 22, all components were weighed and put in a beaker, and mixed and dissolved by being heated at 80° C. to 95° C., and then the mixture was slowly cooled by being stirred with a table disper mixer at 1000 rpm.

Durability of the prepared automobile polishing agent was evaluated by the following method.

First, an electrogalvanized steel plate was coated with a commercially available primary surfacer {product name: White Primer (manufactured by Musashi Holt Co., Ltd)} as a coating material for automobiles, a white coating material for automobiles {product name: Anti-rust paint (color No. 041) (manufactured by Musashi Holt Co., Ltd)}, and a clear coating material {product name: top coat clear (manufactured by Musashi Holt Co., Ltd) by spray coating according to the instruction of the respective products, followed by drying at 25° C. for 24 hours, thereby obtaining coated steel plate for test.

Subsequently, the coated steel plate was coated with the automobile polishing agents of Reference Example 1 and Reference Comparative Example 1, and distilled water was dripped to the coated portion to measure a contact angle. Thereafter, the steel plate coated with the polishing agent was exposed outdoors for 24 hours, and a contact angle was measured again. Durability of the coating film was evaluated based on the change in a contact angle before and after the outdoor exposure.

TABLE 22

| (automobile polishing agent) | Reference Example 1 | (% by mass) Reference Comparative Example 1 |
|---|---|---|
| Agar 1 | 3.0 | — |
| Xanthan gum*[1] | 2.0 | — |

TABLE 22-continued

| (automobile polishing agent) | Reference Example 1 | (% by mass) Reference Comparative Example 1 |
|---|---|---|
| Ethylene oxide-added perfluoroalkyl*[2] | — | 2.5 |
| Perfluoropolyether*[3] | 10.0 | 10.0 |
| Light liquid isoparaffin*[4] | 15.0 | 15.0 |
| Polyoxyethylene laurylether (5E.O)*[5] | — | 2.5 |
| Deionized water | 70.0 | 70.0 |
| Total | 100 | 100 |
| Initial contact angle | 115° | 105° |
| Contact angle after time elapse | 95° | 50° |

*[1]"NOMCORT ZZ" (manufactured by The Nisshin OilliO Group, Ltd.)
*[2]"Krytox GPL205" (manufactured by DuPont)
*[3]"Surflon S-243" (manufactured by AGC SEIMI CHEMICAL CO., LTD.)
*[4]"IP Solvent 1620" (manufactured by Idemitsu Kosan Co., Ltd.)
*[5]"EMALEX 705" (manufactured by NIHON EMULSION Co., Ltd.)

As a result, it was understood that the automobile polishing agent of Reference Example 1 practically did not show the change in a contact angle even after exposed outdoors and had high durability of the coating film. On the other hand, it was understood that the automobile polishing agent of Reference Comparative Example 1 showed decrease in a contact angle and had low durability of the coating film. Presumably, the difference in the contact angle of the coating film results from the difference in affinity of the coating film with water, which is a difference caused depending on whether a surfactant is mixed.

Examples 63 to 65

Pigment Dispersion

In order to investigate dispersion stability of pigments, the pigment dispersion shown in Table 22 was prepared according to the following production method, and dispersion stability of pigments was evaluated.

(Production Method)

According to the compounding shown in Table 22, all components were weighed and put in a beaker, and mixed and dissolved by being heated at 80° C. to 95° C., and the mixture was slowly cooled while being stirred with a table disper mixer at 2000 rpm.

(Evaluation of Pigment Dispersibility)

The pigment dispersion prepared according to Table 23 was stored at 50° C. for a month, and aggregation and sedimentation of the pigments were evaluated by visual observation.

TABLE 23

Examples 63 to 65 (pigment dispersion)

| | Example | | (% by mass) |
|---|---|---|---|
| | 63 | 64 | 65 |
| Agar 1 | 0.9 | 0.9 | 0.9 |
| Xanthan gum*[1] | 0.6 | 0.6 | 0.6 |
| Titanium dioxide 1*[2] | 10.0 | — | — |
| Titanium dioxide 2*[3] | — | 10.0 | — |

TABLE 23-continued

Examples 63 to 65 (pigment dispersion)

| | Example | | (% by mass) |
|---|---|---|---|
| | 63 | 64 | 65 |
| Titanium dioxide 3*[4] | — | — | 10.0 |
| Deionized water | 88.5 | 88.5 | 88.5 |
| Total | 100 | 100 | 100 |
| Aggregation of pigment | O | O | O |
| Sedimentation of pigment | O | O | O |

*[1]"NOMCORT ZZ" (manufactured by The Nisshin OilliO Group, Ltd.)
*[2]"MT-100AQ" (manufactured by TAYCA)
*[3]"MT-150W" (manufactured by TAYCA)
*[4]"MT-100WP" (manufactured by TAYCA)

As a result, it was understood that the pigment dispersions shown in Examples 63 to 65 did not show aggregation or sedimentation of pigments and were excellent in pigment dispersibility. Presumably, using the component (A) as an emulsifier made these pigment dispersions also excellent in the dispersion stability of pigments.

Examples 66 to 78 and Comparative Examples 23 to 30

Pigment Composition (Production Method)

According to the compounding shown in Tables 24 and 25, all components were weighed and put in a beaker, and mixed and heated at 80° C. to 95° C., and then the mixture was slowly cooled by being stirred with a table disper mixer at 2000 rpm. The resultant was deaerated under reduced pressure, and the thus obtained pigment dispersion composition was taken as a sample.

(Evaluation of Pigment Dispersibility)

The respective samples were stored at 50° C. for a month, and the aggregation and sedimentation of pigments were evaluated by visual observation. The evaluation criteria are shown below.

[Aggregation of Pigment]
O: Aggregation of pigments was not visually observed.
X: Aggregation of pigments was visually observed.
[Sedimentation of Pigments]
O: Sedimentation of pigments was not visually observed.
X: Sedimentation of pigments was visually observed.

(Feeling During Use)

0.5 g of the respective samples were applied to the back of hands of a panel consisting of 15 members after the hands were washed, and the feeling during use was surveyed by answers to a questionnaire. The "feeling of stickiness", "spreadability on skin", "dirt generation", "feeling of sliminess", and "re-lubricating property of fingers" were evaluated respectively based on the same criteria as in Example 1.

(Water Resistance)

0.5 g of the respective samples were applied to the back of hands of a panel consisting of 15 members after the hands were washed, and the hands were dried. Thereafter, feeling of the pigment dispersion composition remaining on the skin, which was experienced when several drops of water were dripped onto the hand, was evaluated according to the following criteria.

[Water Resistance]

A: 12 or more people answered that the composition did not run down due to running water and water resistance was good.

B: 8 to 11 people answered that the composition did not run down due to running water and water resistance was good.

C: 4 to 7 people answered that the composition did not run down due to running water and water resistance was good.

D: 3 or less people answered that the composition did not run down due to running water and water resistance was good.

TABLE 24

Examples 66 to 78

(% by mass)

| | Example | | | | | | | | | | | | |
|---|---|---|---|---|---|---|---|---|---|---|---|---|---|
| | 66 | 67 | 68 | 69 | 70 | 71 | 72 | 73 | 74 | 75 | 76 | 77 | 78 |
| Agar 1 | 0.9 | 0.9 | 0.9 | 0.9 | 0.9 | 0.9 | 0.9 | 0.6 | 1.8 | 3 | 0.6 | 1.8 | 3 |
| Agar 2 | | | | | | | | | | | | | |
| Xanthan gum*1 | 0.6 | 0.6 | 0.6 | 0.6 | 0.6 | 0.6 | 0.6 | 0.4 | 1.2 | 2 | 0.4 | 1.2 | 2 |
| (Acrylate/alkyl acrylate (C10-30)) cross polymer*2 | | | | | | | | | | | | | |
| Hydrophilic titanium dioxide 1*3 | 30 | | | | | | | 10 | 40 | 55 | | | |
| Hydrophilic titanium dioxide 2*4 | | 30 | | | | | | | | | | | |
| Hydrophilic titanium dioxide 3*5 | | | 30 | | | | | | | | | | |
| Hydrophobic titanium dioxide 1*6 | | | | 30 | | | | | | | 10 | 40 | 55 |
| Hydrophobic titanium dioxide 2*7 | | | | | 30 | | | | | | | | |
| Hydrophilic zinc oxide*8 | | | | | | 30 | | | | | | | |
| Hydrophobic zinc oxide*9 | | | | | | | 30 | | | | | | |
| Deionized water | 68.5 | 68.5 | 68.5 | 68.5 | 68.5 | 68.5 | 68.5 | 89 | 57 | 40 | 89 | 57 | 40 |
| Total | 100 | 100 | 100 | 100 | 100 | 100 | 100 | 100 | 100 | 100 | 100 | 100 | 100 |
| Aggregation of pigment | O | O | O | O | O | O | O | O | O | O | O | O | O |
| Sedimentation of pigment | O | O | O | O | O | O | O | O | O | O | O | O | O |
| Feeling of stickiness | A | A | A | A | A | A | A | A | A | B | A | A | B |
| Spreadability on skin | A | A | A | A | A | A | A | A | A | B | A | A | B |
| Dirt generation | A | A | A | A | A | A | A | A | A | B | A | A | B |
| Feeling of sliminess | A | A | A | A | A | A | A | A | A | A | A | A | A |
| Re-lubricating property of fingers | A | A | A | A | A | A | A | A | A | A | A | A | A |
| Water resistance | B | B | B | A | A | B | A | B | B | B | B | A | A |

TABLE 25

(% by mass)

| | Comparative Example | | | | | | | |
|---|---|---|---|---|---|---|---|---|
| | 23 | 24 | 25 | 26 | 27 | 28 | 29 | 30 |
| Agar 1 | 0.9 | — | — | — | 0.9 | — | — | — |
| Agar 2 | — | — | 0.9 | — | — | — | 0.9 | — |
| Xanthan gum*1 | — | 0.6 | 0.6 | — | — | 0.6 | 0.6 | — |
| (Acrylate/alkyl acrylate (C10-30)) cross polymer*2 | — | — | — | 0.3 | — | — | — | 0.3 |
| Hydrophilic titanium dioxide 1*3 | 30 | 30 | 30 | 30 | — | — | — | — |
| Hydrophilic titanium dioxide 2*4 | — | — | — | — | — | — | — | — |
| Hydrophilic titanium dioxide 3*5 | — | — | — | — | — | — | — | — |
| Hydrophobic titanium dioxide 1*6 | — | — | — | — | 30 | 30 | 30 | 30 |
| Hydrophobic titanium dioxide 2*7 | — | — | — | — | — | — | — | — |
| Hydrophilic zinc oxide*8 | — | — | — | — | — | — | — | — |
| Hydrophobic zinc oxide*9 | — | — | — | — | — | — | — | — |
| Deionized water | 69.1 | 69.4 | 68.5 | 69.7 | 69.1 | 69.4 | 68.5 | 69.7 |
| Total | 100 | 100 | 100 | 100 | 100 | 100 | 100 | 100 |

TABLE 25-continued

| | Comparative Example (% by mass) | | | | | | | |
|---|---|---|---|---|---|---|---|---|
| | 23 | 24 | 25 | 26 | 27 | 28 | 29 | 30 |
| Aggregation of pigment | O | O | X | X | O | O | O | X |
| Sedimentation of pigment | X | O | O | O | X | O | O | O |
| Feeling of stickiness | D | D | D | C | D | D | D | C |
| Spreadability on skin | C | C | C | D | C | B | C | D |
| Dirt generation | C | C | D | C | B | C | D | C |
| Feeling of sliminess | A | D | B | C | A | D | B | D |
| Re-lubricating property of fingers | B | D | C | D | B | D | D | C |
| Water resistance | D | C | D | D | C | B | B | C |

*[1]"NOMCORT ZZ" (manufactured by The Nisshin OilliO Group, Ltd.)
*[2]"Pemulen TR-1" (Lubrizol Advanced Materials)
*[3]"MT-100WP" (manufactured by TAYCA)
*[4]"MT-100AQ" (manufactured by TAYCA)
*[5]"MT-150W" (manufactured by TAYCA)
*[6]"MTY-02" (manufactured by TAYCA)
*[7]"MT-100TV" (manufactured by TAYCA)
*[8]"Maxlight ZS-64" (manufactured by SHOWA DENKO K.K.)
*[9]"MZ-303S" (manufactured by TAYCA)

As a result, all of the pigment dispersion compositions of Examples 66 to 78 according to the present invention were excellent since they did not impart a feeling of stickiness or sliminess, were spread excellently on the skin, did not generate the dirt-like scum, and did not make fingers slippery even when the fingers came into contact with moisture again. In addition, even when these compositions for external use on skin were stored at 50° C. for a month, aggregation and sedimentation of pigments were not observed, and pigment dispersibility was excellent, that is, storage stability was excellent. Among the compositions, Examples 69, 70, and 72 using hydrophobic pigments showed markedly excellent water resistance.

On the other hand, the pigment dispersion compositions (Comparative Examples 23 and 27) not mixed with xanthan gum imparted a feeling of stickiness, were spread insufficiently on the skin, and showed poor storage stability.

The pigment dispersion compositions (Comparative Examples 24 and 28) not mixed with low-molecular weight agar imparted a feeling of stickiness and sliminess, generated the dirt-like scum, made fingers slippery when the fingers came into contact with moisture again, and showed insufficient storage stability.

The pigment dispersion compositions (Comparative Examples 25 and 29) using agar having a molecular weight exceeding the range of the present invention imparted a feeling of stickiness, showed poor spreadability on the skin, generated dirt, made fingers slippery when the fingers came into contact with moisture, and showed poor storage stability.

The pigment dispersion compositions (Comparative Examples 26 and 30) using the ionic water-soluble polymer showed poor spreadability on the skin, made fingers slippery when the fingers came into contact with moisture, and showed insufficient storage stability.

These results clearly showed that the composition for external use on skin of the present invention in which pigments are dispersed makes it possible to stably disperse pigments, and produces effects such as excellent spreadability on skin and being pleasing to the sense of touch.

Examples 79 to 83 and Comparative Examples 31 to 33

Sunscreen (Production Method)

First, according to the compounding shown in Table 26, all components were weighed and put in a beaker, and mixed and headed at 80° C. to 95° C., and pigments were dispersed by being stirred with a table disper at 5000 rpm. Thereafter, the resultant was slowly cooled while being stirred at 2000 rpm, followed by deaeration under reduced pressure, thereby obtaining pigment dispersion compositions A and B.

Subsequently, according to the compounding shown in Table 27, all components were weighed and put in a beaker, and mixed and headed at 80° C. to 95° C., and the mixture was slowly cooled while being stirred with a table disper mixer at 2000 rpm. The resultant was deaerated under reduced pressure, and the thus obtained sunscreen was taken as a sample.

(Evaluation of Pigment Dispersibility)

The respective samples were stored at 50° C. for a month, and the aggregation and sedimentation of pigments were evaluated respectively according to the same criteria as in Examples 59 to 71.

(Feeling During Use)

0.5 g of the respective samples were applied to the back of hands of a panel consisting of 15 members after the hands were washed, and the feeling during use was surveyed by answers to a questionnaire. The "feeling of stickiness", "spreadability on skin", "dirt generation", "feeling of sliminess", and "re-lubricating property of fingers" were evaluated respectively according to the same criteria as in Examples 1 to 18.

(Water Resistance)

0.5 g of the respective samples were applied to the back of hands of a panel consisting of 15 members after the hands were washed, and the hands were dried. Thereafter, feeling of the pigment dispersion composition remaining on the skin, which was experienced when several drops of water were dripped onto the hand, was evaluated according to the same criteria as in Examples 66 to 78.

TABLE 26

| | Pigment dispersion composition A | (% by mass) Pigment dispersion composition B |
|---|---|---|
| Agar 1 | 1.8 | 1.8 |
| Xanthan gum*[1] | 1.2 | 1.2 |
| Hydrophilic titanium dioxide 1*[2] | 20 | — |
| Hydrophobic titanium dioxide 1*[3] | — | 20 |
| Hydrophilic zinc oxide*[4] | 10 | — |
| Hydrophobic zinc oxide*[5] | — | 10 |
| Deionized water | 67 | 67 |
| Total | 100 | 100 |

*[1]"NOMCORT ZZ" (manufactured by The Nisshin OilliO Group, Ltd.)
*[2]"MT-100WP" (manufactured by TAYCA)
*[3]"MTY-02" (manufactured by TAYCA)
*[4]"Maxlight ZS-64" (manufactured by SHOWA DENKO K.K.)
*[5]"MZ-303S" (manufactured by TAYCA)

TABLE 27

Examples 79 to 83 and Comparative Examples 31 to 33 (Sunscreen)

(% by mass)

| | Example | | | | | Comparative Example | | |
|---|---|---|---|---|---|---|---|---|
| | 79 | 80 | 81 | 82 | 83 | 31 | 32 | 33 |
| Pigment dispersion composition A | 50 | — | — | — | — | — | — | — |
| Pigment dispersion composition B | — | 50 | — | — | — | — | — | — |
| Agar 1 | — | — | 0.6 | 0.9 | 0.9 | 0.9 | — | — |
| Agar 2 | — | — | — | — | — | — | — | 0.9 |
| Xanthan gum*1 | — | — | 0.4 | 0.6 | 0.6 | — | 0.6 | 0.6 |
| Hydrophilic titanium dioxide 1*2 | — | — | 10 | — | — | — | — | — |
| Hydrophobic titanium dioxide 1*3 | — | — | — | 10 | — | 10 | 10 | 10 |
| Hydrophobic titanium dioxide 2*4 | — | — | — | — | 10 | — | — | — |
| Hydrophilic zinc oxide*5 | — | — | 5 | — | — | — | — | — |
| Hydrophobic zinc oxide*6 | — | — | — | 5 | 5 | 5 | 5 | 5 |
| Sodium metaphosphate | 0.01 | 0.01 | 0.01 | 0.01 | 0.01 | 0.01 | 0.01 | 0.01 |
| Deionized water | 34.79 | 21.79 | 68.79 | 55.29 | 55.29 | 55.89 | 56.19 | 55.29 |
| Glycerin | 3 | 3 | 3 | 3 | 3 | 3 | 3 | 3 |
| 1,3-butylene glycol | 10 | 5 | 10 | 5 | 5 | 5 | 5 | 5 |
| Methylparaben | 0.15 | 0.15 | 0.15 | 0.15 | 0.15 | 0.15 | 0.15 | 0.15 |
| Propylparaben | 0.05 | 0.05 | 0.05 | 0.05 | 0.05 | 0.05 | 0.05 | 0.05 |
| Erythrityl triethylhexanoate*7 | 2 | 10 | 2 | 10 | 10 | 10 | 10 | 10 |
| Dimethicone*8 | — | 10 | — | 10 | 10 | 10 | 10 | 10 |
| Total | 100 | 100 | 100 | 100 | 100 | 100 | 100 | 100 |
| Aggregation of pigment | O | O | O | O | O | O | O | O |
| Sedimentation of pigment | O | O | O | O | O | X | O | O |
| Feeling of stickiness | A | A | A | A | A | C | D | D |
| Spreadability on skin | A | A | B | B | B | C | C | D |
| Dirt generation | A | A | B | B | B | B | C | C |
| Feeling of sliminess | A | A | A | A | A | A | D | C |
| Re-lubricating property of fingers | A | A | A | A | A | B | C | D |
| Water resistance | B | A | B | A | A | B | B | B |

*1 "NOMCORT ZZ" (manufactured by The Nisshin OilliO Group, Ltd.)
*2 "MT-100WP" (manufactured by TAYCA)
*3 "MTY-02" (manufactured by TAYCA)
*4 "MTY-100TV" (manufactured by TAYCA)
*5 "Maxlight ZS-64" (manufactured by SHOWA DENKO K.K.)
*6 "MZ-303S" (manufactured by TAYCA)
*7 "SALACOS E-38" (manufactured by The Nisshin OilliO Group, Ltd.)
*8 "KF96-6cs" (manufactured by Shin-Etsu Chemical Co., Ltd.)

Pigment dispersibility, feeling during use, and water resistance were evaluated in the same manner as in Examples 66 to 78.

As a result, all of the sunscreens of Examples 79 to 83 using the composition for external use on skin of the present invention were excellent since they did not impart a feeling of stickiness or sliminess, were spread excellently on the skin, did not generate the dirt-like scum, and did not make fingers slippery even when the fingers came into contact with moisture again. Furthermore, even when these compositions for external use on skin were stored at 50° C. for a month, aggregation and sedimentation of pigments were not observed, and pigment dispersibility was excellent, that is, storage stability was excellent. Among the compositions, Examples 80, 82, and 83 using hydrophobic pigments showed markedly excellent water resistance. In addition, all of Examples 79 and 80 using the pigment dispersion compositions A and B as the composition for external use on skin of the present invention were spread markedly excellently on the skin and did not generate dirt.

On the other hand, the pigment dispersion composition (Comparative Example 40) not mixed with xanthan gum imparted a feeling of stickiness, was spread insufficiently on the skin, and showed poor storage stability.

The sunscreen (Comparative Example 32) using a composition for external use on skin that was not mixed with a low-molecular weight agar imparted a feeling of stickiness and sliminess, generated the dirt-like scum, made finger slippery when the fingers came into contact with moisture again, and showed insufficient storage stability. Moreover, the sunscreen (Comparative Example 33) using the composition for external use on skin that used agar having a molecular weight exceeding the range of the present invention imparted a feeling of stickiness, was not spread excellently on the skin, generated dirt, made fingers slippery when the fingers came into contact with moisture, and showed poor storage stability.

These results clearly shows that the composition for external use on skin of the present invention in which pigments are dispersed produces effects in which the pigments can be stably dispersed, and the composition spreads excellently on the skin and is pleasing to the sense of touch.

Examples 84 to 93 and Comparative Examples 34 to 38

Cleaning Agent Composition (Production Method)

According to the compounding shown in Tables 28 and 29, all components were weighed and put in a beaker, and mixed and dissolved by being heated at 80° C. to 95° C., and the mixture was slowly cooled while being stirred with a table disper mixer at 1000 rpm. The resultant was deaerated under reduced pressure, and the thus obtained cleaning agent composition was taken as a sample. In Tables 28 and 29, "cocamidopropyl betaine" and "lauryl betaine" are amphoteric surfactants, "potassium cocoyl glycine" and "sodium lauroyl glutamate" are anionic surfactants, and "decyl glucoside" is a nonionic surfactant. In addition, "carbomer" is an ionic water-soluble polymer. When commercially available products were used as surfactants, each of the products were mixed respectively such that the amount of active ingredients (surfactants themselves) mixed become the amount described in Tables 28 and 29.

(Feeling During Use)

0.5 g of the respective samples were applied to palms of a panel consisting of 15 members after the palms were wet with water, and the feeling during use was surveyed by answers to a questionnaire and evaluated according to the following criteria. Feeling during use during application was evaluated by "Foaming", "foam retainability", "dripping", and "sense of touch". In addition, "easiness of rinse" was used to evaluate the sense of touch at the time when the cleaning agent composition was rinsed off with running water.

[Foaming]
A: 12 or more people answered that foaming was excellent.
B: 8 to 11 people answered that foaming was excellent.
C: 4 to 7 people answered that foaming was excellent.
D: 3 or less people answered that foaming was excellent.

[Foam Retainability]
A: 12 or more people answered that foam retainability was excellent.
B: 8 to 11 people answered that foam retainability was excellent.
C: 4 to 7 people answered that foam retainability was excellent.
D: 3 or less people answered that foam retainability was excellent.

[Dripping]
A: 12 or more people answered that dripping was not caused and usability was excellent.
B: 8 to 11 people answered that dripping was not caused and usability was excellent.
C: 4 to 7 people answered that dripping was not caused and usability was excellent.
D: 3 or less people answered that dripping was not caused and usability was excellent.

[Feeling During Use]
A: 12 or more people answered that the composition was not sticky and slimy and feeling during use was excellent.
B: 8 to 11 people answered that the composition was not sticky and slimy and feeling during use was excellent.
C: 4 to 7 people answered that the composition was not sticky and slimy and feeling during use was excellent.
D: 3 or less people answered that the composition was not sticky and slimy and feeling during use was excellent.

[Easiness of Rinse]
A: 12 or more people answered that the composition was easily rinsed off and there was no residues.
B: 8 to 11 people answered that the composition was easily rinsed off and there was no residues.
C: 4 to 7 people answered that the composition was easily rinsed off and there was no residues.
D: 3 or less people answered that the composition was easily rinsed off and there was no residues.

[Irritating Properties]
A: 12 or more people answered that they didn't feel skin irritation.
B: 8 to 11 people answered that they didn't feel skin irritation.
C: 4 to 7 people answered that they didn't feel skin irritation.
D: 3 or less people answered that they didn't feel skin irritation.

(Storage Stability)

The respective samples were stored at 50° C. for a month, and then the degree of water separation, oil separation, and creaming was evaluated respectively by visual observation according to the same criteria as in Examples 1 to 18.

TABLE 28

Examples 84 to 93 (Cleaning Agent Composition)

(% by mass)

| | Example | | | | | | | | | |
|---|---|---|---|---|---|---|---|---|---|---|
| | 84 | 85 | 86 | 87 | 88 | 89 | 90 | 91 | 92 | 93 |
| Agar 1 | 0.9 | 0.9 | 0.9 | 0.9 | 0.9 | 0.9 | 0.9 | 0.45 | 3 | 4.8 |
| Agar 2 | — | — | — | — | — | — | — | — | — | — |
| Xanthan gum*[1] | 0.6 | 0.6 | 0.6 | 0.6 | 0.6 | 0.6 | 0.6 | 0.3 | 2 | 3.2 |
| Carbomer*[2] | — | — | — | — | — | — | — | — | — | — |
| Sodium hydroxide | — | — | — | — | — | — | — | — | — | — |
| Cocamidopropyl betaine*[3] | 5 | 20 | — | — | — | — | — | 20 | 20 | 20 |
| Cocobetaine*[4] | — | — | 35 | — | — | — | — | — | — | — |
| Lauryl betaine*[5] | — | — | — | 20 | — | — | — | — | — | — |
| Potassium cocoyl glycine*[6] | — | — | — | — | 20 | — | — | — | — | — |
| Sodium lauroyl glutamate*[7] | — | — | — | — | — | 20 | — | — | — | — |

TABLE 28-continued

Examples 84 to 93 (Cleaning Agent Composition)

| | Example | | | | | | | | | | (% by mass) |
|---|---|---|---|---|---|---|---|---|---|---|---|
| | 84 | 85 | 86 | 87 | 88 | 89 | 90 | 91 | 92 | 93 | |
| Decyl glucoside*8 | — | — | — | — | — | — | 20 | — | — | — | |
| Glycol distearate*9 | 2 | 2 | 2 | 2 | 2 | 2 | 2 | 2 | 2 | 2 | |
| Water | 91.5 | 76.5 | 61.5 | 76.5 | 76.5 | 76.5 | 76.5 | 77.2 | 73 | 70 | |
| Total | 100.0 | 100.0 | 100.0 | 100.0 | 100.0 | 100.0 | 100.0 | 100.0 | 100.0 | 100.0 | |
| Foaming | B | A | A | A | A | A | A | A | B | B | |
| Foam retainability | B | A | A | A | A | A | A | A | A | A | |
| Dripping | A | A | A | A | A | A | A | A | A | A | |
| Touch | A | A | A | A | B | B | B | A | B | B | |
| Easiness of rinse | A | A | A | A | B | B | B | A | B | B | |
| Irritating properties | A | A | B | A | B | B | B | A | A | A | |
| Storage stability | B | B | B | B | B | B | B | B | B | B | |

TABLE 29

Comparative Examples 34 to 38 (Cleaning Agent Composition)

| | Comparative Example | | | | | (% by mass) |
|---|---|---|---|---|---|---|
| | 34 | 35 | 36 | 37 | 38 | |
| Agar 1 | — | 1.5 | — | — | — | |
| Agar 2 | — | — | — | 0.9 | — | |
| Xanthan gum*1 | — | — | 1.5 | 0.6 | — | |
| Carbomer*2 | — | — | — | — | 0.2 | |
| Sodium hydroxide | — | — | — | — | 0.06 | |
| Cocamidopropyl betaine*3 | 20 | 20 | 20 | 20 | 20 | |
| Cocobetaine*4 | — | — | — | — | — | |
| Lauryl betaine*5 | — | — | — | — | — | |
| Potassium cocoyl glycine*6 | — | — | — | — | — | |
| Sodium lauroyl glutamate*7 | — | — | — | — | — | |
| Decyl glucoside*8 | — | — | — | — | — | |
| Glycol distearate*9 | 2 | 2 | 2 | 2 | 2 | |
| Water | 78 | 76.5 | 76.5 | 76.5 | 77.74 | |
| Total | 100.0 | 100.0 | 100.0 | 100.0 | 100.0 | |
| Foaming | D | B | C | C | C | |
| Foam retainability | D | D | B | B | D | |
| Dripping | D | D | B | B | D | |
| Touch | C | B | D | D | C | |
| Easiness of rinse | B | C | D | D | B | |
| Irritating properties | B | A | A | A | C | |
| Storage stability | D | D | B | B | D | |

*1"NOMCORT ZZ" (manufactured by The Nisshin OilliO Group, Ltd.)
*2"Carbopol 940" (manufactured by Lubrizol Advanced Materials)
*3"Lebon 2000HG" (manufactured by Sanyo Chemical Industries, Ltd.), active ingredient: 30%
*4"Obazoline BC" (manufactured by TOHO Chemical Industry Co., LTD.), active ingredient: 40%
*5"Amphitol 24B" (manufactured by KAO Corporation), active ingredient: 27%
*6"Amilite GCK-11" (manufactured by AJINOMOTO HEALTHY SUPPLLY, INC.)
*7"Amisoft LS-11" (manufactured by AJINOMOTO HEALTHY SUPPLLY, INC.)
*8"Mydol 10" (manufactured by KAO Corporation), active ingredient: 40%
*9"Emanon 3201M" (manufactured by KAO Corporation)

As a result, the cleaning agent compositions of Examples 84 to 93 as the composition for external use on skin of the present invention were excellent in foaming, foam retainability, and touch, did not drip, and could be easily rinsed off. In addition, even when these cleaning agent compositions were stored at 50° C. for a month, sedimentation of solids was not observed, and storage stability was excellent. Among these compositions, Examples 84 to 87 and Examples 91 to 93 using amphoteric surfactants were not irritating and showed high safety.

On the other hand, the cleaning agent composition (Comparative Example 34) not mixed with a thickener was poor in foaming, foam retainability, and usability, and showed insufficient storage stability.

The cleaning agent composition (Comparative Example 35) not mixed with xanthan gum was poor in foam retainability and usability and showed insufficient storage stability.

The cleaning agent composition (Comparative Example 36) not mixed with low-molecular weight agar imparted a feeling stickiness and sliminess and could not be easily rinsed off.

The cleaning agent composition (Comparative Example 37) using agar having a molecular weight exceeding the range of the present invention imparted a feeling of stickiness and sliminess and could not be easily rinsed off.

The cleaning agent composition (Comparative Example 38) using an ionic water-soluble polymer was poor in foam retainability and usability and showed insufficient storage stability.

These results clearly show that the composition for external use on skin of the present invention containing the surfactant as the component (F) has sufficient viscosity, is excellent in usability, touch, and storage stability, and is suitable as a cleaning agent or a cleaning agent composition.

Examples 94 to 96 and Comparative Examples 39 to 41

Shampoo (Production Method)

First, according to the compounding shown in Table 30, all components were weighed and put in a beaker, and mixed and heated at 80° C. to 95° C., and the mixture was slowly cooled while being stirred with a table disper at 1000 rpm. The resultant was deaerated under reduced pressure, thereby obtaining cleaning agent compositions A to F. When commercially available products were used as surfactants, each of the products was mixed respectively such that the amount of active ingredients (surfactants themselves) mixed become the amount described in Table 30.

Subsequently, according to the compounding shown in Table 31, all components were weighed and put in a beaker, and mixed and dissolved by being heated at 80° C. to 95° C., and the resultant was slowly cooled while being stirred with a table disper mixer at 1000 rpm. The resultant was deaerated under reduced pressure, and the thus obtained shampoo was taken as a sample.

(Feeling During Use)

Each sample was applied to the whole hair of a panel consisting of 15 members after the hair was wet with water, and the feeling during use was surveyed by answers to a questionnaire. The "foaming", "foam retainability", "dripping", "feeling during use", "easiness of rinse", and "irritating properties" were evaluated according to the same criteria as in Examples 84 to 93, and "spreadability on hair" was evaluated according to the following criteria, respectively. The "foaming", "foam retainability", "dripping", "feeling during use", and "spreadability on hair" were used to evaluate the feeling during use during application, and "easiness of rinse" was used to evaluate the sense of touch at the time when the sample was rinsed off.

[Spreadability on Hair]

A: 12 or more people answered that the shampoo could be easily spread on hair and feeling during use was excellent.

B: 8 to 11 people answered that the shampoo could be easily spread on hair and feeling during use was excellent.

C: 4 to 7 people answered that the shampoo could be easily spread on hair and feeling during use was excellent.

D: 3 or less people answered that the shampoo could be easily spread on hair and feeling during use was excellent.

(Storage Stability)

The respective samples were stored at 50° C. for a month, and then the degree of water separation, oil separation, and creaming was evaluated respectively by visual observation according to the same criteria as in Examples 1 to 18.

TABLE 30

| | \multicolumn{6}{c}{Cleaning agent composition (% by mass)} | | | | | |
|---|---|---|---|---|---|---|
| | A | B | C | D | E | F |
| Agar 1 | 0.9 | 0.9 | 0.9 | 1.5 | — | — |
| Agar 2 | — | — | — | — | — | 0.9 |
| Xanthan gum*1 | 0.6 | 0.6 | 0.6 | — | 1.5 | 0.6 |
| Cocamidopropyl betaine*2 | 15 | — | — | 15 | 15 | 15 |
| Potassium cocoyl glycine*3 | — | 15 | — | — | — | — |
| Decyl glucoside*4 | — | — | 15 | — | — | — |
| Water | 83.5 | 83.5 | 83.5 | 83.5 | 83.5 | 83.5 |
| Total | 100 | 100 | 100 | 100 | 100 | 100 |

*1"NOMCORT ZZ" (manufactured by The Nisshin OilliO Group, Ltd.)
*2"Lebon 2000HG" (manufactured by Sanyo Chemical Industries, Ltd.), active ingredient: 30%
*3"Amilite GCK-11" (manufactured by AJINOMOTO HEALTHY SUPPLLY, INC.)
*4"Mydol 10" (manufactured by KAO Corporation), active ingredient: 40%

TABLE 31

Examples 94 to 96 and Comparative Examples 39 to 41 (Shampoo)

(% by mass)

| | Example | | | Comparative Example | | |
|---|---|---|---|---|---|---|
| | 94 | 95 | 96 | 39 | 40 | 41 |
| Cleaning agent composition A | 50 | — | — | — | — | — |
| Cleaning agent composition B | — | 50 | — | — | — | — |
| Cleaning agent composition C | — | — | 50 | — | — | — |
| Cleaning agent composition D | — | — | — | 50 | — | — |
| Cleaning agent composition E | — | — | — | — | 50 | — |
| Cleaning agent composition F | — | — | — | — | — | 50 |
| Ethylene glycol distearate*1 | 2 | 2 | 2 | 2 | 2 | 2 |
| Glycerin | 5 | 5 | 5 | 5 | 5 | 5 |
| Methylparaben | 0.2 | 0.2 | 0.2 | 0.2 | 0.2 | 0.2 |
| Propylparaben | 0.05 | 0.05 | 0.05 | 0.05 | 0.05 | 0.05 |
| EDTA-2Na | 0.01 | 0.01 | 0.01 | 0.01 | 0.01 | 0.01 |
| Poly-quaternium-10*2 | 0.5 | 0.5 | 0.5 | 0.5 | 0.5 | 0.5 |
| Deionized water | 42.24 | 42.24 | 42.24 | 42.24 | 42.24 | 42.24 |
| Total | 100.0 | 100.0 | 100.0 | 100.0 | 100.0 | 100.0 |
| Foaming | A | A | B | C | B | C |
| Foam retainability | A | A | B | D | B | B |
| Dripping | A | A | A | D | A | A |
| Feeling during use | A | A | B | B | D | D |
| Spreadability on hair | A | A | B | C | D | D |
| Easiness of rinse | A | B | B | B | C | C |
| Irritating properties | A | B | B | A | A | C |
| Storage stability | B | B | B | D | B | B |

*1"Emanon 3201M" (manufactured by KAO Corporation)
*2"UCARE Polymer JR-400" (manufactured by Dow Chemical Company Japan)

As a result, all of the samples of Examples 94 to 96 mixed with the cleaning agent composition as the composition for external use on skin of the present invention were excellent in foaming and foam retainability, did not drip, did not impart a feeling of stickiness or sliminess, and were spread excellently on hair. In addition, even when these samples were stored at 50° C. for a month, sedimentation of solids was not observed, and storage stability was excellent. Among the samples, Example 94 using amphoteric surfactants was less irritating to the skin.

On the other hand, the sample (Comparative Example 39) mixed with the cleaning agent composition D not mixed with xanthan gum showed insufficient storage stability and dripped due to low viscosity, so foam retainability was not excellent.

The sample (Comparative Example 40) mixed with the cleaning agent composition E not mixed with low-molecular weight agar and the sample (Comparative Example 41) mixed with the cleaning agent composition F using agar having a molecular weight exceeding the range of the present invention imparted a feeling of stickiness and sliminess and were spread poorly on hair.

These results clearly show that the composition for external use on skin of the present invention containing the surfactant as the component (F) has sufficient viscosity, is excellent in usability and pleasing to the sense of touch, shows excellent storage stability, and is suitable as a cleaning agent or a cleaning agent composition.

Examples 97 to 99 and Comparative Examples 42 to 46

Baby Shampoo (Production Method)

According to the compounding shown in Table 32, all components were weighed and put in a beaker, and mixed and dissolved by being heated at 80° C. to 95° C., and the mixture was slowly cooled while being stirred with a table disper mixer at 1000 rpm. The resultant was deaerated under reduced pressure, and the thus obtained baby shampoo was taken as a sample. When commercially available products were used as surfactants, each of the products was mixed respectively such that the amount of active ingredient (surfactants themselves) mixed become the amount described in Table 32.

(Feeling During Use)

The "foaming", "foam retainability", "dripping", "feeling during use", "easiness of rinse", irritating properties", and "spreadability on hair" of the respective samples were evaluated respectively according to the same criteria as in Examples 94 to 96.

(Storage Stability)

The respective samples were stored at 50° C. for a month, and then the degree of water separation, oil separation, and creaming was evaluated respectively by visual observation according to the same criteria as in Examples 1 to 18.

As a result, all of the samples of Examples 97 to 99 as the composition for external use on skin of the present invention were excellent in foaming and foam retainability, did not drip, did not impart a feeling of stickiness or sliminess, and were spread excellently on hair. Moreover, even when these samples were stored at 50° C. for a month, sedimentation of solids was not observed, and storage stability was excellent. Among the samples, Example 97 using only amphoteric surfactants was less irritating to the skin.

On the other hand, the sample (Comparative Example 42) not mixed with a thickener, the sample (Comparative Example 43) not mixed with xanthan gum, and the sample (Comparative Example 46) using an ionic water-soluble polymer were poor in foaming since these samples dripped due to low viscosity and not pleasant to the sense of touch when used due to large crystals of solid contents. In addition, when these samples were stored at 50° C. for a month, the solid contents were precipitated, so storage stability was insufficient.

The sample (Comparative Example 44) not mixed with low-molecular weight agar and the cleaning agent composition (Comparative Example 45) using agar having a molecular weight exceeding the range of the present invention imparted a feeling of stickiness and sliminess and were spread poorly on hair.

These results also clearly show that the composition for external use on skin of the present invention containing the surfactant as the component (F) has sufficient viscosity, is excellent in usability and pleasing to the sense of touch,

TABLE 32

Examples 97 to 99 and Comparative Examples 42 to 46 (Baby Shampoo)

(% by mass)

|  | Example | | | Comparative Example | | | | |
| --- | --- | --- | --- | --- | --- | --- | --- | --- |
|  | 97 | 98 | 99 | 42 | 43 | 44 | 45 | 46 |
| Agar 1 | 0.45 | 0.45 | 0.45 | — | 0.75 | — | — | — |
| Agar 2 | — | — | — | — | — | — | 0.45 | — |
| Xanthan gum*1 | 0.3 | 0.3 | 0.3 | — | — | 0.75 | 0.3 | — |
| Carbomer*2 | — | — | — | — | — | — | — | 0.1 |
| Sodium hydroxide | — | — | — | — | — | — | — | 0.03 |
| Cocamidopropyl betaine*3 | 6 | 6 | 6 | 6 | 6 | 6 | 6 | 6 |
| Decyl glucoside*4 | 2.24 | 2.24 | — | 2.24 | 2.24 | 2.24 | 2.24 | 2.24 |
| Polyquaternium-10*5 | 0.5 | — | — | — | — | — | — | — |
| Hydroxyethyl urea*6 | — | 5 | 5 | 5 | 5 | 5 | 5 | 5 |
| Glycerin | 5 | 5 | 5 | 5 | 5 | 5 | 5 | 5 |
| Methylparaben | 0.2 | 0.2 | 0.2 | 0.2 | 0.2 | 0.2 | 0.2 | 0.2 |
| Propylparaben | 0.05 | 0.05 | 0.05 | 0.05 | 0.05 | 0.05 | 0.05 | 0.05 |
| EDTA-2Na | 0.01 | 0.01 | 0.01 | 0.01 | 0.01 | 0.01 | 0.01 | 0.01 |
| Deionized water | 85.25 | 80.75 | 82.99 | 81.5 | 80.75 | 80.7 | 80.7 | 81.37 |
| Total | 100 | 100 | 100 | 100 | 100 | 100 | 100 | 100 |
| Foaming | A | A | A | D | C | C | C | C |
| Foam retainability | A | A | A | D | D | B | B | D |
| Dripping | A | A | A | D | D | A | A | D |
| Feeling during use | A | A | A | D | D | D | D | D |
| Spreadability on hair | A | A | A | C | C | D | D | D |
| Easiness of rinse | A | A | A | B | B | C | D | B |
| Irritating properties | B | B | A | B | B | B | B | B |
| Storage stability | B | B | B | D | D | B | B | D |

*1"NOMCORT ZZ" (manufactured by The Nisshin OilliO Group, Ltd.)
*2"Carbopol 940" (manufactured by Lubrizol Advanced Materials)
*3"Lebon 2000HG" (manufactured by Sanyo Chemical Industries, Ltd.), active ingredient: 30%
*4"Mydol 10" (manufactured by KAO Corporation), active ingredient: 40%
*5"UCARE Polymer JR-400" (manufactured by Dow Chemical Company Japan)
*6"Hydrovance" (manufactured by AkzoNobel N.V.)

shows excellent storage stability, and is suitable as a cleaning agent or a cleaning agent composition.

Example 100 and Comparative Examples 47 to 50

Shampoo (Production Method)

According to the compounding shown in Table 33, all components were weighed and put in a beaker, and mixed and dissolved by being heated at 80° C. to 95° C., and the mixture was slowly cooled while being stirred with a table disper mixer at 1000 rpm. The resultant was deaerated under reduced pressure, and the thus obtained shampoo was taken as a sample. When commercially available products were used as surfactants, each of the products was mixed respectively such that the amount of active ingredients (surfactants themselves) mixed become the amount described in Table 33.

(Feeling During Use)

The "foaming", "foam retainability", "dripping", "feeling during use", "easiness of rinse", "irritating properties", and "spreadability on hair" of the respective samples were evaluated respectively according to the same criteria as in Examples 94 to 96.

(Storage Stability)

The respective samples were stored at 50° C. for a month, and then the degree of water separation, oil separation, and creaming was evaluated respectively by visual observation according to the same criteria as in Examples 1 to 18.

TABLE 33

Example 100 and Comparative Examples 47 to 50 (Shampoo)

|  | Example | Comparative Example | | | (% by mass) |
|---|---|---|---|---|---|
|  | 100 | 47 | 48 | 49 | 50 |
| Agar 1 | 0.45 | 0.75 | — | — | — |
| Agar 2 | — | — | — | 0.45 | — |
| Xanthan gum*1 | 0.3 | — | 0.75 | 0.3 | — |
| Carbomer*2 | — | — | — | — | 0.1 |
| Sodium hydroxide | — | — | — | — | 0.03 |
| TEA laureth sulfate*3 | 3 | 3 | 3 | 3 | 3 |
| Sodium laureth sulfate*4 | 6 | 6 | 6 | 6 | 6 |
| Sodium lauryl sulfate*5 | 1.5 | 1.5 | 1.5 | 1.5 | 1.5 |
| Cocamide DEA (1:2)*6 | 3 | 3 | 3 | 3 | 3 |
| Lauryl betaine*7 | 2.45 | 2.45 | 2.45 | 2.45 | 2.45 |
| Glycol distearate*8 | 2 | 2 | 2 | 2 | 2 |
| Glycerin | 5 | 5 | 5 | 5 | 5 |
| Methylparaben | 0.2 | 0.2 | 0.2 | 0.2 | 0.2 |
| Propylparaben | 0.05 | 0.05 | 0.05 | 0.05 | 0.05 |
| EDTA-2Na | 0.01 | 0.01 | 0.01 | 0.01 | 0.01 |
| Deionized water | 76.04 | 76.04 | 76.04 | 76.04 | 76.66 |
| Total | 100 | 100 | 100 | 100 | 100 |
| Foaming | A | C | C | C | C |
| Foam retainability | A | D | B | B | D |
| Dripping | A | D | A | A | D |
| Feeling during use | A | D | D | C | D |
| Spreadability on hair | A | C | C | C | D |
| Easiness of rinse | A | B | D | D | B |

TABLE 33-continued

Example 100 and Comparative Examples 47 to 50 (Shampoo)

|  | Example | Comparative Example | | | (% by mass) |
|---|---|---|---|---|---|
|  | 100 | 47 | 48 | 49 | 50 |
| Irritating properties | B | B | B | B | C |
| Storage stability | B | D | B | B | D |

*1"NOMCORT ZZ" (manufactured by The Nisshin OilliO Group, Ltd.)
*2"Carbopol 940" (manufactured by Lubrizol Advanced Materials)
*3"Emal 20T" (manufactured by KAO Corporation), active ingredient: 40%
*4"Emal 20C" (manufactured by KAO Corporation), active ingredient: 25%
*5"Emal 10PT" (manufactured by KAO Corporation), active ingredient: 94%
*6"Amizol CD" (manufactured by Kawaken Fine Chemicals Co., Ltd.)
*7"Amphitol 24B" (manufactured by KAO Corporation), active ingredient: 27%
*8"Emanon 3201M" (manufactured by KAO Corporation)

As a result, the sample of Example 100 as the composition for external use on skin of the present invention was excellent in foaming and foam retainability, did not drip, did not impart a feeling of stickiness or sliminess, and was spread excellently on hair. In addition, when the sample was stored at 50° C. for a month, sedimentation of solids was not observed, and storage stability was excellent.

On the other hand, the sample (Comparative Example 47) not mixed with xanthan gum and the sample (Comparative Example 50) using an ionic water-soluble polymer were not excellent in foaming since these samples dripped due to low viscosity and were not pleasant to the sense of touch when used since crystals of the solid contents were large. In addition, when these samples were stored at 50° C. for a month, the solid contents were precipitated, so storage stability was insufficient.

The sample (Comparative Example 48) not mixed with low-molecular weight agar and the cleaning agent composition (Comparative Example 49) using agar having a molecular weight exceeding the range of the present invention imparted a feeling of stickiness and sliminess and were not spread on hair.

Example 101 and Comparative Examples 51 to 54

Body Shampoo (Production Method)

According to the compounding shown in Table 34, all components were weighed and put in a beaker, and mixed and dissolved by being heated at 80° C. to 95° C., and the mixture was slowly cooled while being stirred with a table disper mixer at 1000 rpm. The resultant was deaerated under reduced pressure, and the thus obtained body shampoo was taken as a sample. When commercially available products were used as surfactants, each of the products was mixed respectively such that the amount of active ingredients (surfactants themselves) mixed become the amount described in Table 34.

(Feeling During Use)

The "foaming", "foam retainability", "dripping", "feeling during use", "easiness of rinse", and "irritating properties" of the respective samples were evaluated according to the same criteria as in Examples 94 to 96, and "spreadability on skin" was evaluated according to the same criteria as in Example 1 to 18, respectively.

(Storage Stability)

The respective samples were stored at 50° C. for a month, and then the degree of water separation, oil separation, and creaming was evaluated respectively by visual observation according to the same criteria as in Examples 1 to 18.

TABLE 34

Example 101 and Comparative Examples 51 to 54 (Body Shampoo)

|  | Example | Comparative Example | | | (% by mass) |
|---|---|---|---|---|---|
|  | 101 | 51 | 52 | 53 | 54 |
| Agar 1 | 1.2 | 2 | — | — | — |
| Agar 2 | — | — | — | 1.2 | — |
| Xanthan gum*1 | 0.8 | — | 2 | 0.8 | — |
| Carbomer*2 | — | — | — | — | 0.2 |
| Sodium hydroxide | — | — | — | — | 0.06 |
| Potassium laurate*3 | 8 | 8 | 8 | 8 | 8 |
| Potassium myristate*4 | 1.5 | 1.5 | 1.5 | 1.5 | 1.5 |
| Potassium palmitate*5 | 1.5 | 1.5 | 1.5 | 1.5 | 1.5 |
| Cocamide DEA*6 | 1 | 1 | 1 | 1 | 1 |
| Lauryl betaine*7 | 3 | 3 | 3 | 3 | 3 |
| Glycol distearate*8 | 1 | 1 | 1 | 1 | 1 |
| Glycerin | 5 | 5 | 5 | 5 | 5 |
| Methylparaben | 0.2 | 0.2 | 0.2 | 0.2 | 0.2 |
| Propylparaben | 0.05 | 0.05 | 0.05 | 0.05 | 0.05 |
| EDTA-2Na | 0.01 | 0.01 | 0.01 | 0.01 | 0.01 |
| Deionized water | 76.74 | 76.74 | 76.74 | 76.74 | 78.48 |
| Total | 100 | 100 | 100 | 100 | 100 |
| Foaming | A | C | C | C | C |
| Foam retainability | A | D | B | B | D |
| Dripping | A | D | A | A | D |
| Feeling during use | A | D | D | C | D |
| Spreadability on skin | A | C | C | B | C |
| Easiness of rinse | A | A | D | D | B |
| Irritating properties | B | B | B | B | C |
| Storage stability | B | D | B | B | D |

*1"NOMCORT ZZ" (manufactured by The Nisshin OilliO Group, Ltd.)
*2"Carbopol 940" (manufactured by Lubrizol Advanced Materials)
*3"Nonsoul LK-2" (manufactured by NOF CORPORATION),
*4"Nonsoul MK-1" (manufactured by NOF CORPORATION),
*5"Nonsoul PK-1" (manufactured by NOF CORPORATION),
*6"Amicol CDE-1" (manufactured by MIYOSHI OIL & FAT CO., LTD)
*7"Amphitol 24B" (manufactured by KAO Corporation), active ingredient: 27%
*8"Emanon 3201M" (manufactured by KAO Corporation)

As a result, the sample of Example 101 as the composition for external use on skin of the present invention was excellent in foaming and foam retainability, did not drip, was excellently pleasing to the sense of touch when used, and was spread excellently on the skin. Furthermore, even when this sample was stored at 50° C. for a month, sedimentation of solids was not observed, and storage stability was excellent.

On the other hand, the sample (Comparative Example 51) not mixed with xanthan gum and the sample (Comparative Example 54) using an ionic water-soluble polymer were not excellent in foaming since these samples dripped due to low viscosity and were unpleasing to the sense of touch when used since crystals of solid contents were large. When these samples were stored at 50° C. for a month, the solid contents were precipitated, so storage stability was insufficient.

The sample (Comparative Example 52) not mixed with low-molecular weight agar and the cleaning agent composition (Comparative Example 53) using agar having a molecular weight exceeding the range of the present invention imparted a feeling of stickiness and sliminess and were not easily rinsed off.

Examples 102 and Comparative Examples 55 to 58

Facial Cleanser (Production Method)

According to the compounding shown in Table 35, all components were weighed and put in a beaker, and mixed and dissolved by being heated at 80° C. to 95° C., and the mixture was slowly cooled while being stirred with a table disper mixer at 1000 rpm. The resultant was deaerated under reduced pressure, and the thus obtained facial cleanser was taken as a sample. When commercially available products were used as surfactants, each of the products was mixed respectively such that the amount of active ingredients (surfactants themselves) mixed become the amount described in Table 35.

(Feeling During Use)

The "foaming", "foam retainability", "dripping", "feeling during use", "easiness of rinse", and "irritating properties" of the respective samples were evaluated according to the same criteria as in Examples 94 to 96, and "spreadability on skin" was evaluated according to the same criteria as in Example 1 to 18, respectively.

(Storage Stability)

The respective samples were stored at 50° C. for a month, and then the degree of water separation, oil separation, and creaming was evaluated respectively by visual observation according to the same criteria as in Examples 1 to 18.

TABLE 35

Example 102 and Comparative Examples 55 to 58 (Facial Cleanser)

|  | Example | Comparative Example | | | (% by mass) |
|---|---|---|---|---|---|
|  | 102 | 55 | 56 | 57 | 58 |
| Agar 1 | 0.9 | 1.5 | — | — | — |
| Agar 2 | — | — | — | 0.9 | — |
| Xanthan gum*1 | 0.6 | — | 1.5 | 0.6 | — |
| Carbomer*2 | — | — | — | — | 0.2 |
| Sodium hydroxide | — | — | — | — | 0.06 |
| Glycerin | 10 | 10 | 10 | 10 | 10 |
| Lauryl betaine*3 | 2 | 2 | 2 | 2 | 2 |
| Cocamide DEA*4 | 10 | 10 | 10 | 10 | 10 |
| Methylparaben | 0.2 | 0.2 | 0.2 | 0.2 | 0.2 |
| Propylparaben | 0.05 | 0.05 | 0.05 | 0.05 | 0.05 |
| Deionized water | 76.25 | 76.25 | 76.25 | 76.25 | 77.49 |
| Total | 100 | 100 | 100 | 100 | 100 |
| Foaming | A | C | C | C | C |
| Foam retainability | A | D | B | B | D |
| Dripping | A | D | A | A | D |
| Feeling during use | A | D | D | C | D |
| Spreadability on skin | A | C | C | B | C |
| Easiness of rinse | A | A | D | D | B |
| Irritating properties | B | B | B | B | C |

*1"NOMCORT ZZ" (manufactured by The Nisshin OilliO Group, Ltd.)
*2"Carbopol 940" (manufactured by Lubrizol Advanced Materials)
*3"Amphitol 24B" (manufactured by KAO Corporation), active ingredient: 27%
*4"Amicol CDE-1" (manufactured by MIYOSHI OIL & FAT CO., LTD)

As a result, the sample of Example 102 as the composition for external use on skin of the present invention was excellent in foaming and foam retainability, did not drip, was excellently pleasing to the sense of touch when used, and was spread excellently on the skin. Furthermore, even when this sample was stored at 50° C. for a month, sedimentation of solids was not observed, so the storage stability was excellent.

On the other hand, the sample (Comparative Example 55) not mixed with xanthan gum and the sample (Comparative Example 58) using an ionic water-soluble polymer were poor in foaming since these samples dripped due to low viscosity and were not pleasant to the sense of touch when used since crystals of the solid contents were large. In addition, when these samples were stored at 50° C. for a month, the solid contents were precipitated, so storage stability was insufficient.

The sample (Comparative Example 56) not mixed with low-molecular weight agar and the cleaning agent composition (Comparative Example 57) using agar having a molecular weight exceeding the range of the present invention imparted a feeling of stickiness and sliminess and were not easily rinsed off.

Examples 103 to 106

Production Method

According to the compounding shown in Table 36, all components were weighed and put in a beaker, and mixed and heated at 80° C. to 95° C., and the mixture was slowly cooled while being stirred with a table disper mixer at 2000 rpm. The resultant was deaerated under reduced pressure, and the thus obtained composition for external use on skin was taken as a sample.

(Feeling During Use)

0.5 g of the respective samples were applied to the back of hands of a panel consisting of 15 members after the hands were washed, and the feeling during use was surveyed by answers to a questionnaire. The "dirt generation" was evaluated respectively according to the same criteria as in Examples 1 to 18.

(Storage Stability)

The respective samples were stored at 50° C. for a month, and then the degree of water separation, oil separation, and creaming was evaluated respectively by visual observation according to the same criteria as in Examples 1 to 18.

TABLE 36

Examples 103 to 106

| | | Example | | | |
|---|---|---|---|---|---|
| | | 103 | 104 | 105 | 106 |
| a | Agar 1 | 0.9 | 0.9 | 0.9 | 0.45 |
| | Xanthan gum*1 | 0.6 | 0.6 | 0.6 | 0.3 |
| | Hydrophobic titanium dioxide*2 | 10.00 | 10.00 | — | — |
| | Hydrophobic zinc oxide*3 | 5.00 | 5.00 | — | — |
| | Sodium metaphosphate | 0.01 | 0.01 | — | — |
| | Deionized water | 57.79 | 57.29 | 47.30 | 83.05 |
| | Glycerin | 5.00 | 5.00 | — | — |
| | 1,3-butylene glycol | — | — | 5.00 | 5.00 |
| | Methylparaben | 0.15 | 0.15 | 0.15 | 0.15 |
| | Propylparaben | 0.05 | 0.05 | 0.05 | 0.05 |
| | Hydrogenated lecithin*4 | 0.50 | 1.00 | 1.00 | 1.00 |

TABLE 36-continued

Examples 103 to 106

| | | Example | | | |
|---|---|---|---|---|---|
| | | 103 | 104 | 105 | 106 |
| b | Erythrityl triethylhexanoate*5 | 10.00 | 10.00 | — | — |
| | Dimethicone*6 | 10.00 | 10.00 | — | — |
| | Hydrogenated polydecene*7 | — | — | 45.00 | 10.00 |
| | Total | 100 | 100 | 100 | 100 |
| | Dirt generation | A | A | A | A |
| | Storage stability | A | A | A | A |

*1"NOMCORT ZZ" (manufactured by The Nisshin OilliO Group, Ltd.)
*2"MTY-02" (manufactured by TAYCA)
*3"MZ-303S" (manufactured by TAYCA)
*4"Basis LP-20H" (manufactured by The Nisshin OilliO Group, Ltd.)
*5"SALACOS E-38" (manufactured by The Nisshin OilliO Group, Ltd.)
*6"KF96-6cs" (manufactured by Shin-Etsu Chemical Co., Ltd.)
*7"NOMCORT HP-30" (manufactured by The Nisshin OilliO Group, Ltd.)

The feeling during use and storage stability were evaluated in the same manner as in Examples 1 to 18.

As a result, all of the compositions for external use on skin of Examples 103 to 106 as the composition for external use on skin of the present invention did not generate the dirt-like scum and were excellent in the feeling during use. Particularly, Examples 103 and 104, which had the almost same composition as the sunscreen of Example 82 except that hydrogenated lecithin was not added to the sunscreen, were more improved in terms of dirt generation compared to the sunscreen. Furthermore, even when these compositions for external use on skin were stored at 50° C. for a month, storage stability was excellent.

Examples 107 to 114

Production Method

According to the compounding shown in Table 37, all components were weighed and put in a beaker, and mixed and heated up to the stirring temperature described in Table 37, followed by stirring with a table disper mixer at 2000 rpm, thereby dissolving all components. Immediately after the dissolution was completed, the obtained solution was stirred under the stirring conditions shown in Table 37 and then slowly cooled. The thus obtained composition for external use on skin was taken as a sample.

In the section of "instrument used" in Table 37, "-" means that the solution was left to stand without using a stirring instrument. In addition, among three kinds of stirring instruments used, the stirring force of a "Homomixer MARK II 2.5 model" ("homo" in Table 37) is strongest, the stirring force of a "Homodisper 2.5 model φ40" ("disper" in Table 37) is the second strongest, and the stirring force of an "Economy fixed U-shaped impeller, blade width 65 mm" ("anchor" in Table 37) is weakest.

(Feeling During Use)

0.5 g of the respective samples were applied to the back of hands of a panel consisting of 15 members after the hands were washed, and the feeling during use was surveyed by answers to a questionnaire. The "feeling of sliminess" was evaluated respectively according to the following criteria.

"Feeling of Sliminess"

A: The sample is not slimy and is very fresh.
B: The sample is almost not slimy and fresh.
C: The sample is slightly slimy.
D: The sample is slimy.

TABLE 37

Examples 107 to 114

(% by mass)

| | | Example | | | | | | | |
|---|---|---|---|---|---|---|---|---|---|
| | | 107 | 108 | 109 | 110 | 111 | 112 | 113 | 114 |
| Compounding | Agar 1 | 1.8 | 1.8 | 1.8 | 1.8 | 1.8 | 1.8 | 1.8 | 0.9 |
| | Xanthan gum*[1] | 1.2 | 1.2 | 1.2 | 1.2 | 1.2 | 1.2 | 1.2 | 0.6 |
| | Methylparaben | 0.15 | 0.15 | 0.15 | 0.15 | 0.15 | 0.15 | 0.15 | 0.15 |
| | Propylparaben | 0.05 | 0.05 | 0.05 | 0.05 | 0.05 | 0.05 | 0.05 | 0.05 |
| | Deionized water | 96.8 | 96.8 | 96.8 | 96.8 | 96.8 | 96.8 | 96.8 | 98.3 |
| | Total | 100 | 100 | 100 | 100 | 100 | 100 | 100 | 100 |
| Stirring conditions | Instrument used | Disper*[2] | Disper*[2] | — | Anchor*[3] | Homo*[4] | Homo*[4] | Homo*[4] | Homo*[4] |
| | Rotation frequency (rpm) | 2,000 | 2,000 | 0 | 100 | 2,000 | 5,000 | 5,000 | 5,000 |
| | Temperature (° C.) | 80 | 85 | 90 | 85 | 85 | 85 | 90 | 85 |
| Stirring time | 10 min | — | — | — | — | — | — | — | B |
| | 30 min | — | — | — | — | — | B | B | B |
| | 50 min | — | — | — | — | — | — | — | A |
| | 60 min | B | A | A | A | A | A | A | A |
| | 90 min | B | A | — | — | A | — | — | A |
| | 120 min | — | A | A | A | — | — | — | A |

*[1]"NOMCORT ZZ" (manufactured by The Nisshin OilliO Group, Ltd.)
*[2]"Homodisper 2.5 model ϕ40" (manufactured by PRIMIX Corporation)
*[3]"Economy fixed U-shaped impeller, blade width 65 mm" (manufactured by IMPELLER)
*[4]"Homomixer MARK II 2.5 model" (manufactured by PRIMIX Corporation)

Evaluation results of the feeling of sliminess of the respective samples are shown for each stirring time in Table 37. In the section of "stirring time" in Table 37, "-" indicates that the evaluation was not performed.

As a result, it was understood that when stirring time was 60 minutes or longer, Example 108 in which the solution was stirred at a temperature equal to or higher than 85° C. was further improved in terms of the feeling of sliminess and superior in the feeling during use since this sample was very fresh, compared to the composition for external use on skin of Example 107 in which the solution was stirred at 80° C.

The compositions for external use on skin of Examples 112 and 113 that were stirred with the same stirring force were compared to each other. As a result, in all of these compositions, the feeling of sliminess was further improved when the stirring time was 60 minutes or longer, compared to a case where the stirring time was 30 minutes or shorter. Furthermore, when Example 109 that was left to stand without being stirred was left to stand for 60 minutes or longer similarly to Example 113 that was stirred with the strongest stirring force, a composition for external use on skin not giving a feeling of sliminess was obtained. These results suggest that whether stirring is performed is not important, but holding the solution at a temperature equal to or higher than 85° C. is important.

When Example 114, in which the amount of the contained water-soluble polymer (agar 1 and xanthan gum) as the component (A) was half of that of Example 112, was stirred for 50 minutes or longer, a composition for external use on skin not imparting a feeling of sliminess was obtained. From this result, it was considered that even if stirring time was set to 50 minutes for Examples 108 to 113, a composition for external use on skin not giving a feeling of sliminess could be obtained.

Examples 115 to 118

Production Method

In the compounding shown in Table 38, first, agar 1 and xanthan gum were dispersed in a polyalcohol (glycerin, 1,3-butylene glycol, or 1,3-propanediol), and then all of the remaining components were added thereto, followed by heating up to 85° C. The mixture was stirred with a table disper mixer at 2000 rpm, thereby dissolving all components. Immediately after the dissolution was completed, the obtained solution (water-soluble polymer solution) was stirred using a Homodisper 2.5 model (manufactured by PRIMIX Corporation, ϕ40) at 3000 rpm and then slowly cooled. The thus obtained composition for external use on skin was taken as a sample.

(Feeling During Use)

0.5 g of the respective samples were applied to the back of hands of a panel consisting of 15 members after the hands were washed, and the feeling during use was surveyed by answers to a questionnaire. The "feeling of sliminess" was evaluated respectively according to the same criteria as in Examples 107 to 114.

TABLE 38

Examples 115 to 118

(% by mass)

| | | Example | | | |
|---|---|---|---|---|---|
| | | 115 | 116 | 117 | 118 |
| Compounding | Agar 1 | 1.8 | 1.8 | 1.8 | 1.8 |
| | Xanthan gum*[1] | 1.2 | 1.2 | 1.2 | 1.2 |
| | Glycerin | — | 7 | — | — |
| | 1,3-butylene glycol | — | — | 7 | — |
| | 1,3-propanediol | — | — | — | 7 |

TABLE 38-continued

Examples 115 to 118

|  |  | Example (% by mass) | | | |
|---|---|---|---|---|---|
|  |  | 115 | 116 | 117 | 118 |
|  | Methylparaben | 0.15 | 0.15 | 0.15 | 0.15 |
|  | Propylparaben | 0.05 | 0.05 | 0.05 | 0.05 |
|  | Deionized water | 96.8 | 89.8 | 89.8 | 89.8 |
|  | Total | 100 | 100 | 100 | 100 |
| Stirring time | 30 min | — | — | — | B |
|  | 60 min | A | A | A | A |
|  | 90 min | A | A | A | — |
|  | 120 min | A | A | A | A |

*[1]"NOMCORT ZZ" (manufactured by The Nisshin OilliO Group, Ltd.)

The evaluation results of the feeling of sliminess of the respective samples are shown for each stirring time in Table 38. In the section of "stirring time" in Table 38, "-" means that evaluation was not performed. As a result, regardless of whether a polyalcohol was added, when the solution was stirred at 85° C. for 60 minutes or longer, a composition for external use on skin that did not impart a feeling of sliminess and that was very fresh was obtained.

Example 119

Cleansing Gel (Production Method)

In the compounding shown in Table 39, first, a component a was weighed and put in a beaker, and heated up to 85° C., and the resultant was stirred with a table disper mixer at 2000 rpm, thereby dissolving all components. Immediately after the dissolution was completed, the solution was stirred at 85° C. and at 5000 rpm for the time shown in Table 39. After stirring, a component b was added to the component a, followed by stirring at 2000 rpm for 10 minutes for dispersing, and then the mixture was cooled to room temperature under stirring. The thus obtained cleansing gel was taken as a sample. For stirring, a "Homomixer MARK II 2.5 model" (manufactured by PRIMIX Corporation) was used.

(Feeling During Use)

0.5 g of the respective samples were applied to the back of hands of a panel consisting of 15 members after the hands were washed, and the feeling during use was surveyed by answers to a questionnaire. The "feeling of sliminess" was evaluated respectively according to the same criteria as in Examples 107 to 114.

TABLE 39

Example 119 (Cleansing Gel)

|  | Component | Compounding (% by mass) |
|---|---|---|
| a | Agar 1 | 1.2 |
|  | Xanthan gum*[1] | 0.8 |
|  | Glycerin | 5.0 |
|  | Phenoxyethanol | 0.5 |
|  | Methylparaben | 0.2 |

TABLE 39-continued

Example 119 (Cleansing Gel)

|  | Component | Compounding (% by mass) |
|---|---|---|
|  | Propylparaben | 0.05 |
|  | Deionized water | 77.25 |
| b | Propanediol di(caprylate/caparate)*[2] | 15.0 |
|  | Total | 100 |
| Stirring time | 10 min | B |
|  | 60 min | A |
|  | 90 min | A |
|  | 120 min | A |

*[1]"NOMCORT ZZ" (manufactured by The Nisshin OilliO Group, Ltd.)
*[2]"SALACOS PR-85" (manufactured by The Nisshin OilliO Group, Ltd.) (relative permittivity 4.0)

The evaluation results of the feeling of sliminess of the respective samples are shown for each stirring time in Table 39. The cleansing gel obtained when the stirring time was 60 minutes or longer did not impart a feeling of sliminess, was very fresh and excellent in the feeling during use. This result clearly shows that even when the composition for external use on skin of the present invention is an emulsion composition containing the oil as the component (E), if a solution in which the water-soluble polymer as the component (A) is dissolved is stirred at a temperature equal to or higher than 85° C. for a certain time or longer in the production process, the feeling of sliminess can be improved more.

Examples 120 to 122

Baby Shampoo (Production Method)

According to the compounding shown in Table 40, all components were weighed and put in a beaker, and mixed and dissolved by being heated at 80° C. to 95° C. Immediately after the dissolution was completed, the obtained solution was stirred using a Homodisper 2.5 model (manufactured by PRIMIX Corporation, φ40) at 3000 rpm at the stirring temperature and for the stirring time described in Table 40. After stirring was completed, the resultant was slowly cooled, and the thus obtained baby shampoo was taken as a sample. When commercially available products were used as surfactants, each of the products was mixed respectively such that the amount of active ingredients (surfactants themselves) mixed become the amount described in Table 40.

(Feeling During Use)

The "foaming", "foam retainability", "dripping", "feeling during use", "easiness of rinse", "irritating properties", and "spreadability on hair" of the respective samples were evaluated respectively according to the same criteria as in Examples 94 to 96.

TABLE 40

Examples 120 to 122 (Baby Shampoo)

|  |  | Example (% by mass) | | |
|---|---|---|---|---|
|  |  | 120 | 121 | 122 |
| Compounding | Agar 1 | 0.45 | 0.45 | 0.45 |
|  | Xanthan gum*[1] | 0.3 | 0.3 | 0.3 |
|  | Cocamidopropyl betaine*[2] | 6 | 6 | 6 |

TABLE 40-continued

Examples 120 to 122 (Baby Shampoo)

|  |  | Example 120 | Example 121 | Example 122 (% by mass) |
|---|---|---|---|---|
|  | Decyl glucoside*3 | 2.24 | 2.24 | 2.24 |
|  | Hydroxyethyl urea*4 | 5 | 5 | 5 |
|  | Glycerin | 5 | 5 | 5 |
|  | Methylparaben | 0.2 | 0.2 | 0.2 |
|  | Propylparaben | 0.05 | 0.05 | 0.05 |
|  | EDTA-2Na | 0.01 | 0.01 | 0.01 |
|  | Deionized water | 80.75 | 80.75 | 80.75 |
|  | Total | 100 | 100 | 100 |
| Stirring conditions | Stirring temperature | 85° C. | 85° C. | 80° C. |
|  | Stirring time | 30 min | 50 min | 30 min |
| Evaluation results | Foaming | A | A | A |
|  | Foam retainability | A | A | A |
|  | Dripping | A | A | A |
|  | Feeling during use | B | A | B |
|  | Spreadability on hair | B | A | B |
|  | Easiness of rinse | A | A | A |
|  | Irritating properties | B | B | B |

*1"NOMCORT ZZ" (manufactured by The Nisshin OilliO Group, Ltd.)
*3"Lebon 2000HG" (manufactured by Sanyo Chemical Industries, Ltd.), active ingredient: 30%
*3"Mydol 10" (manufactured by KAO Corporation), active ingredient: 40%
*4"Hydrovance" (manufactured by AkzoNoBel N.V.)

The samples of Examples 120 to 122 had the same composition and differed from each other only in terms of the stirring conditions of the water-soluble polymer solution. As a result, all of the samples were excellent in foaming and foam retainability, did not drip, did not impart a feeling of stickiness or sliminess, and were spread excellently on hair. Among these, the sample of Example 121 in which the water-soluble polymer solution was stirred at 85° C. for 50 minutes showed further reduction in the feeling of stickiness or sliminess and was excellently pleasing to the sense of touch when used, compared to the sample of Example 120 in which the water-soluble polymer solution was stirred at 85° C. for 30 minutes or the sample of Example 122 in which the solution was stirred at 80° C. for 30 minutes. These results clearly show that if the water-soluble polymer solution is stirred at 85° C. for 50 minutes or longer in the production process, a composition for external use on skin that further reduces the feeling of stickiness or sliminess is obtained.

Production Example 2

Two kinds of low-molecular weight agar having a molecular weight of 20000 and 60000 were produced, and a weight average molecular weight, a number average molecular weight, a gel strength, and a push-out load of these agars were measured in the same manner as in Production Example 1. For the low-molecular weight agar having a molecular weight of 60000, a 1.5% gel strength was measured just like the agars 1 to 4 in Production Example 1. On the other hand, for the low-molecular weight agar having a molecular weight of 20000, a 3.0% gel strength and a push-out load were measured since a 1.5% gel strength could not be measured due to the excessive softness of the gel. The measurement results are shown in Table 41.

TABLE 41

List of Values of Physical Properties of Agar

|  | Weight average molecular weight (Mw) | Number average molecular weight (Mn) | Mw/Mn | 1.5% gel strength | 3.0% gel strength | 1.5% gel push-out load |
|---|---|---|---|---|---|---|
| Agar 5 | 60000 | 11300 | 5.3 | 25 g/cm$^2$ | — | 1390 g |
| Agar 6 | 20000 | 3900 | 5.1 | — | 8 g/cm$^2$ | 150 g |

Examples 123 and 124

Production Method

In the compounding shown in Table 42, first, a component a was weighed and put in a beaker, and heated up to 85° C., and the resultant was stirred with a table disper mixer at 2000 rpm, thereby dissolving all components. Immediately after the dissolution was completed, the resultant was stirred at 85° C. for an hour. After stirring, a component b was added to the component a, and the mixture was dispersed by being stirred at 2000 rpm for 10 minutes, followed by cooling to room temperature under stirring. The resultant was deaerated under reduced pressure, and the thus obtained composition for external use on skin was taken as a sample.

(Feeling During Use)

The respective compositions for external use on skin were applied to the whole face of a panel consisting of 15 members after the face was washed, and the feeling during use was surveyed by answers to a questionnaire. The "feeling of stickiness", "spreadability on skin", "dirt generation", "feeling of sliminess", and "re-lubricating properties of fingers" were evaluated respectively according to the same criteria as in Examples 1 to 18. The evaluation results are shown in Table 42.

(Storage Stability)

The respective samples were stored at 50° C. for a month, and then the degree of water separation, oil separation, and creaming was evaluated respectively by visual observation according to the same criteria as in Examples 1 to 18. The evaluation results are shown in Table 42.

TABLE 42

Examples 123 and 124

|  |  | Example 123 | Example 124 (% by mass) |
|---|---|---|---|
| a | Agar 5 | 0.9 | — |
|  | Agar 6 | — | 0.9 |
|  | Xanthan gum*1 | 0.6 | 0.6 |
|  | Propylene glycol | 10 | 1.0 |
|  | Sodium hyaluronate | 0.1 | 0.1 |
|  | Sodium pyrrolidone carboxylate | 2 | 2 |
|  | Glycerin | 4 | 4 |
|  | Diglycerin | 4 | 4 |
|  | Decaglycerin | 2 | 2 |
|  | Methylparaben | 0.2 | 0.2 |
|  | Purified water | 66.2 | 66.2 |
| b | Neopentyl glycol dicaprate | 10.00 | 10.00 |
|  | Total | 100 | 100 |
|  | Feeling of stickiness | A | A |
|  | Spreadability on skin | A | A |

TABLE 42-continued

Examples 123 and 124

| | Example | (% by mass) |
|---|---|---|
| | 123 | 124 |
| Dirt generation | A | A |
| Feeling of sliminess | A | A |
| Re-lubricating property of fingers | A | A |
| Storage stability | A | B |

*[1]"NOMCORT ZZ" (manufactured by The Nisshin OilliO Group, Ltd.)
*[2]"ESTEMOL N-01" (manufactured by The Nisshin OilliO Group, Ltd.) (relative permittivity 3.4)

The compositions for external use on skin of Examples 123 and 124 are compositionally the same as the composition for external use on skin of Example 7, except that the molecular weight of the mixed low-molecular weight agar is different. Examples 123 and 124 were also excellent just like Example 7 since all of these compositions did not impart a feeling of stickiness or sliminess, were spread excellently on the skin, did not generate the dirt-like scum, and did not make fingers slippery even when the fingers came into contact with moisture again. Moreover, even when these compositions for external use on skin were stored at 50° C. for a month, a liquid residue was not produced, and emulsion stability of oil was excellent, that is, storage stability was excellent.

Examples 125 to 130

Sunscreen (Production Method)

First, according to the compounding shown in Table 43, all components were weighed and put in a beaker, and heated up to 85° C., and the resultant was stirred with a table disper mixer at 5000 rpm, thereby dissolving all component excluding pigments. Immediately after the dissolution was completed, the resultant was stirred at 85° C. for an hour. After stirring, the resultant was slowly cooled while being stirred at 2000 rpm. The resultant was deaerated under reduced pressure, thereby obtaining pigment dispersion compositions C and D.

Thereafter, in Examples 126, 127, 129, and 130, according to the compounding shown in Table 44, all components were weighed and put in a beaker, and heated up to 85° C., and the resultant was stirred with a table disper mixer at 2000 rpm, thereby dissolving all components excluding pigments. Immediately after dissolution was completed, the resultant was stirred at 85° C. for an hour. After stirring, the resultant was slowly cooled while being stirred at 2000 rpm and then deaerated under reduced pressure, and the thus obtained sunscreen was taken as a sample.

On the other hand, in Examples 125 and 128, according to the compounding shown in Table 44, all components were weighed and put in a beaker, and heated up to 85° C., and the resultant was stirred with a table disper mixer at 2000 rpm so as to disperse pigments. Thereafter, the resultant was slowly cooled while being stirred at 2000 rpm and then deaerated under reduced pressure, and the thus obtained sunscreen was taken as a sample.

(Evaluation of Pigment Dispersibility)

The respective samples were stored at 50° C. for a month, and then aggregation and sedimentation of pigments were evaluated respectively according to the same criteria as in Examples 59 to 71.

(Feeling During Use)

0.5 g of the respective samples were applied to the back of hands of a panel consisting of 15 members after the hands were washed, and the feeling during use was surveyed by answers to a questionnaire. The "feeling of stickiness", "spreadability on skin", "dirt generation", "feeling of sliminess", and "re-lubricating property of fingers" were evaluated respectively according to the same criteria as in Examples 1 to 18. The evaluation results are shown in Table 44.

(Water Resistance)

0.5 g of the respective samples were applied to the back of hands of a panel consisting of 15 members and dried, after the hands were washed. Thereafter, feeling of the pigment dispersion composition remaining on the skin, which was experienced when several drops of water were dripped onto the hand, was evaluated according to the same criteria as in Examples 66 to 78. The evaluation results are shown in Table 44.

TABLE 43

| | Pigment dispersion composition C | (% by mass) Pigment dispersion composition D |
|---|---|---|
| Agar 5 | 1.8 | — |
| Agar 6 | — | 1.8 |
| Xanthan gum*[1] | 1.2 | 1.2 |
| Hydrophobic titanium dioxide 2*[2] | 20 | 20 |
| Hydrophobic zinc oxide*[3] | 10 | 10 |
| Deionized water | 67 | 67 |
| Total | 100 | 100 |

*[1]"NOMCORT ZZ" (manufactured by The Nisshin OilliO Group, Ltd.)
*[2]"MT-100TV" (manufactured by TAYCA)
*[3]"MZ-303S" (manufactured by TAYCA)

TABLE 44

Examples 125 to 130 (Sunscreen)

| | Example | | | | | (% by mass) |
|---|---|---|---|---|---|---|
| | 125 | 126 | 127 | 128 | 129 | 130 |
| Pigment dispersion composition C | 50 | — | — | — | — | — |
| Pigment dispersion composition D | — | — | — | 50 | — | — |
| Agar 5 | — | 0.6 | 0.9 | — | — | — |
| Agar 6 | — | — | — | — | 0.6 | 0.9 |
| Xanthan gum*[1] | — | 0.4 | 0.6 | — | 0.4 | 0.6 |
| Hydrophilic titanium dioxide 1*[2] | — | 10 | — | — | 10 | — |
| Hydrophobic titanium dioxide 2*[3] | — | — | 10 | — | — | 10 |
| Hydrophilic zinc oxide*[4] | — | 5 | — | — | 5 | — |
| Hydrophobic zinc oxide*[5] | — | — | 5 | — | — | 5 |
| Sodium metaphosphate | 0.01 | 0.01 | 0.01 | 0.01 | 0.01 | 0.01 |
| Deionized water | 21.79 | 68.79 | 55.29 | 21.79 | 68.79 | 55.29 |
| Glycerin | 3 | 3 | 3 | 3 | 3 | 3 |
| 1,3-butylene glycol | 5 | 10 | 5 | 5 | 10 | 5 |
| Methylparaben | 0.15 | 0.15 | 0.15 | 0.15 | 0.15 | 0.15 |

TABLE 44-continued

Examples 125 to 130 (Sunscreen)

|  | Example (% by mass) | | | | | |
|---|---|---|---|---|---|---|
|  | 125 | 126 | 127 | 128 | 129 | 130 |
| Propylparaben | 0.05 | 0.05 | 0.05 | 0.05 | 0.05 | 0.05 |
| Erythrityl triethyl-hexanoate*6 | 10 | 2 | 10 | 10 | 2 | 10 |
| Dimethicone*7 | 10 | — | 10 | 10 | — | 10 |
| Total | 100 | 100 | 100 | 100 | 100 | 100 |
| Aggregation of pigment | B | B | B | B | B | B |
| Sedimentation of pigment | B | B | B | B | B | B |
| Feeling of stickiness | A | A | A | A | A | A |
| Spreadability on skin | A | B | B | B | B | B |
| Dirt generation | A | B | B | A | B | B |
| Feeling of sliminess | A | A | A | A | A | A |
| Re-lubricating property of fingers | A | A | A | A | A | A |
| Water resistance | A | B | A | A | B | A |

*1"NOMCORT ZZ" (manufactured by The Nisshin OilliO Group, Ltd.)
*2"MT-100WP" (manufactured by TAYCA)
*3"MT-100TV" (manufactured by TAYCA)
*4"Maxlight ZS-64" (manufactured by SHOWA DENKO K.K.)
*5"MZ-303S" (manufactured by TAYCA)
*6"SALACOS E-38" (manufactured by The Nisshin OilliO Group, Ltd.)
*7"KF96-6cs" (manufactured by Shin-Etsu Chemical Co., Ltd.)

The sunscreens of Examples 125 and 128 have the same composition as the sunscreen of Example 80, except that the molecular weight of the low-molecular weight agar mixed is different. Likewise, except for the molecular weight of the low-molecular weight agar, the sunscreens of Examples 126 and 129 have the same composition as the sunscreen of Example 81, and the sunscreens of Examples 127 and 130 have the same composition as the sunscreen of Example 83, respectively. Similarly to the sunscreens of Examples 80 and the like, all of the sunscreens of Examples 125 to 130 were excellent since they did not impart a feeling of stickiness or sliminess, were spread excellent on the skin, did not generate the dirt-like scum, and did not make fingers slippery even when the fingers came into contact with moisture again. Moreover, even when these compositions for external use on skin were stored at 50° C. for a month, a liquid residue was not generated, and emulsion stability of oil was excellent, that is, storage stability was excellent. All of the compositions were excellent since they did not impart a feeling of stickiness or sliminess, were spread excellently on the skin, did not generate the dirt-like scum, and did not make fingers slippery even when the fingers came into contact with moisture again. In addition, even when these compositions for external use on skin were stored at 50° C. for an hour, aggregation and sedimentation of pigments were not observed, and pigment dispersibility was excellent, that is, storage stability was excellent.

Examples 131 to 136 and Comparative Examples 59 to 61

Oil-in-Water Type Emulsion Composition (Production Method)

According to the compounding shown in Table 45, all components were weighed and put in a beaker, and heated up to 85° C., and the resultant was stirred with a table disper mixer at 1000 rpm, thereby dissolving all components. Immediately after the dissolution was completed, the resultant was stirred at 85° C. for an hour. Thereafter, the resultant was slowly cooled while being stirred with a table disper mixer at 1000 rpm and deaerated under reduced pressure, and the thus obtained oil-in-water type emulsion composition was taken as a sample.

(Feeling During Use)

The respective compositions for external use on skin were applied to the back of hands of a panel consisting of 15 members after the hands were washed, and the feeling during use and storage stability were evaluated in the same manner as in Examples 1 to 18. The evaluation results are shown in Table 45.

TABLE 45

Examples 131 to 136 and Comparative Examples 59 to 61

|  | Example | | | | | | Comparative Example (% by mass) | | |
|---|---|---|---|---|---|---|---|---|---|
|  | 131 | 132 | 133 | 134 | 135 | 136 | 59 | 60 | 61 |
| Agar 5 | 0.9 | 0.9 | 0.9 | — | — | — | — | — | — |
| Agar 6 | — | — | — | 0.9 | 0.9 | 0.9 | — | — | — |
| Agar 2 | — | — | — | — | — | — | 0.9 | 0.9 | 0.9 |
| Xanthan gum*1 | 0.6 | 0.6 | 0.6 | 0.6 | 0.6 | 0.6 | 0.6 | 0.6 | 0.6 |
| Hydrogenated polydecene*2 | 10 | — | — | 10 | — | — | 10 | — | — |
| Dipentaerythrityl tri-polyhydroxystearate*3 | — | 10 | — | — | 10 | — | — | 10 | — |
| Dimethylpolysiloxane (6cs)*4 | — | — | 10 | — | — | 10 | — | — | 10 |
| Methylparaben | 0.1 | 0.1 | 0.1 | 0.1 | 0.1 | 0.1 | 0.1 | 0.1 | 0.1 |
| 1,3-butylene glycol | 5 | 5 | 5 | 5 | 5 | 5 | 5 | 5 | 5 |
| Purified water | 83.4 | 83.4 | 83.4 | 83.4 | 83.4 | 83.4 | 83.4 | 83.4 | 83.4 |
| Total | 100 | 100 | 100 | 100 | 100 | 100 | 100 | 100 | 100 |
| Feeling of stickiness | A | A | A | A | A | A | C | D | C |
| Spreadability on skin | A | A | A | A | A | A | B | C | B |
| Dirt generation | A | A | A | A | A | A | D | D | D |

TABLE 45-continued

Examples 131 to 136 and Comparative Examples 59 to 61

|  | Example | | | | | | Comparative Example (% by mass) | | |
|---|---|---|---|---|---|---|---|---|---|
|  | 131 | 132 | 133 | 134 | 135 | 136 | 59 | 60 | 61 |
| Feeling of sliminess | A | A | A | A | A | A | C | C | C |
| Re-lubricating property of fingers | A | A | A | A | A | A | C | C | C |
| Storage stability | A | A | A | B | B | B | A | A | A |

*[1]"NOMCORT ZZ" (manufactured by The Nisshin OilliO Group, Ltd.)
*[2]"NOMCORT HP-30" (manufactured by The Nisshin OilliO Group, Ltd.)
*[3]"SALACOS WO-6" (manufactured by The Nisshin OilliO Group, Ltd.) (relative permittivity 4.1)
*[4]"KF69-6cs" (manufactured by Shin-Etsu Chemical Co., Ltd.)

The oil-in-water type emulsion compositions of Examples 131 to 161 and Comparative Examples 59 to 61 are compositionally the same as the oil-in-water type emulsion compositions of Examples 24, 39, and 46, except that the molecular weight of the low-molecular weight agar mixed is different. As a result, all of the oil-in-water type emulsion compositions of Examples 131 to 136 according to the present invention were excellent since they did not impart a feeling of stickiness or sliminess, were spread excellently on the skin, did not generate the dirt-like scum, and did not make fingers slippery even when the fingers came into contact with moisture again. Moreover, even when these oil-in-water type emulsion compositions were stored at 50° C. for a month, a liquid residue was not produced, and emulsion stability of oil was excellent, that is, storage stability was excellent.

On the other hand, all of the oil-in-water type emulsion compositions of Comparative Examples 59 to 61 using the agar 2 in which the molecular weight of low-molecular weight agar was larger than 60000 generated the dirt-like scum, imparted a feeling of stickiness or sliminess, and made fingers slippery when the fingers came into contact with moisture again, thus feeling during use was poor.

Examples 137 and 138 and Comparative Example 62

Oil-in-Water Type Emulsion Composition (Production Method)

In the compounding shown in Table 46, a component b was dissolved by being stirred at 90° C. In addition, a component a was dissolved at 90° C., and immediately after the dissolution was completed, the resultant was stirred at 85° C. for an hour. Thereafter, the component b was added to the component a, and the mixture was dispersed by being stirred with a table disper mixer at 1000 rpm for 10 minutes, followed by cooling to room temperature under stirring. The thus obtained oil-in-water type emulsion composition was taken as a sample.

(Feeling During Use)

The respective oil-in-water type emulsion compositions were applied to the back of hands of a panel consisting of 15 members after the hands were washed, and the feeling during use and storage stability were evaluated in the same manner as in Examples 1 to 18. The evaluation results are shown in Table 46.

TABLE 46

Examples 137 and 138 and Comparative Example 62

|  | Example | | Comparative Example (% by mass) |
|---|---|---|---|
|  | 137 | 138 | 62 |
| a  Agar 5 | 0.9 | — | — |
| Agar 6 | — | 0.9 | — |
| Agar 2 | — | — | 0.9 |
| Xanthan gum*[1] | 0.6 | 0.6 | 0.6 |
| 1,3-butylene glycol | 5.0 | 5.0 | 5.0 |
| Deionized water | 78.5 | 78.5 | 78.5 |
| b  Dipentaerythrityl tri-polyhydroxystearate*[2] | 10.00 | 10.00 | 10.00 |
| Dimethylpolysiloxane (6cs)*[3] | 5.0 | 5.0 | 5.0 |
| Total | 100 | 100 | 100 |
| Feeling of stickiness | A | A | C |
| Spreadability on skin | A | A | C |
| Dirt generation | A | A | D |
| Feeling of sliminess | A | A | C |
| Re-lubricating property of fingers | A | A | D |
| Storage stability | A | B | A |

*[1]"NOMCORT ZZ" (manufactured by The Nisshin OilliO Group, Ltd.)
*[2]"SALACOS WO-6" (manufactured by The Nisshin OilliO Group, Ltd.) (relative permittivity 4.1)
*[3]"KF96-6cs" (manufactured by Shin-Etsu Chemical Co., Ltd.)

The oil-in-water type emulsion compositions of Examples 137 and 138 and Comparative Example 62 are compositionally the same as the oil-in-water type emulsion composition of Example 53, except that the molecular weight of the low-molecular weight agar mixed is different. As a result, similarly to the oil-in-water type emulsion composition of Example 53, all of the oil-in-water type emulsion compositions of Examples 137 and 138 were excellent since they did not impart a feeling of stickiness or sliminess, were spread excellent on the skin, did not generate the dirt-like scum, and did not make fingers slippery even when the fingers came into contact with moisture again. Moreover, even when these oil-in-water type emulsion compositions were stored at 50° C. for a month, a liquid residue was not produced, and emulsion stability of oil was excellent.

On the other hand, the oil-in-water type emulsion composition of Comparative Example 62 using the agar 2 in which the molecular weight of the low-molecular weight agar was larger than 60000 generated dirt, and made fingers slippery when the fingers came into contact with moisture again, thus feeling during use was poor.

Examples 139 and 140 and Comparative Example 63

Composition for External Use on Skin (Production Method)

According to the compounding shown in Table 47, a component a was weighed and put in a beaker, and heated up to 85° C., and the resultant was stirred with a table disper mixer at 1000 rpm, thereby dissolving all components. Immediately after the dissolution was completed, the resultant was stirred at 85° C. for an hour. Thereafter, the resultant was slowly cooled while being stirred with a table disper mixer at 1000 rpm. After the resultant was cooled to 40° C., a component b dissolved in a different container was added thereto and dispersed evenly. After cooled to room temperature, the mixture was deaerated under reduced pressure, and the thus obtained composition for external use on skin was taken as a sample.

TABLE 47

Examples 139 and 140 and Comparative Example 63

|   | | (% by mass) | | |
|---|---|---|---|---|
|   |   | Example | | Comparative Example |
|   | Component | 139 | 140 | 63 |
| a | Agar 5 | 0.9 | — | — |
|   | Agar 6 | — | 0.9 | — |
|   | Agar 2 | — | — | 0.9 |
|   | Xanthan gum*[1] | 0.6 | 0.6 | 0.6 |
|   | 1,3-propanediol | 10 | 10 | 10 |
|   | Glycerin | 10 | 10 | 10 |
|   | Methylparaben | 0.2 | 0.2 | 0.2 |
|   | Dimethylpolysiloxane (100cs)*[2] | 5 | 5 | 5 |
|   | Squalane | 5 | 5 | 5 |
|   | Water | 44.3 | 44.8 | 45.3 |
| b | L-ascorbic acid-2-phosphate magnesium ester | 3 | 3 | 3 |
|   | Sodium citrate | 1 | 1 | 1 |
|   | Water | 20 | 20 | 20 |
| Total | | 100 | 100 | 100 |
| Feeling of stickiness | | A | A | D |
| Spreadability on skin | | A | A | C |
| Dirt generation | | A | A | D |
| Feeling of sliminess | | A | A | C |
| Re-lubricating property of fingers | | A | A | D |
| Storage stability | | A | B | A |

*[1] "NOMCORT ZZ" (manufactured by The Nisshin OilliO Group, Ltd.)
*[2] "KF-96 100cs" (manufactured by Shin-Etsu Chemical Co., Ltd.)

The compositions for external use on skin of Examples 139 and 140 and Comparative Example 63 are compositionally the same as the composition for external use on skin of Example 19, except that the molecular weight of the low-molecular weight agar mixed is different. The feeling during use and storage stability of the respective samples were evaluated in the same manner as in Examples 1 to 18 and Comparative Examples 1 to 8. As a result, as shown in Table 47, Examples 139 and 140 yielded very excellent results for all evaluation items.

On the other hand, the composition for external use on skin of Comparative Example 63 using the agar 2 in which the molecular weight of the low-molecular weight agar was larger than 60000 was excellent in storage stability, but this composition was very poor in terms of the feeling during use.

Examples 141 and 142 and Comparative Example 64

Cleansing Gel (Production Method)

In the compounding shown in Table 48, first, a component a was weighed and put in a beaker, and heated up to 85° C., and the resultant was stirred with a table disper mixer at 2000 rpm, thereby dissolving all components. Immediately after the dissolution was completed, the resultant was stirred at 5000 rpm at 85° C. for the time shown in Table 48. After stirring, a component b was added to the component a and dispersed by being stirred at 2000 rpm for 10 minutes, followed by cooling to room temperature under stirring. The thus obtained cleansing gel was taken as a sample. In addition, for stirring, "Homomixer MARK II 2.5 model" (manufactured by PRIMIX Corporation) was used.

(Feeling During Use)

0.5 g of the respective samples were applied to the back of hands of a panel consisting of 15 members after the hands were washed, and the feeling during use was surveyed by answers to a questionnaire. The "feeling of sliminess" was evaluated respectively according to the same criteria as in Examples 107 to 114. The evaluation results of the feeling of sliminess of the respective samples are shown for each stirring time in Table 48.

TABLE 48

Examples 141 and 142 and Comparative Example 64 (Cleansing Gel)

|   |   |   | Compounding (% by mass) | | |
|---|---|---|---|---|---|
|   |   |   | Example | | Comparative Example |
|   |   | Component | 141 | 142 | 64 |
| a |   | Agar 5 | 1.2 | — | — |
|   |   | Agar 6 | — | 1.2 | — |
|   |   | Agar 2 | — | — | 1.2 |
|   |   | Xanthan gum*[1] | 0.8 | 0.8 | 0.8 |
|   |   | Glycerin | 5.0 | 5.0 | 5.0 |
|   |   | Phenoxyethanol | 0.5 | 0.5 | 0.5 |
|   |   | Methylparaben | 0.2 | 0.2 | 0.2 |
|   |   | Propylparaben | 0.05 | 0.05 | 0.05 |
|   |   | Deionized water | 77.25 | 77.25 | 77.25 |
| b |   | Propanediol di(caprylate/caprate)*[2] | 15.0 | 15.0 | 15.0 |
|   |   | Total | 100.0 | 100.0 | 100.0 |
| Stirring time | 10 min |   | B | B | D |
|   | 60 min |   | A | A | C |
|   | 90 min |   | A | A | B |
|   | 120 min |   | A | A | A |

*[1] "NOMCORT ZZ" (manufactured by The Nisshin OilliO Group, Ltd.)
*[2] "SALACOS PR-85" (manufactured by The Nisshin OilliO Group, Ltd.) (relative permittivity 4.0)

The cleansing gels of Examples 141 and 142 and Comparative Example 64 are compositionally the same as the cleansing gel of Example 119, except that the molecular weight of the low-molecular weight agar mixed is different. The cleansing gels of Examples 141 and 142 were stirred for 60 minutes or longer, and for this reason, these gels did not impart a feeling of sliminess and were very fresh and excellent in the feeling during use. On the other hand, the cleansing gel of Comparative Example 64 using the agar 2 in which the molecular weight of the low-molecular weight agar was larger than 60000 failed to suppress the feeling of sliminess unless the cleansing gel was stirred for 120 minutes.

Example 143

Baby Shampoo (Production Method)

According to the compounding shown in Table 49, all components were weighed and put in a beaker, and heated up to 85° C., and the resultant was stirred with a table disper mixer at 1000 rpm, thereby dissolving all components. Immediately after the dissolution was completed, the resultant was stirred at 85° C. for an hour. Thereafter, the resultant was slowly cooled while being stirred with a table disper mixer at 1000 rpm, followed by deaeration under reduced pressure, and the thus obtained baby shampoo was taken as a sample.

(Feeling During Use)

The "foaming", "foam retainability", "dripping", "feeling during use", "easiness of rinse", "irritating properties", and "spreadability on hair" of the respective sample were evaluated according to the same criteria as in Examples 94 to 96. The evaluation results are shown in Table 49.

(Storage Stability)

The respective sample was stored at 50° C. for a month, and then the degree of water separation, oil separation, and creaming was evaluated respectively by visual observation according to the same criteria as in Examples 1 to 18. The evaluation results are shown in Table 49.

TABLE 49

Example 143 (Baby Shampoo)

| | (% by mass) Example 143 |
|---|---|
| Agar 5 | 0.45 |
| Xanthan gum*1 | 0.3 |
| Carbomer*2 | — |
| Sodium hydroxide | — |
| Cocamidopropyl betaine*3 | 6 |
| Decyl glucoside*4 | 2.24 |
| Polyquaternium-10*5 | 0.5 |
| Hydroxyethyl urea*6 | — |
| Glycerin | 5 |
| Methylparaben | 0.2 |
| Propylparaben | 0.05 |
| EDTA-2Na | 0.01 |
| Deionized water | 85.25 |
| Total | 100 |
| Foaming | A |
| Foam retainability | A |
| Dripping | A |
| Feeling during use | A |
| Spreadability on hair | A |
| Easiness of rinse | A |
| Irritating properties | B |
| Storage stability | B |

*1"NOMCORT ZZ" (manufactured by The Nisshin OilliO Group, Ltd.)
*2"Carbopol 940" (manufactured by Lubrizol Advanced Materials)
*3"Lebon 2000HG" (manufactured by Sanyo Chemical Industries, Ltd.), active ingredient: 30%
*4"Mydol 10" (manufactured by KAO Corporation), active ingredient: 40%
*5"UCARE Polymer JR-400" (manufactured by Dow Chemical Company Japan)
*6"Hydrovance" (manufactured by AkzoNoBel N.V.)

The baby shampoo Example 143 is compositionally the same as the baby shampoo of Example 98, except that the molecular weight of the low-molecular weight agar mixed is different. As a result, the baby shampoos of Example 143 as the composition for external use on skin of the present invention were excellent in foaming and foam retainability, did not drip, did not impart a feeling of stickiness or sliminess, and were spread excellently on hair. In addition, even when the sample was stored at 50° C. for a month, sedimentation of solids was not observed, so storage stability was excellent.

Example 144

Production Method

According to the compounding shown in Table 50, all components were weighed and put in a beaker, and heated up to 85° C., and the resultant was stirred with a table disper mixer at 2000 rpm, thereby dissolving all components. Immediately after the dissolution was completed, the resultant was stirred at 85° C. for an hour. Thereafter, the resultant was slowly cooled while being stirred with a table disper mixer at 2000 rpm, followed by deaeration under reduced pressure, and the thus obtained composition for external use on skin was taken as a sample.

(Feeling During Use)

0.5 g of the respective sample was applied to the back of hands of a panel consisting of 15 members after the hands were washed, and the feeling during use was surveyed by answers to a questionnaire. The "dirt generation" was evaluated respectively according to the same criteria as in Examples 1 to 18. The evaluation results are shown in Table 50.

(Storage Stability)

The respective sample was stored at 50° C. for a month, and then the degree of water separation, oil separation, and creaming was evaluated respectively by visual observation according to the same criteria as in Examples 1 to 18. The evaluation results are shown in Table 50.

TABLE 50

Example 144 (% by mass)

| | | Example 144 | Example 104 |
|---|---|---|---|
| a | Agar 1 | 0.9 | 0.9 |
| | Xanthan gum*1 | 0.6 | 0.6 |
| | Hydrophobic titanium dioxide*2 | 10 | 10 |
| | Hydrophobic zinc oxide*3 | 5 | 5 |
| | Sodium metaphosphate | 0.01 | 0.01 |
| | Deionized water | 57.79 | 57.29 |
| | Glycerin | 5 | 5 |
| | Methylparaben | 0.15 | 0.15 |
| | Propylparaben | 0.05 | 0.05 |
| | Hydrogenated lecithin*4 | — | 1 |
| b | Erythrityl triethylhexanoate*5 | 10.00 | 10.00 |
| | Dimethicone*6 | 10.00 | 10.00 |
| | Hydrogenated polydecene*7 | — | — |
| | Total | 100 | 100 |
| | Dirt generation | B | A |
| | Storage stability | A | A |

*1"NOMCORT ZZ" (manufactured by The Nisshin OilliO Group, Ltd.)
*2"MTY-02" (manufactured by TAYCA)
*3"MZ-303S" (manufactured by TAYCA)
*4"Basis LP-20H" (manufactured by The Nisshin OilliO Group, Ltd.)
*5"SALACOS E-38" (manufactured by The Nisshin OilliO Group, Ltd.)
*6"KF96-6cs" (manufactured by Shin-Etsu Chemical Co., Ltd.)
*7"NOMCORT HP-30" (manufactured by The Nisshin OilliO Group, Ltd.)

The composition for external use on skin of Example 144 is compositionally the same as the composition for external use on skin of Example 104, except that the composition for external use on skin of Example 144 is not mixed with hydrogenated lecithin. The results of Example 104 are also described in Table 50. As a result, similarly to the composition for external use on skin of Example 104, the composition for external use on skin of Example 144 was excellent in both the feeling during use and storage stability. However, the composition for external use on skin of Example 104 was superior to the composition for external use on skin of Example 144, in terms of the generation of the dirt-like scum.

Examples 145 to 147

Production Method

In the compounding shown in Table 51, first, a component a was weighed and put in a beaker, and heated up to 85° C., and the resultant was stirred with a table disper mixer at 3000 rpm, thereby dissolving all components. Immediately after the dissolution was completed, the resultant was stirred at 85° C. at 3000 rpm for an hour. After stirring, a component b was added to the component a and evenly mixed by being stirred at 3000 rpm, and then a component c was further added thereto and evenly mixed by being stirred at 3000 rpm. The mixture was cooled to room temperature under stirring, followed by deaeration under reduced pressure, and the thus obtained composition for external use on skin was taken as a sample.

(Feeling During Use)

0.5 g of the respective samples were applied to the back of hands of a panel consisting of 15 members after the hands were washed, and the feeling during use during application was surveyed by answers to a questionnaire. The "dirt generation" was evaluated according to the following criteria. The evaluation results are shown in Table 51.

[Dirt Generation]

A$^+$: 14 or more people answered that dirt-like scum was not generated and the feeling during use was excellent.

A: 12 to 13 people answered that dirt-like scum was not generated and the feeling during use was excellent.

B: 8 to 11 people answered that dirt-like scum was not generated and the feeling during use was excellent.

C: 4 to 7 people answered that dirt-like scum was not generated and the feeling during use was excellent.

D: 3 or less people answered that dirt-like scum was not generated and the feeling during use was excellent.

(Storage Stability)

The respective samples were stored at 50° C. for a month, and then the degree of water separation, oil separation, and creaming was evaluated respectively by visual observation according to the same criteria as in Examples 1 to 18. The evaluation results are shown in Table 51.

TABLE 51

Examples 145 to 147

| | | (% by mass) Example | | |
|---|---|---|---|---|
| | | 145 | 146 | 147 |
| a | Agar 1 | 0.9 | 0.9 | 0.9 |
| | Xanthan gum*[1] | 0.6 | 0.6 | 0.6 |
| | Purified water | 82.4 | 82.4 | 83.4 |
| b | Methylparaben | 0.1 | 0.1 | 0.1 |
| | 1,3-butylene glycol | 5 | 5 | 5 |
| | Hydrogenated lecithin*[2] | 1 | — | — |
| | Sucrose fatty acid ester*[3] | — | 1 | — |
| c | Hydrogenated polydecene | 10 | 10 | 10 |
| | Total | 100 | 100 | 100 |
| | Dirt generation | A$^+$ | A$^+$ | A |
| | Storage stability | A | A | A |

*[1]"NOMCORT ZZ" (manufactured by The Nisshin OilliO Group, Ltd.)
*[2]"Basis LP-20H" (manufactured by The Nisshin OilliO Group, Ltd.)
*[3]"DK Ester F-160" (manufactured by DAI-ICHI KOGYO SEIYAKU CO., LTD.)
*[4]"NOMCORT HP-30" (manufactured by The Nisshin OilliO Group, Ltd.)

The composition for external use on skin of Example 147 is compositionally the same as the composition for external use on skin of Example 24. In addition, the compositions for external use on skin of Examples 145 and 146 are compositionally the same as the composition for external use on skin of Example 147, except that hydrogenated lecithin and sucrose fatty acid ester are respectively mixed with the compositions for external use on skin of Examples 145 and 146. As a result, similarly to the composition for external use on skin of Example 147, the compositions for external use on skin of Examples 145 and 146 were excellent in both the feeling during use and storage stability. Particularly, the compositions for external use on skin of Examples 145 and 146 were superior to the composition for external use on skin of Example 147, in terms of generation of the dirt-like scum.

Examples 148 and 149

Oil-in-Water Type Emulsion Composition (Production Method)

In the compounding shown in Table 52, first, a component a was weighed and put in a beaker, and heated up to 85° C., and the resultant was stirred with a table disper mixer at 3000 rpm, thereby dissolving all components. Immediately after the dissolution was completed, the resultant was stirred at 85° C. at 3000 rpm for an hour. After stirring, a component b was added to the component a and evenly mixed by being stirred at 3000 rpm. The mixture was cooled to room temperature while being stirred at 2000 rpm, followed by deaeration under reduced pressure, and the thus obtained oil-in-water type emulsion composition was taken as a sample. In table 52, dipentaerythrityl tri-polyhydroxystearate is high-polarity oil, and mineral oil is non-polar oil.

TABLE 52

Examples 148 and 149

| | | (% by mass) Example | |
|---|---|---|---|
| | | 148 | 149 |
| a | Agar 1 | 0.9 | 0.9 |
| | Xanthan gum*[1] | 0.6 | 0.6 |
| | Methylparaben | 0.2 | 0.2 |
| | Propylparaben | 0.05 | 0.05 |
| | Deionized water | 88.25 | 88.25 |
| b | Dipentaerythrityl tri-polyhydroxystearate*[2] | 10 | — |
| | Mineral oil | — | 10 |
| | Total | 100 | 100 |

*[1]"NOMCORT ZZ" (manufactured by The Nisshin OilliO Group, Ltd.)
*[2]"SALACOS WO-6" (manufactured by The Nisshin OilliO Group, Ltd.) (relative permittivity 4.1)

The feeling during use and storage stability of the respective samples were evaluated in the same manner as in Examples 1 to 18 and Comparative Examples 1 to 8. As a result, the compositions for external use on skin of Examples 148 and 149 were excellent in the feeling during use and storage stability.

[Moisturizing Properties]

Moisturizing properties of the skin to which the respective samples were applied were evaluated using change in hydration level of stratum corneum after application as an index. Specifically, first, both arms of a panel consisting of 8 members were washed with a soap, and then the panel was acclimatized in a constant temperature chamber at 22° C. with a humidity of 45% for an hour. Subsequently, a 3 cm×3 cm sample application portion was set in three sites of the inner portion of the arms of the panel, and the hydration level of stratum corneum of those areas before sample application was measured respectively. After the measurement, among the three sample application sites, the composition for external use on skin of Example 148 was evenly applied to one site, and the composition for external use on skin of Example 149 was evenly applied to another site, in an amount of 40 μg respectively. Nothing was applied to the remaining one site. After sample application, the hydration level of stratum corneum of the respective sample-applied portions was measured every 15 minutes to a point in time when 60 minutes elapsed. Based on the value obtained by dividing the hydration level of stratum corneum at each time by hydration level of stratum corneum before application, increase and decrease in the hydration level of stratum corneum were evaluated. The hydration level of stratum corneum was measured using an instrument measuring moisture content in stratum corneum of skin surface (product name: SKICON-200, manufactured by I.B.S. CO. LTD.). Whenever the measurement was performed, the hydration level of stratum corneum in 9 sites in each sample-applied portion was measured, and an average of 7 values excluding the maximum and minimum values was taken as a hydration level of stratum corneum in the sample-applied portion.

Figure 3:
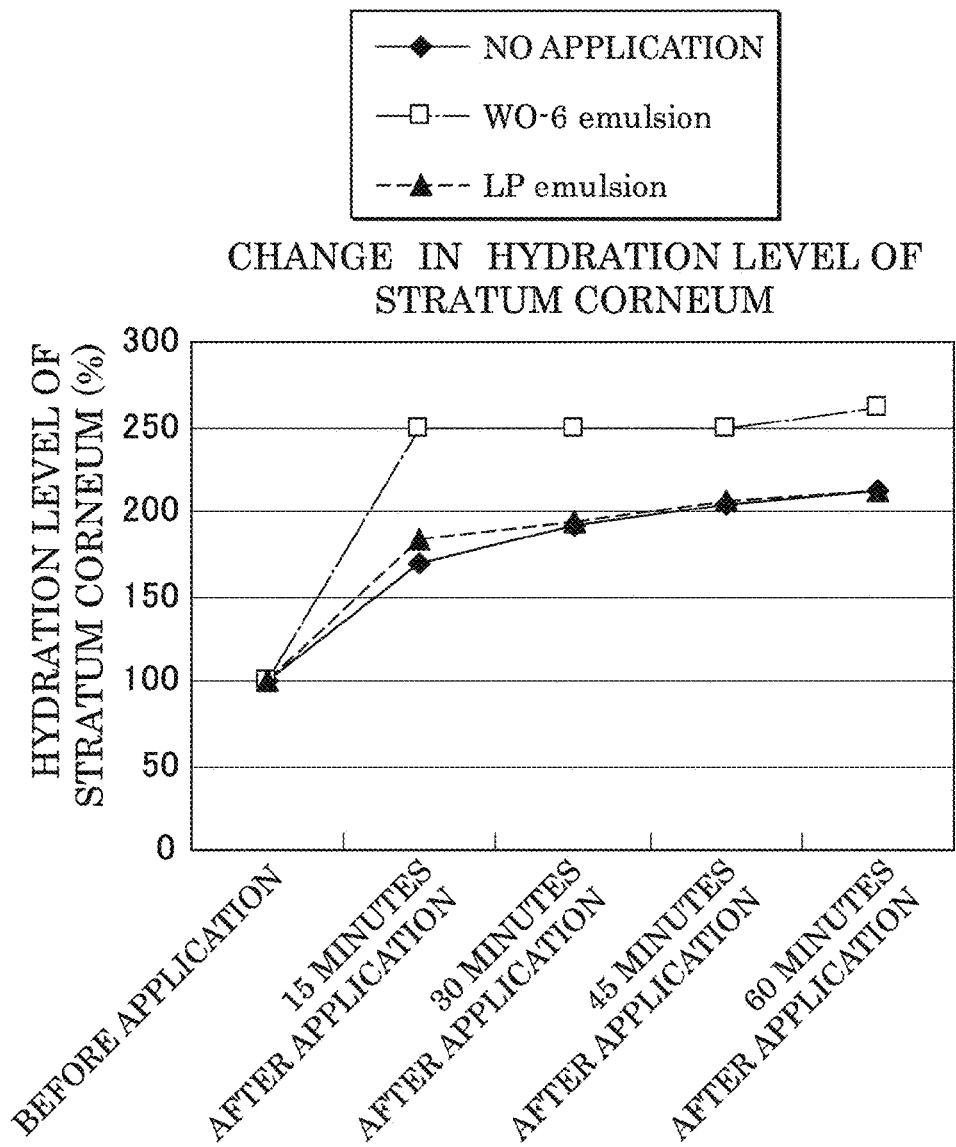
FIG. 3 is a view showing temporal change of the hydration level of stratum corneum to which the compositions for external use on skins of Examples 148 and 149 are applied.

FIG. 3 shows the temporal change in the hydration level of stratum corneum in the respective sample-applied portions. As a result, there was practically no difference between the hydration level of stratum corneum ("LP emulsion" in the table) of the skin to which the oil-in-water type emulsion composition of Example 149 mixed with non-polar oil was applied and the hydration level of stratum corneum ("no application" in the table) of the skin to which nothing was applied. On the other hand, the hydration level of stratum corneum ("WO-6 emulsion" in the table) of the skin to which the oil-in-water type emulsion composition of Example 148 mixed with high-polarity oil was applied was higher about 1.5 times the hydration level of stratum corneum of the skin to which nothing was applied, and this trend lasted to the point in time when 60 minutes elapsed after the application. From these results, it was understood that the composition for external use on skin of the present invention that is mixed with high-polarity oil is markedly excellent in moisturizing properties, and that if this composition for external use on skin is applied, moisturizing properties of the skin can be improved.

INDUSTRIAL APPLICABILITY

The composition for external use on skin of the present invention can be suitably used in the fields of producing various cosmetics, quasi-drugs, drugs, cleaning agents, and the like.

The invention claimed is:

1. A composition for external use on skin, comprising 0.1% by mass to 10% by mass of the following component (A);
   0.5% by mass to 40% by mass of a divalent polyol as a component (B); and
   30% by mass or more of the following component (D);
   Component (A): A water-soluble polymer obtained by mixing agar having a weight average molecular weight of 10000 to 60000 with xanthan gum at a ratio of 4:6 to 8:2 in terms of a mass ratio;
   Component (B): at least one component selected from the group consisting of propylene glycol, 1,3-propanediol, 3-methyl-1,3-butanediol, 1,2-pentanediol, dipropylene glycol, and 1,2-hexanediol; and
   Component (D): Water.

2. The composition for external use on skin according to claim 1, further comprising:
   0.001% by mass to 20% by mass of one or more kinds of moisturizers selected from hyaluronic acid or salts thereof, pyrrolidone carboxylate or salts thereof, glycerin, diglycerin, and polyglycerin, as a component (C).

3. The composition for external use on skin according to claim 1 or 2, further comprising:
   5% by mass to 60% by mass of powder as a component (H).

4. The composition for external use on skin according to claim 3,
   wherein the component (H) is hydrophobic powder.

5. The composition for external use on skin according to claim 1, further comprising:
   0.01% by mass to 64% by mass of oil as a component (E).

6. The composition for external use on skin according to claim 5,
   wherein the oil as the component (E) contains one or more kinds of silicone oils selected from chain-like polysiloxane and cyclic polysiloxane.

7. The composition for external use on skin according to claim 5,
   wherein the component (E) contains oil having a relative permittivity at 20° C. of 3.0 or more.

8. The composition for external use on skin according to claim 5,
   wherein the component (E) contains two or three or more kinds of oils incompatible with each other, and the oils are held in the composition while being incompatible with each other.

9. The composition for external use on skin according to claim 1, in which practically no surfactant is mixed in.

10. The composition for external use on skin according to claim 1, further comprising:
    0.0001% by mass to 60% by mass of a surfactant as a component (F).

11. The composition for external use on skin according to claim 10,
    wherein the component (F) is an ionic surfactant.

12. The composition for external use on skin according to claim 10,
    wherein the component (F) is an amphoteric surfactant.

13. The composition for external use on skin according to claim 1,
    wherein a value of Mw/Mn of a weight average molecular weight (Mw) and a number average molecular weight (Mn) of the agar in the component (A) is 1.1 to 8.0.

14. The composition for external use on skin according to claim 1, comprising:
    0.5% by mass to 30% by mass of the divalent polyol as the component (B).

15. The composition for external use on skin according to claim 1, further comprising:
    0.01% by mass to 10% by mass of one or more kinds selected from water-soluble ionic substances, as a component (G).

16. The composition for external use on skin according to claim 15,
    wherein the water-soluble ionic substance as the component (G) is one or more kinds selected from a group consisting of ascorbic acid, an ascorbic acid derivative, and salts thereof.

17. The composition for external use on skin according to claim 1, which is produced by a step of holding a water-soluble polymer solution, which contains the water-soluble polymer as the component (A) and at least all or a portion of water as the component (D) and in which the water-soluble polymer as the component (A) exists in a dissolved state, at 85° C. to 95° C. for 50 minutes or longer.

18. A cosmetic comprising:
the composition for external use on skin according to claim 1.

19. A cleaning agent comprising:
the composition for external use on skin according to claim 10.

20. A method of producing a cosmetic,
wherein a powder dispersion composition that contains 0.1% by mass to 10% by mass of the following component (A), 30% by mass or more of the following component (D), and 5% by mass to 60% by mass of the following component (H) is used as a cosmetic raw material;

Component (A): A water-soluble polymer obtained by mixing agar having a weight average molecular weight of 10000 to 60000 with xanthan gum at a ratio of 4:6 to 8:2 in terms of a mass ratio;

Component (D): Water; and

Component (H): Powder.

21. A method of producing a composition for external use on skin, comprising:
a step of holding a water-soluble polymer solution, which contains the water-soluble polymer as the component (A) and at least all or a portion of water as the component (D) and in which the water-soluble polymer as the component (A) exists in a dissolved state, at 85° C. to 95° C. for 50 minutes or longer.

\* \* \* \* \*